United States Patent
Baxter et al.

Patent Number: 6,087,490
Date of Patent: Jul. 11, 2000

[54] DINUCLEOTIDE AND OLIGONUCLEOTIDE ANALOGUES

[75] Inventors: Anthony David Baxter, Abingdon; Eric Keith Baylis, Stockport; Stephen Paul Collingwood, Crawley; Robin Alec Fairhurst, Ashington; Roger John Taylor, Southwater, all of United Kingdom

[73] Assignee: Novartis AG, Basel, Switzerland

[21] Appl. No.: 09/155,198

[22] PCT Filed: Nov. 3, 1997

[86] PCT No.: PCT/GB97/00651
§ 371 Date: Oct. 8, 1998
§ 102(e) Date: Oct. 8, 1998

[87] PCT Pub. No.: WO97/35869
PCT Pub. Date: Oct. 2, 1997

[30] Foreign Application Priority Data

Mar. 23, 1996 [GB] United Kingdom .................... 9606158

[51] Int. Cl.[7] .......................... C07H 21/00; C07H 19/00; C07H 21/02; C07H 21/04
[52] U.S. Cl. .......................... 536/25.3; 435/6; 536/22.1; 536/23.1; 536/25.31; 536/25.33; 536/25.34; 536/25.4; 536/25.41; 536/25.6; 514/1; 514/44
[58] Field of Search .......................... 435/6; 536/22.1, 536/23.1, 25.3, 25.31, 25.33, 25.34, 25.4, 25.41, 25.6; 514/1, 44

[56] References Cited

U.S. PATENT DOCUMENTS 5,789,562 8/1998 Seela et al. .......................... 536/22.1

FOREIGN PATENT DOCUMENTS

| | | |
|---|---|---|
| 2080231 | 10/1991 | Canada . |
| 2087818 | 7/1993 | Canada . |
| 2111384 | 6/1994 | Canada . |
| 552766 | 7/1993 | European Pat. Off. . |
| 602524 | 6/1994 | European Pat. Off. . |
| 614 907 | 9/1994 | European Pat. Off. . |
| 680969 | 11/1995 | European Pat. Off. . |
| WO 91 15499 | 10/1991 | WIPO . |

OTHER PUBLICATIONS

Rammler D.H. et al., Biochemistry, vol. 6, No. 6, pp. 1828–1837 (1967). *

*Primary Examiner*—Jezia Riley
*Attorney, Agent, or Firm*—Joseph J. Borovian

[57] ABSTRACT

A compound which is a dinucleotide analogue of formula

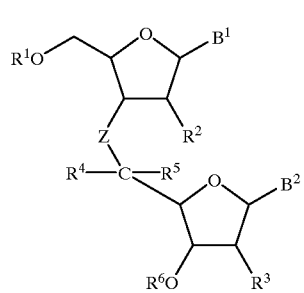

I or a salt thereof, where
$B^1$ and $B^2$ are each independently a monovalent nucleoside base radical,
$R^1$ is hydrogen or $Y^1$,
$R^2$ and $R^3$ are each independently hydrogen, halogen, hydroxy or $-OY^2$,
$R^4$ is hydrogen, halogen, hydroxy, $-OY^3$ or $R^7$,
$R^5$ is hydrogen, halogen or $R^8$,
$R^6$ is hydrogen, $Y^4$ or a phosphoramidyl group,
Z is a group of formula II, III or IV

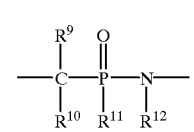

II

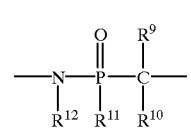

III

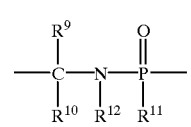

IV where $R^9$ is hydrogen, halogen, hydroxy, $-OY^5$ or $R^{13}$, $R^{10}$ is hydrogen, halogen or $R^{14}$, $R^{11}$ is hydroxy, $R^{15}$ or $-OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}{}_a$ or $-OCOR^{12}{}_a$ where $R^{12}{}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each indpendently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group.

18 Claims, No Drawings

DINUCLEOTIDE AND OLIGONUCLEOTIDE ANALOGUES

This invention relates to chemical compounds which are dinucleotide analogues, to their preparation and to oligonucleotide analogues incorporating at least one unit derived therefrom.

For several years there has been interest in structural analogues of natural oligonucleotides because of their utility as antisense inhibitors of protein expression in biological systems and as pharmaceuticals in the treatment of viruses such as influenza, herpes and HIV, and in the treatment of cancer. Amongst the analogues of recent interest are those in which the groups linking the sugar moieties of oligonucleotides are modified by the replacement of the 3' and 5' oxy linkages by other linking groups.

WO 91/15499 describes oligonucleotides which are said to be of general formula

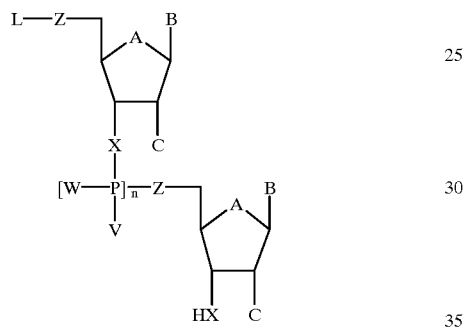

where B is a nucleic acid base; A is —O— or —CH$_2$—; X and Z are each —O—, —S—, —NH— or —CH$_2$— where X and Z may be the same or different; V and W are =O, =S, =Se, —NH$_2$, alkoxy, —OH or —SH, where V and W may be the same or different in a monomer unit; L is —H or a partner of a bonding pair; C is —OR where R is an alkyl, alkenyl or alkynyl group optionally substituted by one or more halogen, cyano, carboxy, hydroxy, nitro and/or mercapto radicals; and n is any integer.

WO 91/15499 does not disclose any oligonucleotides of the above formula in which one of X and Z is —NH— and the other is —CH$_2$, one of V and W is =O and the other is alkoxy, and does not suggest how such compounds might be prepared. The preparation of such oligonucleotides has remained a problem. It has now been found that such oligonucleotides can be prepared from novel dinucleotide analogues. The novel dinucleotide analogues, and oligonucleotides containing units derived therefrom, have good stability towards nuclease hydrolysis and good hybridization properties, facilitating their use as antisense inhibitors of gene expression and as pharmaceuticals for the treatment of diseases such as cancer and viruses such as influenza, herpes and HIV.

Accordingly, the present invention provides compounds which are dinucleotide analogues of formula

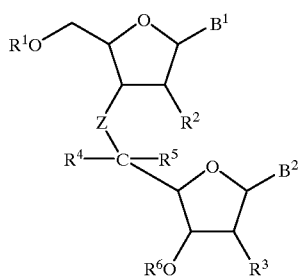

I and salts thereof, where

B$^1$ and B$^2$ are each independently a monovalent nucleoside base radical,

R$^1$ is hydrogen or Y$^1$,

R$^2$ and R$^3$ are each independently hydrogen, halogen, hydroxy or —OY$^2$,

R$^4$ is hydrogen, halogen, hydroxy, —OY$^3$ or R$^7$,

R$^5$ is hydrogen, halogen or R$^8$,

R$^6$ is hydrogen, Y$^4$ or a phosphoramidyl group,

Z is a group of formula II, III or IV

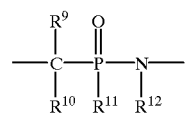

II

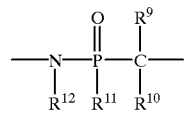

III

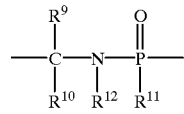

IV where R$^9$ is hydrogen, halogen, hydroxy, —OY$^5$ or R$^{13}$, R$^{10}$ is hydrogen, halogen or R$^{14}$, R$^{11}$ is hydroxy, R$^{15}$ or —OR$^{15}$ where R$^{15}$ is a C$_1$ to C$_{10}$ aliphatic group, a C$_3$ to C$_8$ cycloaliphatic group, a C$_6$ to C$_{10}$ aromatic group or a C$_7$ to C$_{13}$ araliphatic group, and R$^{12}$ is hydrogen, R$^{12}_a$ or —COR$^{12}_a$ where R$^{12}_a$ is a C$_1$ to C$_{10}$ aliphatic group, a C$_3$ to C$_8$ cycloaliphatic group, a C$_6$ to C$_{10}$ aromatic group or a C$_7$ to C$_{13}$ araliphatic group, Y$^1$, Y$^2$, Y$^3$, Y$^4$ and Y$^5$ are each indpendently a hydroxy-protecting group, and R$^7$, R$^8$, R$^{13}$ and R$^{14}$ are each independently a C$_1$ to C$_{10}$ aliphatic group, a C$_3$ to C$_8$ cycloaliphatic group, a C$_6$ to C$_{10}$ aromatic group or a C$_7$ to C$_{13}$ araliphatic group.

The hydroxy-protecting groups Y$^1$ to Y$^5$ may be any groups capable of protecting a hydroxyl group against undesired reaction. Such groups are well known. Generally, Y$^1$ to Y$^5$ are protecting groups previously specified for use in nucleotide chemistry. Preferably, Y$^1$ is R$^{16}$, —COR$^{16}$ or —SO$_2$R$^{16}$, Y$^2$ is R$^{17}$, —COR$^{17}$ or —SO$_2$R$^{17}$, Y$^3$ is R$^{18}$, —COR$^{18}$ or —SO$_2$R$^{18}$, Y$^4$ is R$^{19}$, —COR$^{19}$ or —SO$_2$R$^{19}$ and Y$^5$ is R$^{20}$, —COR$^{20}$ or —SO$_2$R$^{20}$, or one or more of Y$^1$ to Y$^5$ is tri(C$_1$–C$_{15}$ hydrocarbyl)silyl, where R$^{16}$, R$^{17}$, R$^{18}$, R$^{19}$ and R$^{20}$ are each independently a C$_1$ to C$_{10}$ aliphatic group, a C$_3$ to C$_8$ cycloaliphatic group, a C$_6$ to C$_{10}$ aromatic group or a C$_7$ to C$_{40}$ araliphatic group.

Preferably the hereinbefore mentioned aliphatic groups are independently unsubstituted or substituted alkyl or alkenyl groups, the hereinbefore mentioned cycloaliphatic groups are independently unsubstituted or substituted cycloalkyl groups, the hereinbefore mentioned aromatic groups are independently unsubstituted or substituted aryl groups and the hereinbefore mentioned araliphatic groups are independently unsubstituted or substituted aralkyl groups, preferred substituents in the substituted groups being halogen, hydroxy, $C_1$ to $C_4$ alkoxy, cyano or nitro.

The substituted or unsubstituted alkyl groups may be, for example, substituted or *unsubstituted methyl, ethyl, n-propyl, isopropyl, n-butyl, isobutyl, tert-butyl, n-pentyl, neopentyl, n-hexyl, n-octyl, 2-ethylhexyl or n-decyl, $C_1$ to $C_4$ alkyl groups being preferred.

The substituted or unsubstituted alkenyl groups may be, for example, substituted or unsubstituted vinyl, allyl, 1-propenyl, isopropenyl, methallyl, 2-butenyl, 1-butenyl, isobutenyl, pentenyl, hexenyl, octenyl or decenyl, $C_2$ to $C_4$ alkenyl groups being preferred.

The substituted or unsubstituted cycloalkyl groups may be, for example, substituted or unsubstituted cyclopropyl, cyclobutyl, cyclopentyl, methylcyclopentyl, cyclohexyl, methylcyclohexyl, dimethylcyclohexyl, tert-butylcyclohexyl, cycloheptyl or cyclooctyl, $C_5$ to $C_8$ cycloalkyl groups being preferred. The substituted or unsubstituted aryl groups may be, for example, substituted or unsubstituted phenyl, o-tolyl, m-tolyl, p-tolyl, o-xylyl, m-xylyl, p-xylyl, alpha-naphthyl, beta-naphthyl or dimethylnaphthyl, $C_6$ to $C_8$ aryl groups being preferred.

The substituted or unsubstituted $C_7$ to $C_{13}$ aralkyl groups may be, for example, substituted or unsubstituted benzyl, 4-methylbenzyl, 2-phenylethyl, 2-phenylpropyl, 3-phenylpropyl or diphenylmethyl, $C_7$ to $C_9$ aralkyl groups being preferred. The substituted or unsubstituted $C_1$ to $C_{40}$ aralkyl groups may be, for example, substituted or unsubstituted benzyl, 4-methylbenzyl, 2-phenylethyl, 2-phenylpropyl, 3-phenylpropyl, diphenylmethyl or triphenylmethyl(trityl), $C_7$ to $C_{20}$ aralkyl groups being preferred. Especially preferred are $C_1$–$C_4$-alkoxy-substituted $C_7$ to $C_{20}$ aralkyl groups such as methoxytrityl, dimethoxytrityl or tris-tert-butyltrityl.

Amongst the preferred alkyl, alkenyl, cycloalkyl, aryl and aralkyl groups, especially preferred groups are those which are unsubstituted or substituted by halogen, hydroxy, $C_1$ to $C_4$ alkoxy (particularly methoxy or ethoxy), cyano or nitro.

When $R^2$ and/or $R^3$ are $OY^2$, in certain preferred embodiments $Y^2$ is $R^{17}$ where $R^{17}$ is $C_1$ to $C_4$ alkyl, especially methyl or ethyl, or $C_1$ to $C_4$ alkoxy —$C_1$ to $C_4$ alkyl, especially methoxyethyl, which group is not only a hydroxy-protecting group but is also a significant feature in the oligonucleotide into which the dinucleotide of formula I is incorporated.

The phosphoramidyl group may be a group of formula

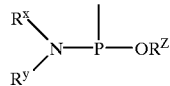

where $R^x$ and $R^y$ are independently $C_1$ to $C_{10}$ alkyl groups, which may be unsubstituted or substituted, for example by hydroxy, and $R^z$ is a $C_1$ to $C_{10}$ alkyl group, which may be unsubstituted or substituted, for example by hydroxy or cyano, or a $C_2$ to $C_{10}$ alkenyl group. Preferably $R^x$ and $R^y$ are $C_1$ to $C_4$ alkyl and $R^z$ is $C_2$ to $C_4$ alkenyl or cyano-substituted $C_1$ to $C_4$ alkyl. Most preferably, $R^x$ and $R^y$ are each isopropyl and $R^z$ is 2-cyanoethyl.

When a tri($C_1$–$C_{15}$ hydrocarbyl)silyl or tri($C_1$–$C_{15}$ hydrocarbyl)silyloxy group is present in compounds of formula I, the tri($C_1$–$C_{15}$ hydrocarbyl)silyl radical may be, for example, trialkylsilyl such as trimethylsilyl, triethysilyl, tri-n-propylsilyl, tri-isopropysilyl, tri-n-butylsilyl, tri-isobutysilyl, iospropyidimethylsilyl, tert.butyldimethylsilyl or 1,1,2,2-tetramethylethyidimethylsilyl (thexyldimethylsilyl), triarysilyl such as triphenylsilyl, tri-aryalkylsilyl such as tribenzylsilyl, aryldialkylsilyl such as phenyldimethylsilyl, phenyidiethylsilyl, phenyidiisopropyl-silyl or phenyl di-tert-butylsilyl, or alkyldiarylsilyl such as methyidiphenylsilyl, isopropyldiphenylsilyl or tert-butyldiphenylsilyl, preferably $C_1$–$C_6$ alkyldi($C_6$–$C_8$ aryl) silyl, especially tert-butyldiphenylsilyl, or branched $C_2$–$C_{10}$ alkyl di ($C_1$–$C_4$ alkyl)silyl, especially thexyldimethylsilyl.

$B^1$ and $B^2$ may be the same or different and may be radicals of bases found in naturally occuring nucleosides, which may be unsubstituted or substituted, for example on a nitrogen atom by a protecting group, e.g. an acyl group, which may be aliphatic such as acetyl, or aromatic such as benzoyl or nitrobenzoyl, or by an aralkyloxyalkyl protecting group such as benzyloxymethyl, or synthetic analogues of such bases. Other types of protecting groups conventionally used in nucleotide chemistry which may be present on a nitrogen atom in $B^1$ and $B^2$ include amidine groups, such as N,N-dimethyl formamidine, N,N-dimethylacetamidine and N-methylpyrrolidine amidine groups, and alkoxy carbonyl groups such as tert-butoxy carbonyl which convert an amino group into a carbamate group.

Thus $B^1$ and $B^2$ may each independently be a radical of a purine or pyrimidine base such as -adenine, guanine, cytosine, thymine or uracil, or an analogue of these bases such as 2-aminoadenine, 6-hydroxypurine, 5-methylcytosine, 5-propynylcytosine, 5-fluorouracil, 5-propynyluracil or dihydrouracil, or such a radical substituted on a nitrogen atom, for example by a protecting group as hereinbefore described.

Preferably, $B^1$ and $B^2$ are each independently a monovalent radical of a pyrimidine base, more preferably a thymine or cytosine base, especially where $B^1$ and $B^2$ are each independently 1-thyminyl, N-hydroxymethyl-1-thyminyl, N-benzyloxymethyl-1-thyminyl, 5-methylcytosinyl, N-benzoyl-5-methylcytosinyl or N(N'-methyl-2-pyrrolidonylidene)-5-methylcytosinyl.

In preferred compounds of the invention, $R^2$ and $R^3$ are independently hydrogen, hydroxy, $C_1$ to $C_4$ alkoxy or $C_1$–$C_4$ alkoxy-substituted $C_1$ to $C_4$ alkoxy, $R^4$ and $R^5$ are independently hydrogen or $C_1$ to $C_4$ alkyl, $R^9$ is hydrogen or hydroxy and $R^{10}$ is hydrogen or $C_1$ to $C_4$ alkyl. In more preferred compounds, $B^1$ and $B^2$ are pyrimidine base radicals, $R^1$ is hydrogen, $C_1$ to $C_4$ alkyl, unsubstituted or $C_1$ to $C_4$ alkoxy-substituted $C_7$ to $C_{20}$ aralkyl, ($C_1$ to $C_6$ alkyl) di($C_6$ to $C_8$ aryl) silyl, or branched $C_2$ to $C_{10}$ alkyldi($C_1$ to $C_4$ alkyl)silyl, $R^6$ is hydrogen, $C_1$ to $C_4$ alkyl, unsubstituted or $C_1$ to $C_4$ alkoxy-substituted $C_7$ to $C_{20}$ aralkyl, unsubstituted or halogen-substituted benzoyl, ($C_1$ to $C_6$ alkyl)di ($C_6$ to $C_8$ aryl)silyl or cyano-$C_1$ to $C_4$ alkyl-N, N-di($C_1$ to $C_4$ alkyl)phosphoramidyl, $R^{11}$ is hydroxy, $R^{15}$ or —$OR^{15}$ where $R^{15}$ is unsubstituted or hydroxy-, alkoxy- or cyano-substituted $C_1$ to $C_4$ alkyl or $C_2$ to $C_4$ alkenyl, and $R^{12}$ is hydrogen or $C_1$ to $C_4$ alkyl.

In especially preferred compounds of the invention, $B^1$ and $B^2$ are 1-thyminyl, N-hydroxymethyl-1-thyminyl, N-benzyloxymethyl-1-thyminyl, 5-methylcytosinyl, N-benzoyl-5-methylcytosinyl or N(N'-methyl-2-pyrrolidinylidene)-5-methylcytosine, $R^1$ is hydrogen, 4,4'-dimethoxytriphenylmethyl (dimethoxytrityl), tert-butyldiphenylsilyl or thexyldimethylsilyl, $R^2$, $R^4$ and $R^5$ are each hydrogen, $R^3$ is hydrogen or methoxy, $R^6$ is hydrogen, dimethoxytriphenylmethyl, tert-butyldiphenylsilyl, benzoyl, 4-fluorobenzoyl or 2-cyanoethyl-N,N-diisopropylphosphoramidyl, $R^9$ and $R^{10}$ are each hydrogen, $R^{11}$ is hydroxy, methoxy, ethoxy, 2-cyanoethoxy or allyloxy and $R^{12}$ is hydrogen or methyl.

Compounds of the invention may be in the form of one of the possible isomers, for example as a diastereoisomer, an optical isomer or a racemate, or a mixture thereof. Preferred isomers of compounds of formula I are those of formula V, VI or VII:

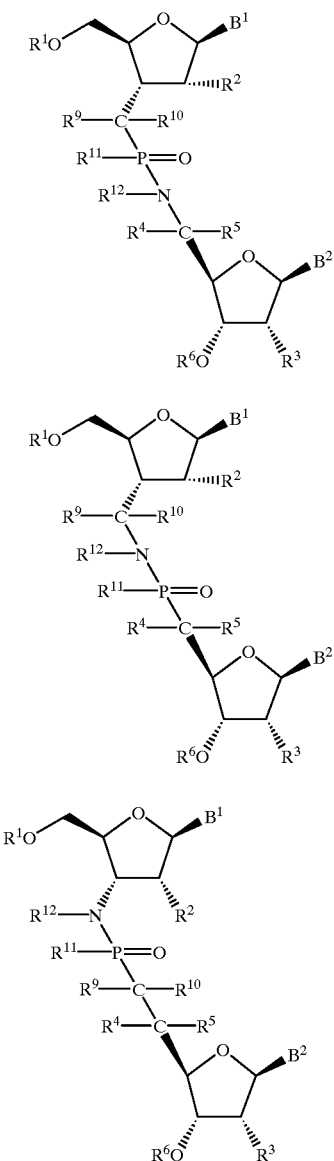

Differences may be observed in properties such as mRNA binding properties, nuclease resistance and biological efficacy for different stereochemistry at phosphorus in compounds of the invention.

Specific especially preferred compounds of the invention are described hereinafter in the Examples.

Compounds of formula I where Z is a group of formula II may be prepared by reacting a compound of formula

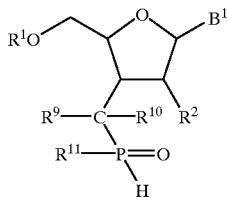

VIII with a compound of formula

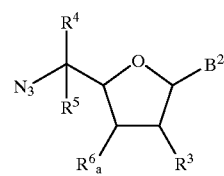

IX where $B^1$, $B^2$, $R^1$, $R^2$, $R^3$, $R^4$, $R^5$, $R^9$, $R^{10}$ and $R^{11}$ are as hereinbefore defined and $R^6_a$ is hydrogen or $Y^4$ to give a compound of formula I where $R^{12}$ is hydrogen and, optionally, reacting the product to replace $R^{12}$ as hydrogen by $R^{12}$ as $R^{12}_a$, where $R^{12}_a$ is as hereinbefore defined and/or reacting the product where $R^{12}$ is hydrogen or $R^{12}_a$ to replace one or more protecting groups by a hydrogen atom.

The reaction between the compounds of formulae VIII and IX may be carried out in a non-protic organic solvent, preferably pyridine, in the presence of a silylating agent and optionally in the presence of an additional base, for example a tertiary amine such as triethylamine. Preferably the reaction is carried out in pyridine using a silylacetamide, particularly bistrimethylsilyl trifluoroacetamide (BSTFA). The reaction may be carried out at a temperature from −100 to 250° C., preferably under anhydrous conditions. Usually, the reactants are mixed and maintained at low temperature, e.g. −50° C. to ambient temperature, for 15 minutes to 18 hours, preferably 15 minutes to 18 hours, to form a silylated intermediate, the reaction mixture then being heated, either directly or after evaporation and mixing with methanol and chloroform, to give a compound of formula I where $R^{12}$ is hydrogen.

Compounds of formula VIII may be prepared by reacting a compound of formula

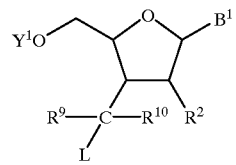

X with a compound of formula

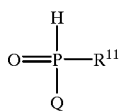

XI where $B^1$, $R^2$, $R^9$, $R^{10}$, $R^{11}$ and $Y^1$ are as hereinbefore defined, L is a leaving atom or group and Q is a protecting group, to give a compound of formula

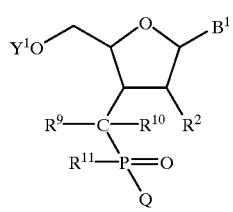

XII and then reacting the compound of formula XII to replace Q by hydrogen and, if desired, reacting the product to replace $Y^1$ by hydrogen.

The leaving atom or group L may be, for example, a halogen atom or a residue of an organic or inorganic acid after removal of an acidic hydrogen atom therefrom, such as an organic sulphonate group, e.g. a methanesulphonate, trifluoromethanesulphonate or p-toluenesulphonate group. Preferably L is a chlorine, bromine or iodine atom or an organic sulphonate group, especially an iodine atom.

The reaction between the compound of formula X and the compound of formula XI may be carried out under conventional conditions for substitution reactions at a P—H bond, for example in the presence of a base such as a tertiary amine, an alkali metal (usually sodium), an organometal of an alkali metal or magnesium (usually an alkyllithium), an alkali metal hydride (usually sodium hydride), or an alkali metal amide such as lithium diisopropylamide or, especially, potassium bis (trimethylsilyl)amide. The reaction may be carried out in an organic solvent, usually an ether such as diethyl ether or tetrahydrofuran, or a hydrocarbon such as hexane or toluene, and at a temperature from −100° C. to 100° C., usually from −80° C. to 40° C.

Compounds of formula X may be prepared by reducing an aldehyde of formula

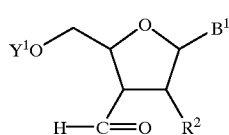

XIII where $B^1$, $R^2$ and $Y^1$ are as hereinbefore defined, for example using sodium borohydride, to the corresponding alcohol, and carrying out esterification and/or nucleophilic displacement reactions on the alcohol, for example esterifying the alcohol by reaction with an organic sulphonyl chloride optionally followed by reaction with an alkali metal halide to introduce a halogen atom, or reacting the alcohol with a halogenating reagent, in particular a phosphonium halide such as methyl(triphenoxy)phosphonium iodide to replace the alcoholic hydroxyl directly by halogen. These reactions may be carried out using conventional conditions and procedures.

Aldehydes of formula XIII may be prepared by reduction of the corresponding $3^1$-cyano compound with diisobutylaluminum hydride or otherwise as described in WO 92/20823. Aldehydes of formula XIII may also be prepared by treatment of the corresponding $3^1$-amino compound with nitrite as described by S. Shuto et al, Nucleosides & Nucleotides 1 (3), 263–272 (1982), or by hydrolysis of the corresponding $3^1$-C-(4,5-dihydro-5-methyl-1,3,5-dithiazin-2-yl) compound as described by Bamford et al, J. Med. Chem. 1990, 33, 2494.

The protecting group Q may be any group which is known to be effective in protecting P—H bonds whilst reactions are carried out which would affect such bonds and be readily removable after such reactions to generate a P—H bond. Such protecting groups may be, for example, those in compounds of formula la of EP 0009348, or those in compounds described in Aust. J. Chem. 33, 292 (1980) or U.S. Pat. No. 4,933,478. Preferred protecting groups Q are $C_1$ to $C_{20}$ hydrocarbyl groups, preferably alkyl groups, substituted on the carbon atom thereof attached to the indicated phosphorus atom by at least one hydroxy, $C_1$-$C_{10}$ alkoxy, di($C_1$-$C_{15}$ hydrocarbyl)silyloxy or tri($C_1$-$C_{15}$ hydrocarbyl)silyloxy group, including those of formulae

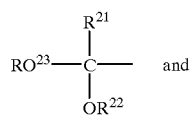

XIV

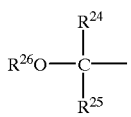

XV where $R^{21}$ is hydrogen, $C_1$-$C_{10}$ alkyl, $C_3$-$C_8$ cycloalkyl, $C_6$-$C_1$ aryl or $C_7$-$C_{11}$ aralkyl, $R^{22}$ and $R^{23}$ are independently $C_1$-$C_{10}$ alkyl, $C_2$-$C_4$ alkenyl, $C_6$-$C_{10}$ aryl or $C_7$-$C_{13}$ aralkyl, $R^{24}$ and $R^{25}$ are independently $C_1$-$C_{10}$ alkyl, or $R^{24}$ is $C_1$-$C_{10}$ alkyl and $R^{25}$ is $C_6$-$C_{10}$ aryl, and $R^{26}$ is hydrogen, di($C_1$-$C_{15}$ hydrocarbyl)silyl or tri($C_1$-$C_{15}$ hydrocarbyl)silyl. Preferred groups of formula XIV are those where $R^{21}$ is hydrogen or $C_1$-$C_4$ alkyl and $R^{22}$ and $R^{23}$ are each $C_1$-$C_4$ alkyl. Preferred groups of formula XV are those where $R^{24}$ and $R^{25}$ are $C_1$-$C_4$ alkyl, and $R^{26}$ is hydrogen, tri($C_1$-$C_{10}$ alkyl)silyl or branched $C_2$-$C_{10}$ alkyl di($C_1$-$C_4$ alkyl)silyl. In especially preferred compounds, Q is a group of formula XIV where $R^{21}$ is hydrogen or methyl and $R^{22}$ and $R^{23}$ are each methyl or ethyl or a group of formula XV where $R^{24}$ and $R^{25}$ are each methyl and $R^{26}$ is hydrogen, trimethylsilyl or tert-butyl dimethylsilyl.

Compounds of formula XI where the protecting group Q is of formula XIV as hereinbefore defined and $R^{11}$ is —$OR^{15}$ where $R^{15}$ is as hereinbefore defined are protected phosphinate esters which can be prepared by known methods, for example as described in EP 0 009 348, U.S. Pat. No. 4,933,478 or Aust. J. Chem. 33,212 (1980).

Compounds of formula XI where the protecting group Q is of formula XV as hereinbefore defined and $R^{11}$ is —$OR^{15}$ where $R^{15}$ is as hereinbefore defined are protected phosphinate esters, which can be prepared by esterifying a phosphinic acid of formula

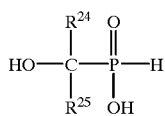

XVI with an alcohol of formula $R^{15}$ OH where $R^{15}$, $R^{24}$ and $R^{25}$ are as hereinbefore defined. The esterification may be carried out at −20 to 30° C., preferably 0 to 10° C. It is conveniently carried out in a solvent, preferably an ether such as tetrahydrofuran, preferably in the presence of a base, usually a tertiary amine such as dimethylaminopyridine, and a dehydrating agent such as N,$N^1$-dicyclohexylcarbodiimide.

Phosphinic acids of formula XVI can be prepared by reacting hypophosphorous acid with a ketone of formula

XVII where $R^{24}$ and $R^{25}$ are as hereinbefore defined, or by reacting hypophosphorous acid with a ketal of this ketone using the procedure described by S. J. Fitch, J. Amer. Chem. Soc. 86, 61(1964), followed by hydrolysis of the resulting phosphonous ester, for example by heating with water.

Compounds of formula XI where the protecting group Q is of formula XIV as hereinbefore defined and $R^{11}$ is $R^{15}$ as hereinbefore defined are protected phosphine oxides which can be prepared by reacting a protected phosphinate ester of formula

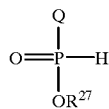

XVIII where $R^{27}$ is $C_1$–$C_4$ alkyl and Q is a group of formula XIV as hereinbefore defined, with an organomagnesium halide of formula $R^{15}$ Mg X or an organolithium of formula $R^{15}$ Li, where $R^{15}$ is as hereinbefore defined and X is halogen.

Reaction of compounds of formula XII, or other compounds described herein containing a protecting group Q, to replace Q by a hydrogen atom may be carried out using known procedures. For example, where the protecting group Q is of formula XIV, it may be effected by reaction with a trialkylsilyl halide such as trimethylsilyl chloride or trimethylsilyl bromide. The reaction may be carried out at a temperature of −30° C. to 100° C., preferably 0° C. to 40° C., preferably under anhydrous conditions, in an organic solvent, for example a halohydrocarbon such as chloroform or trichloroethane, an ether such as tetrahydrofuran or an aromatic hydrocarbon such as benzene, toluene or xylene, or a mixture of two or more of such solvents. When a trialkylsilyl chloride is used, the reaction is carried out in the presence of an alcohol such as ethanol. Reaction of compounds containing Q to replace Q by a hydrogen atom can also be effected by treatment with an organic acid, preferably under anhydrous conditions. When the protecting group a is of formula XV, hydrolysis to replace Q by a hydrogen atom can be effected by treatment with a base, for example by treatment with aqueous ammonia or a hindered base such as triethylamine or 1,8-diazabicyclo[5.4.0]undec-7-ene (DBU), in the presence of alcoholic/aqueous solvent, at a temperature from ambient temperature to 100° C. When $R^{11}$ is —$OR^{15}$, this group is also affected by the basic hydrolysis; for example, when ammonia, DBU or an alkali metal hydroxide or carbonate is used for the hydrolysis, $R^{15}$ is replaced by ammonium or an alkali metal ion respectively which in turn is replaced by hydrogen on acidification of the basic hydrolysis product. The resulting hydroxyl group can be re-esterified, if desired, for example by reaction with an alkyl chloroformate in the presence of a tertiary amine or by reaction with an alcohol and a carbodiimide such as dicyclohexylcarbodiimide, optionally in the presence of a base such as 4-dimethylaminopyridine.

Compounds of formula IX are, in general, known compounds and may be prepared by known methods. For example, they may be prepared by reacting a compound of formula

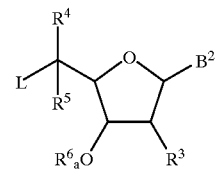

XIX where $B^2$, $R^3$, $R^4$, $R^5$, $R^6_a$ and L are as hereinbefore defined, with an inorganic azide, preferably an alkali metal azide, especially sodium azide or lithium azide. The reaction is generally carried out in an organic solvent, preferably an aprotic polar solvent such as acetonitrile, dimethyl sulphoxide or, especially, dimethyl formamide, at a temperature from 40 to 200° C., preferably 40 to 120° C., preferably using 1 to 10 mol of inorganic azide per mol of compound of formula XIX.

Compounds of formula XIX may be prepared from the corresponding alcohols of formula

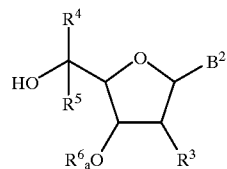

XX where $B^2$, $R^3$, $R^4$, $R^5$ and $R^6_a$ are as hereinbefore defined, by methods analogous to those used for the preparation of compounds of formula X from their corresponding alcohols as hereinbefore described.

Compounds of formula I where Z is a group of formula II may also be prepared by reacting a compound of formula VIII with a compound of formula

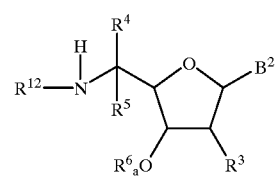

XXI and carbon tetrachloride or trichlorobromomethane in the presence of a tertiary amine, where $B^2$, $R^3$, $R^4$, $R^5$, $R^6_a$ and $R^{12}$ are as hereinbefore defined, and, optionally, where $R^{12}$ is hydrogen, reacting the product to replace $R^{12}$ as hydrogen by $R^{12}$ as $R^{12}_a$ as hereinbefore defined and/or reacting the product where $R^{12}$ is hydrogen or the product where $R^{12}$ is $R^{12}_a$ to replace one or more protecting groups by hydrogen.

The reaction between compounds of formulae VIII and XXI and carbon tetrachloride or trichlorobromomethane may be carried out in a solvent such as an ether, a hydrocarbon, -pyridine or dichloromethane and at a temperature from −70 to 110° C. The carbon tetrachloride or trichlorobromomethane reacts with the P—H group in the compound of formula VIII to give a P—Cl intermediate (Atherton-Todd reaction) which then reacts with the amine group in the compound of formula XXI. Preferably, the reaction is carried out in dichloromethane or a mixture thereof with pyridine and at a temperature from −20 to 70° C., especially −20 to 20° C. Preferred tertiary amines include dimethylaminopyridine and, especially, triethylamine. Preferably 0.8 to 1.3 mols of the compound of formula VIII is reacted with 1 mol of the compound of formula XXI and 0.8 to 1.3 mols of carbon tetrachloride or trichlorobromomethane in the presence of 5 to 10 mols of the tertiary amine. The reaction is usually complete within 16 to 24 hours.

Compounds of formula XXI are, in general, known and may be prepared by known methods, for example by reacting the corresponding compound having a leaving atom or group L as hereinbefore defined at the 5' position with a compound of formula $R^{12}NH$, where $R^{12}$ is as hereinbefore defined, or otherwise as described in WO 92/20823.

Compounds of formula I where Z is a group of formula III may be prepared by reacting a compound of formula

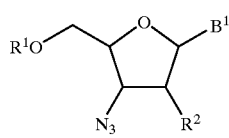

XXII with a compound of formula

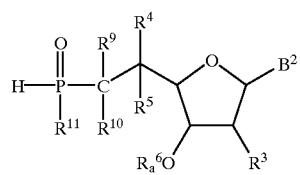

XXIII where $B^1$, $B^2$, $R^1$, $R^2$, $R^3$, $R^4$, $R^5$, $R^6_a$, $R^9$, $R^{10}$ and $R^{11}$ are as hereinbefore defined, to give a compound of formula i in which $R^{12}$ is hydrogen and, optionally, reacting the compound where $R^{12}$ is hydrogen to give a compound where $R^{12}$ is $R^{12}_a$ as hereinbefore defined and/or reacting the compound where $R^{12}$ is hydrogen or the compound where $R^{12}$ is $R^{12}_a$ to replace one or more protecting groups by hydrogen.

The reaction between compounds of formulae XXII and XXIII may be carried out using a solvent, catalyst and conditions as hereinbefore described for the analogous reaction between compounds of formulae VIII and IX.

Compounds of formula XXII are, in general, known and may be prepared by known methods, for example from compounds of formula

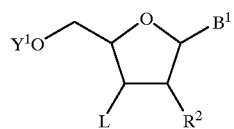

XXIV where $B^1$, $R^2$, $Y^1$ and L are as hereinbefore defined, by methods analogous to those hereinbefore described for the preparation of compounds of formula IX from compounds of formula XIX followed, where desired, by reaction to replace $Y^1$ by hydrogen. Compounds of formula XXIV may be prepared from the corresponding 3'-alcohols by methods analogous to those hereinbefore described for preparation of compounds of formula X from their corresponding alcohols. Compounds of formula XXIII are, in general, known and may be prepared as described in EP 0614906 or EP 0629633.

Compounds of formula I where Z is a group of formula III may also be prepared by reacting a compound of formula

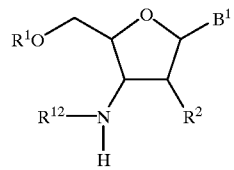

XXV where $B^1$, $R^1$, $R^2$, and $R^{12}$ are as hereinbefore defined, with carbon tetrachioride or trichlorobromomethane and a compound of formula XXIII and, optionally, where $R^{12}$ is hydrogen, reacting the product to replace $R^{12}$ as hydrogen by $R^{12}$ as $R^{12}_a$ as hereinbefore defined and/or reacting the product where $R^{12}$ is hydrogen or the product where $R^{12}$ is $R^{12}_a$ to replace one or more protecting groups by hydrogen. The reaction between the compound of formula XXV, carbon tetrachloride or bromotrichloromethane, and the compound of formula XXIII may be carried out as hereinbefore described for the analogous reaction of a compound of formula XXI with carbon tetrachloride or bromotrichloromethane and a compound of formula VIII.

Compounds of formula XXV are, in general, known and may be prepared by known methods, for example by reacting the corresponding compound having a leaving atom or group L as hereinbefore defined in the 3' position and where $R^1$ is $Y^1$ as hereinbefore defined with a compound of formula $R^{12}NH$, where $R^{12}$ is as hereinbefore defined, followed, if desired, by reaction to replace $Y^1$ by hydrogen, or otherwise as described in WO 92/20823.

Compounds of formula I where Z is a group of formula IV may be prepared by reacting a compound of formula

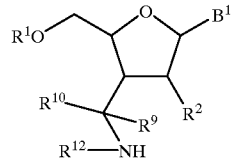

XXVI with carbon tetrachloride or bromotrichloromethane and a compound of formula

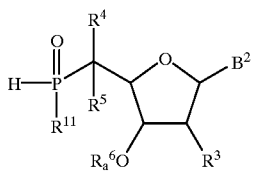

XXVII where $B^1$, $B^2$, $R^1$, $R^2$, $R^3$, $R^4$, $R^5$, $R^6{}_a$, $R^9$, $R^{10}$, $R^{11}$ and $R^{12}$ are as hereinbefore defined and, optionally, where $R^{12}$ is hydrogen, reacting the product to replace $R^{12}$ as hydrogen by $R^{12}$ as $R^{12}{}_a$, where $R^{12}{}_a$ is as hereinbefore defined, and/or reacting the product where $R^{12}$ is hydrogen or $R^{12}{}_a$ to replace one or more protecting groups by hydrogen.

The reaction between the compound of formula XXVI, carbon tetrachloride or bromotrichloromethane and the compound of formula XXVII may be carried out as hereinbefore described for the analogous reaction between a compound of formula XXI, carbon tetrachloride or bromotrichloromethane and a compound of formula VIII.

Compounds of formula XXVI may be prepared by known methods, for example by reacting the corresponding compound having a —$CH(R^{10})L$ group in the 3' position, where $R^{10}$ and L are as hereinbefore defined, and where $R^1$ is $Y^1$ as hereinbefore defined with a compound of formula $R^{12}NH$, where $R^{12}$ is as hereinbefore defined, followed, if desired, by reaction to replace $Y^1$ by hydrogen, or otherwise as described in WO 92/20823.

Compounds of formula I where Z is a group of formula IV may also be prepared by reacting a compound of formula

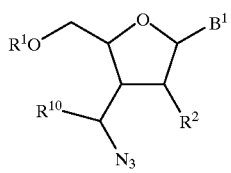

XXVIII where $B^1$, $R^1$, $R^2$ and $R^{10}$ are as hereinbefore defined, with a compound of formula XXVII to give a compound of formula I where $R^{12}$ is hydrogen and, optionally, reacting this compound to replace $R^{12}$ as hydrogen by $R^{12}$ as $R^{12}{}_a$ as hereinbefore defined and/or reacting the compound of formula I where $R^{12}$ is hydrogen or $R^{12}{}_a$ to replace one or more protecting groups by hydrogen. The reaction between the compounds of formulae XXVIII and XXVII may be carried out as hereinbefore described for the analogous reaction between compounds of formulae VIII and IX.

Compounds of formula XXVIII may be prepared by known methods, for example from compounds of formula

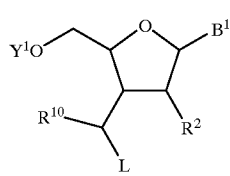

XXIX where $B^1$, $R^2$, $R^{10}$, $Y^1$ and L are as hereinbefore defined, by methods analogous to those hereinbefore described for the preparation of compounds of formula IX from compounds of formula XIX, followed, if desired, by reaction to replace $Y^1$ by hydrogen. Compounds of formula XXIX may be prepared from the corresponding 3'—$CH(R^{10})OH$ alcohols by methods analogous to those hereinbefore described for preparation of compounds of formula X from their corresponding alcohols.

Compounds of formula XXVII are novel compounds which may be prepared by reacting a compound of formula XIX with a compound of formula XI to give a novel compound of formula

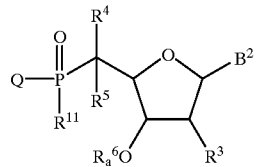

XXVIIA where $B^2$, $R^3$, $R^4$, $R^5$, $R^6{}_a$, $R^{11}$ and Q are as hereinbefore defined and then reacting the compound of formula XXVIIA to replace Q by hydrogen.

The reaction between compounds of formulae XIX and XI may be carried out as hereinbefore described for the analogous reaction between compounds of formulae X and XI.

Compounds of formula I where $R^{12}$ is H may be converted into compounds of formula I where $R^{12}$ is $R^{12}{}_a$ by reaction with a compound of formula $R^{12}{}_aX$ where $R^{12}{}_a$ is as hereinbefore defined and X is halogen, preferably chlorine, bromine or iodine, any hydrogen atom attached to nitrogen in $B^1$ or $B^2$ optionally being replaced by a protecting group such as an acyl or aralkyloxyalkyl group, e.g. acetyl, nitrobenzoyl or benzyloxymethyl, before the reaction with the compound of formula $R^{12}{}_aX$ and then, if desired, regenerated after such reaction by removal of the protecting group.

Replacement of a nitrogen-attached hydrogen atom by a protecting group in $B^1$ or $B^2$ in a compound of formula I or other compounds containing such a hydrogen atom described herein may be carried out by known methods. For example the compound with the nitrogen-attached hydrogen atom may be reacted with a compound of formula $Y^6L$ where $Y^6$ is an unsubstituted or substituted $C_1$–$C_4$ alkyl- or $C_6$–$C_8$ aryl-carbonyl group, for example acetyl, benzoyl, p-fluorobenzoyl or p-nitrobenzoyl, an unsubstituted or substituted $C_1$–$C_4$ alkyl- or $C_6$–$C_8$ aryl- sulphonyl group, for example trifluoromethanesulphonyl or p-toluenesulphonyl, or a $C_7$–$C_{13}$ aryloxy- $C_1$–$C_4$ alkyl group, for example benzyloxymethyl, and L is a leaving atom or group as hereinbefore defined. This reaction may be carried out using known procedures in the presence of a base, which may be an organic base such as triethylamine, pyridine, Hunig's base or diazabicycloundecane (DBU), or an inorganic base such as potassium carbonate. Preferably the reaction is carried out in a solvent such as a halohydrocarbon e.g. dichloromethane or chloroform, an ether e.g. tetrahydrofuran or, especially, acetonitrile, at a temperature from –100° C. to 50° C., especially at –5° C. to 5° C.

Protection of N—H in $B^1$ or $B^2$ in compounds described herein with an amidine group may be effected as described by McBride et al, J.Am.Chem.Soc. 1986, 108, 2040–2048.

The reaction between the compound of formula I in which $R^{12}$ is hydrogen and the compound of formula $R^{12}{}_aX$ may be carried out using known procedures for alkylation of amines. Generally, the reaction is carried out in the presence of an organic base such as triethylamine, pyridine or DBU or an alkali metal hydride or organometallic alkyl compound, in an organic solvent at a temperature from −100° C. to 250° C. Preferably it is carried out in the presence of an alkyllithium sodium hydride or, especially, potassium hydride, in a non-protic solvent such as dimethyl formamide, an ether such as tetrahydrofuran or a hydrocarbon, especially toluene, at a temperature from −50° to 200° C., especially ambient temperature to 50° C.

Removal of the NH-protecting group after the reaction with the compound of formula $R^{12}{}_aX$ may be carried out using known methods. For example, this may be carried out by hydrogenolysis or by treatment with an organic acid such as trifluoroacetic acid, with an alkali metal amide, usually sodium or lithium amide, in ethanol, or at low temperature with a mixture of boron trifluoride etherate and phenyl mercaptan in dichloromethane, or, where the protecting group is an acyl group such as acetyl or benzoyl, by hydrolysis with an aqueous base, e.g. aqueous ammonia. Preferably, removal of a benzyloxymethyl protecting group is carried out by reaction with hydrogen at 1 to 50 atmospheres in the presence of a palladium catalyst, especially a palladium on carbon catalyst, in water, an alcohol, hydrocarbon, ester, especially methanol or ethanol, as solvent, at a temperature from −20 to 150° C., especially 10 to 40° C. Where hydrogenolysis leaves a hydroxymethyl group on the nitrogen atom, this may be replaced by hydrogen by treatment with an alkali metal alkoxide, preferably sodium methoxide, in alcohol, or with an aqueous acid.

Compounds of formula I and other compounds described herein containing one or more hydroxy-protecting groups, e.g. one or more of groups $Y^1$ to $Y^5$, may be reacted to replace the protecting group by a hydrogen atom using known methods, for example as described in Protective Groups in Organic Synthesis, T. W. Greene and P. G. Wuts, 2nd Edition, Wiley Interscience 1991. For example, where a silyl ether protecting group is present, as it is in certain preferred compounds of formula I where $R^1$ and $R^6$ are trihydrocarbylsilyl groups, it may be cleaved using methods described on pages 60 to 67 of the cited Greene and Wuts book. Replacement of a trihydrocarbylsilyl group by hydrogen is usually effected by reaction with alcoholic alkali metal hydroxide, with a strong mineral acid such as hydrochloric acid or, preferably, with a fluoride such as cesium fluoride or a quaternary ammonium fluoride in an organic solvent, for example a hydrocarbon, chlorinated hydrocarbon, dimethyl formamide, dimethyl sulphoxide, acetonitrile or, preferably, an ether, especially tetrahydrofuran. In one preferred embodiment, a compound of formula I where $R^1$ and $R^6$ each denote trihydrocarbylsilyl is reacted with tetra-n-butylammonium fluoride in tetrahydrofuran at a temperature from 0° C. to ambient temperature, to give a compound of formula I in which $R^1$ and $R^6$ are each hydrogen.

A compound of formula I where $R^1$ is an optionally substituted $C_7$ to $C_{30}$ aralkyl group and $R^6$ is hydrogen may be prepared by reacting a compound of formula I in which $R^1$ and $R^6$ are each hydrogen with an optionally substituted $C_7$ to $C_{30}$ aralkyl halide, which may be a bromide, iodide or, preferably, a chloride, or an optionally substituted $C_7$ to $C_{30}$ aralkyl pyridinium salt such as the fluoroborate, in an organic non-protic solvent such as acetonitrile, dichloromethane or dimethylformamide, optionally in the presence of a base, preferably an organic base such as triethylamine or, especially, pyridine. The reaction may be carried out at a temperature from −50 to 100° C., preferably −20 to 50° C., especially 0° C. to ambient temperature.

A compound of formula I in which $R^6$ is a phosphoramidyl group may be prepared by reacting a compound of formula I where $R^6$ is hydrogen with an aliphatic bis(N,N-dialkyl)phosphordiamidite such as 2-cyanoethyl bis (N,N-diisopropyl)phosphordiamidite in the presence of an ammonium tetrazolide such as diisopropylammonium tetrazolide, or with an aliphatic N,N-dialkylchlorophosphoramidite such as 2-cyanoethyl N,N-diisopropylchlorophosphoramidite in the presence of an organic base such as triethylamine or, preferably, dimethylaminopyridine. The reaction is conveniently carried out in an inert atmosphere in a non-protic organic solvent such as dichloromethane. It can be carried out at temperatures from −20 to 50° C., preferably 0° C. to ambient temperature.

The nature of the base radicals $B^1$ and $B^2$ in the compounds of the invention and in reactants used in their preparation may be modified by appropriate reaction thereof. For example, compounds where $B^1$ and/or $B^2$ are 1-thyminyl, may be reacted with triazole and phosphorus oxychloride to give a 4-triazolylthyminyl derivative, which may be cleaved with a base to give a 4-aminothyminyl derivative, i.e. a compound where $B^1$ and/or $B^2$ are 5-methylcytosinyl. The reaction of the compound where $B^1$ and/or $B^2$ are 1-thyminyl with triazole and phosphorus oxychloride is usually carried out under anhydrous conditions at −30° C. to 100° C., preferably −10° C. to 30° C., especially 0° C. to 20° C., in the presence of a tertiary amine such as triethylamine, in a solvent such as pyridine. Base cleavage of the 4-triazolylthyminyl compound is conveniently effected by treatment with concentrated aqueous ammonia at 0° C. to 100° C., preferably at 15° C. to 30° C., in a solvent such as dioxan or tetrahydrofuran.

Compounds of the invention may be in the form of pharmaceutically acceptable, i.e. physiologically tolerable, salts. For example, a compound of formula I in which $R^{11}$ is hydroxy, which is a phosphinic acid, may in the form of a pharmaceutically acceptable salt with a base. Such salts include alkali metal salts such as sodium or potassium salts, alkaline earth metal salts such as magnesium or calcium salts, or ammonium salts with ammonia or organic amines, preferably tertiary monoamines and heterocyclic bases such as triethylamine, tri(2-hydroxyethyl)amine, N-ethylpiperidine or N,N¹-dimethylpiperazine.

Since all compounds of formula I contain basic groups $B^1$ and $B^2$, they may be in the form of acid addition salts with organic or inorganic acids. Acids which form suitable salts include hydrohalic acids, for example hydrochloric and hydrobromic acid, sulphuric acid, phosphoric acid, nitric acid or perchloric acid, or aliphatic, alicyclic, aromatic or heterocyclic carboxylic or sulphonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic, p-aminosalicylic, embonic, methanesulphonic, ethanesulphonic, hydroxyethanesulphonic, ethylenedisulphonic, halobenzenesulphonic, toluenesulphonic, naphthalenesulphonic and sulphanilic acids, methionine, tryptophan, lysine, arginine and ascorbic acid.

Salts of this invention may be prepared by conventional salt-forming procedures.

When mixtures of diastereomers of compounds of formula I or intermediates are obtained, these can be separated by known methods, for example by fractional distillation, crystallization or chromatography.

The present invention also provides oligonucleotides containing at least one unit derived from dinucleotide analogues of formula I, and the use of dinucleotide analogues of formula I in the synthesis of such oligonucleotides. Such oligonucleotides may contain only units derived from the same or different dinucleotide analogues of formula I, preferably of formula V, VI or VII, or may contain at least one unit derived from a dinucleotide of formula I and at least one other unit derived from another natural or synthetic nucleoside. Generally, the oligonucleotides contain 2 to 200 nucleoside—derived units. Preferred oligonucleotides contain 2 to 100, more preferably 2 to 50, especially 2 to 30 such units. Preferably, the oligonucleotides contain units of the same or different dinucleotide analogues of formula I together with units of natural or synthetic nucleoside derived from D-ribose or 2-deoxyribose.

The present invention further provides oligonucleotides of formula

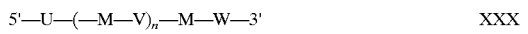

where U, V and W are the same or different residues of natural or synthetic nucleosides and at least one of the residues U, V and W being derived from a dinucleotide analogue of formula I and having the formula

XXXI

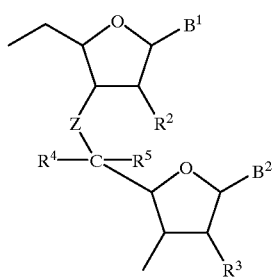

where $B^1$, $B^2$, $R^2$, $R^3$, $R^4$, $R^5$ and Z are as hereinbefore defined, M is a nucleoside-bridging group and n is a number from 0 to 200, preferably 0 to 100, more preferably 0 to 50, especially 0 to 30. A preferred bridging group M is the group —OP(O)(O$^-$)O— or —OP(O)(S$^-$)O—. Examples of further bridging groups are —OP(S)(S$^-$)O—, —OP(O)(R$^{28}$)O—, —OP(O)(NR$^{29}$R$^{30}$)O— or —OCH$_2$O— where R$^{28}$ is hydrogen or $C_1$–$C_6$ alkyl and R$^{29}$ and R$^{30}$ are independently hydrogen or $C_1$–$C_6$ alkyl, and bridging groups —NHCOCH$_2$—, —CH$_2$CONH— or —N(CH$_3$)—O—CH$_2$—.

In formula XXX, M may represent the same of different bridging groups in different positions. Similarly, where V occurs more than once in formula XXX, it may represent the same or different nucleoside residue in the different positions where it occurs.

The residues derived from one or more dinucleotides of formula I can be bonded terminally or in the nucleotide sequence whereby several, for example 2 to 5, residues derived from one or more dinucleotide analogues of formula I can be bonded between residues of natural or synthetic nucleosides, or there can be mixed forms of this distribution lying in the nucleotide sequence. Preferably there are 4 to 30 nucleoside units, of which preferably 1 to 12, especially 1 to 6 and particularly 1 to 4 units are residues derived from dinucleotide analogues of formula I.

Particularly preferred embodiments are oligonucleotides of formula XXX where n is 2 to 50, preferably 2 to 30, M is a group —OP(O)(O$^-$)O— or —OP(O)(S$^-$)O— U, V and W are the same or different residues of a natural nucleoside, and at least one of the residues U, V and W is of formula XXXI and $B^1$ and $B^2$ are natural nucleoside base radicals. The natural nucleoside may be, for example, adenosine, cytosine, guanosine, uridine, 2-aminoadenosine, 5-methylcytosine, 2'-deoxyadenosine, 2'-deoxycytosine, 2'-deoxyguanosine or thymidine. The residue of formula XXXI can be bound terminally or in the nucleotide sequence, whereby several, for example 2 to 5, of the same or different residues of formula XXXI can follow one another, or the same or different residues of formula XXXI can be bound between residues of natural nucleosides, or mixed types of these distributions can lie in the nucleotide sequence.

In another especially preferred embodiment of oligonucleotides of formula XXX, U, V and W are the same or different residues of formula XXXI in which $B^1$ and $B^2$ are natural nucleoside base radicals. In this embodiment, n is preferably 2 to 20, especially 1 to 12, more especially 1 to 6 and most especially 1 to 4.

The preparation of oligonucleotides according to the invention can be carried out using known procedures, if necessary automatically using commercial nucleic acid synthesizing machines. In the case of the bridging group —OP(O)(O$^-$)O—, for example, the phosphotriester process, the phosphite triester process or the H-phosphonate process can be used, all of which are familiar to those skilled in the art. Many suitable procedures are described in Oligonucleotides and Analogues: A Practical Approach, edited by F. Eckstein, Oxford University Press, 1991.

In a typical procedure, a dinucleotide analogue of formula I where $R^1$ and $R^6$ are each hydrogen, i.e. where the 3' and 5' hydroxyls are free, is reacted with 4,4'-dimethoxytriphenylmethyl chloride in the presence of a base, for example using the procedure described in Example 3 of WO 92/20823, to give a dinucleotide analogue of formula I where $R^1$ is a dimethoxytrityl group, which is then reacted with 2-cyanoethyl-N,N,N',N'-tetraisopropyl phosphordiamidite to replace the 3' hydroxyl by a 2-cyanoethyl-N,N-diisopropylphosphoramidyloxy group, thereby activating the dinucleotide analogue for coupling at the 3' position. The functionalized dinucleotide analogues obtained can be inserted into any desired sequence using, for example a CPG-solid support and standard nucleic acid synthesizing machine such as Biosystems 380B and 394 and Milligen/Biosearch 7500 and 8800s.

The dinucleotide analogues of the invention and oligonucleotides incorporating units derived therefrom can be used in therapeutics, for example in the treatment of a human or other animal suffering from a disease which is modulated by a protein, or in the treatment of viruses such as influenza, herpes and HIV. Accordingly, the present invention also provides a pharmaceutical composition comprising as active ingredient a dinucleotide analogue of the invention, or an oligonucleotide incorporating at least one unit derived therefrom. Optimum dosages and treatment schedules can readily be determined by those skilled in the art. When administered to mammals of about 70 kg weight, the dose can be, for example, 0.01 to 1000 mg per day. It will generally be preferred to administer therapeutic agents in accordance with the invention internally, for example orally, by inhalation, intravenously or intramuscularly. Other methods of administration, such as transdermal, topical or interlesional methods, and by inclusion in suppositories, can also be useful. Use in conjuction with pharmacologically acceptable carriers is preferred for some therapeutic treatments.

The oligonucleotides according to the invention have a surprisingly high stability to degradation by nucleases. A very good pairing with complementary nucleic acid strands, particularly of the RNA type, is also observed. The oligonucleotides according to the invention are therefore particularly suitable for antisense technology, i.e. for inhibition of the expression of undesired protein products due to the binding to suitable complementary nucleotide sequence in nucleic acids (see EP 0 266 099, WO 87/07300 and WO 89/08146). They can be employed for the treatment of infections and diseases, for example by blocking the expression of bioactive proteins at the nucleic acid stage (for example oncogenes). The oligonucleotides according to the invention are also suitable as diagnostics and can be used as gene probes for the detection of viral infections or of genetically related diseases by selective interaction at the single or double-stranded nucleic acid stage. In particular—due to the increased stability to nucleases—diagnostic use is not only possible in vitro but also in vivo (for example tissue samples, blood plasma and blood serum). Use possibilities of this type are described, for example, in WO 91/06556.

The pharmacologically active dinucleotides and oligonucleotides according to the invention can be used in the form of parentally administrable preparations or of infusion solutions. Solutions of this type are preferably isotonic aqueous solutions or suspensions, it being possible to prepare these before use, for example in the case of lyophilized preparations which contain the active substance on its own or together with a carrier, for example mannitol. The pharmaceutical preparations can be sterilized and/or contain excipients, for example preservatives, stabilizers, wetting and/or emulsifying agents, solubilizers, salts for regulating the osmotic pressure and/or buffers. The pharmaceutical preparations, which if desired can contain further pharmacologically active substances such as, for example, antibiotics, are prepared in a manner known per se, for example by means of conventional dissolving or lyophilizing processes, and contain about 0.1% to 90%, in particular from about 0.5% to about 30%, for example 1% to 5% of active substance(s).

This invention is illustrated by the following Examples.

Compounds used in the Examples, and precursors thereof, are prepared as follows. All $^{31}P$ data for these compounds and those of the Examples are for $^1H$ decoupled. In the formulae for these compounds the abbreviations used have the following meanings: DMTr: dimethoxytrityl, Et: ethyl, $^{Me}C^{BZ}$: N-benzoyl-5-methylcytosinyl, iPr isopropyl, Ph: phenyl, T: 1-thyminyl, $T^{BOM}$: N-benzyloxymethyl-1-thyminyl, tBDPS: tert-butyldiphenylsilyl Compound A

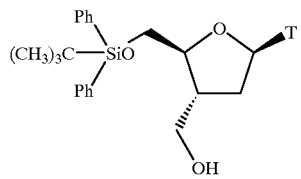

Ph = phenyl
T = 1-thyminyl

To a solution of an aldehyde of formula XIII where $R^2$ is hydrogen, $B^1$ is 1-thyminyl and $R^1$ is tert-butyl diphenylsilyl, prepared as described in WO 92/20823, (11.2 g, 23 mmol) in anhydrous ethanol (120 ml) at room temperature is added $NaBH_4$ (865 mg, 23 mmol) portionwise over 5 minutes. After 1 hour, the reaction mixture is quenched with water, diluted with ethyl acetate (500 ml) and washed with water (2×50 ml). After back extraction of the aqueous phase, the combined organic phase is dried ($MgSO_4$) and concentrated to give Compound A as a white solid.

$^1H$ nmr ($CDCl_3$, 400 MHz) δ 9.10 (1H. s, NH) 7.65 (4H, d, Ar 4× CH ortho), 7.40 (7H, m, Ar 4× CH meta, 2× CH para+H6), 6.13 (1H, t, H1'), 4.00 (1H, dd, H5'), 3.93 (1H, m, H4'), 3.82 (1H, dd, H5'), 3.62 (2H, m, $CH_2OH$), 2.60 (1H, m, H3'), 2.32 (1H, m, H2'), 2.12 (1H, m, H2'), 1.62 (3H, s, T-$CH_3$) and 1.10 (9H, s, $^tBu$) ppm.

Compound B

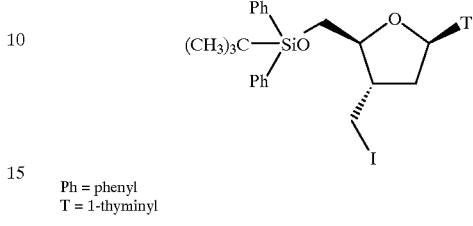

Ph = phenyl
T = 1-thyminyl

To a solution of Compound A (9 g, 18.1 mmol) in dry DMF (100 ml) at 0–5° C. is added 2,6-lutidine (4.25 ml, 36.5 mmol) followed by methyltriphenoxyphosphonium iodide (9.45 g, 20.9 mmol). The resulting mixture is allowed to warm to room temperature. After 1 hour the mixture is diluted (200 ml ethyl acetate) and washed with 0.1N $Na_2S_2O_3$ (2×20 ml), 0.5N hydrochloric acid (2×20 ml) and water (2×20 ml). Drying, concentration and purification by flash silica column chromatography (gradient elution chloroform: ethyl acetate 20:1–7:1) gives Compound B as a white solid.

Found C, 53.35; H, 5.55; N, 4.35% $C_{27}H_{33}IN_2O_4Si$ requires C, 53.65; H, 5.5; N, 4.65%.

$^1H$ nmr ($CDCl_3$, 400 MHz) δ10.2 (1H, s, NH) 7.66 (4H, d, 4× CH ortho), 7.40 (7H, M, 4× CH meta, 2× CH para+H6) 6.19 (1H, t, H1') 4.02 (1H, dd, H5'), 3.82 (1H, m, H4') 3.78 (1H, dd, HS'), 3.17 (1H, dd, $CH_2I$) 3.10 (1H, dd $CH_2I$), 2.68 (1H, m, H3'), 2.30 (1H, m, H2') 2.23 (1H, m, H2') 1.66 (3H, s, $CH_3$-T), 1.10 (9H, s, tBu) ppm.

Compound C

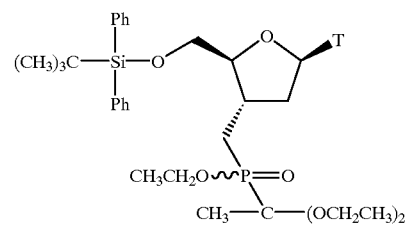

(Ph = phenyl, T = 1-thyminyl)

To a solution of ethyl (1,1-diethoxyethyl) phosphinate (5.51 g, 26.2 mmol) in dry THF (170 ml), under argon, at −78° C. is added a solution of potassium bis(trimethylsilyl) amide (34.6 ml, 0.75M solution in toluene) dropwise over 5 minutes. The resulting solution is stirred at −78° C. for 1 hour. A solution of Compound B (5.0 g, 8.25 mmol) in dry THF (20 ml) is then added dropwise over 5 minutes. Stirring is continued at −78 ° C. for 1 hour before warming to room temperature over 2 hours. Saturated aqueous ammonium chloride (50 ml) is then added and the whole mixture extracted with ethyl acetate (500 ml). The organic phase is washed with saturated ammonium chloride (2×50 ml) and water (2×50 ml), dried over magnesium sulphate and concentrated. Purification by flash silica column chromatography (eluant ethylacetate: ethanol 30:1) gives Compound C as a 1:1 mixture of diastereoisomers epimeric at phosphorus.

Found C, 59.55; H, 7.8; N, 3.85%; $C_{35}H_{51}N_2O_8PSi.H_2O$ requires C, 59.65; H, 7.6; N, 4.0%.

Hereinafter tBDPS denotes tert-butyldiphenyisilyl.
Compound $C_1$

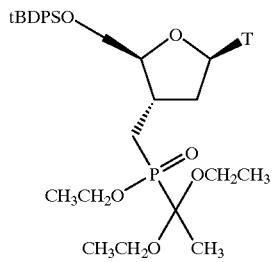

The diastereomer mixture obtained as Compound C is separated by flash column chromatography on silica gel, eluting with 9:1 ethyl acetate/ethanol to give higher running diastereomer A (Compound $C_2$) then lower running diastereomer B (Compound C ,).
Diastereomer A=$^{31}$P (CDCl$_3$, 162 MHz) $\delta$ 46.7 ppm
Diastereomer B=$^{31}$P (CDCl$_3$, 162 MHz) $\delta$ 47.0 ppm
Compound D

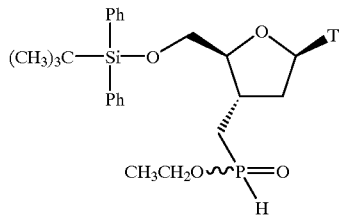

(Ph = phenyl, T = 1-thyminyl)

Trimethylsilylchloride (4.44 ml, 35 mmol) is added dropwise (2 minutes) at room temperature to a stirred solution of Compound C (2.4 g, 3.5 mmol) in chloroform (25 ml) containing ethanol (1%) under argon. After standing at −20° C. for 60 hours, a further portion of trimethylsilylchioride (2.22 ml, 17.5 mmol) is added along with ethanol (200 μl) and the resulting solution stirred at room temperature for 7 hours. Concentration and co-evaporation with chloroform (50 ml) gives a white solid which is purified by flash silica column chromatography (eluant chloroform: ethanol 13:1) to give Compound D as a white solid isolated as a 1:1 mixture of diastereoisomers.
Found: C, 59.95; H, 7.25; N, 4.65%; $C_{29}H_{39}N_2O_6$PSi.½H$_2$O C, 60.1; H, 6.95; N, 4.85%.
$^{31}$P nmr $^1$H decoupled (CDCl$_3$, 162 MHz) $\delta$ 34.5 and 34.3 ppm
Compound $D_1$

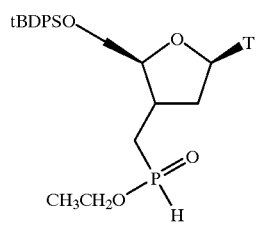

The procedure used for the preparation of Compound D is repeated using the diastereomer B Compound $C_1$ (0.80 g, 1.16 mmol) in place of Compound C, and using 1.48 ml (11.6 mmol) of trimethylsilylchloride, 0.8 ml of ethanol and 16 ml of chloroform instead of the amounts used in the preparation of Compound D. The product isolated is predominantly the Compound $D_1$. Less than 5% epimerization occurs in this reaction leading to a small amount of the diastereomer A H-phosphinate.
Diastereomer B: $^{31}$P (CDCl$_3$, 162 MHz) $\delta$ 34.4 ppm
Diastereomer A: $^{31}$P (CDCl$_3$, 162 MHz) $\delta$34.2 ppm
Compound $D_2$ The procedure used for the preparation of Compound D is repeated using the diastereomer A Compound $C_2$ (5.24 g, 7.63 mmol) in place of Compound C and using 0.97 ml (7.63 mmol) of trimethylsilylchloride, 0.56 ml of ethanol and 38 ml of dichloromethane in place of chloroform instead of the amounts used in the preparation of Compound D. The product isolated is predominantly Compound $D_2$. Less than 5% epimerization occurs in this reaction leading to a small amount of the diastereomer B H-phosphinate.
Compound E

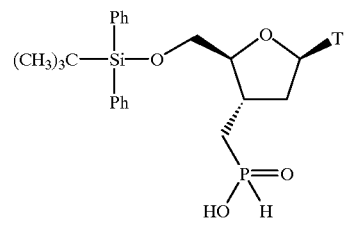

(Ph = phenyl, T = 1-thyminyl)

A solution of Compound D (0.78 g, 1.37 mmol) in ethanol (2.7 ml), water (1.4 ml) and triethylamine (2.7 ml) is stirred at room temperature. After 3 hours, the reaction mixture is diluted with ethyl acetate (25 ml), and washed successively with 0.05M aqueous HCl (1×10 ml) and water (1×10 ml). The organic extract is dried over magnesium sulphate and evaporated to give Compound E as a clear colorless viscous oil.
$^{31}$P (162 MHz, CDCl$_3$) $\delta$ 35.47 ppm
Compound F

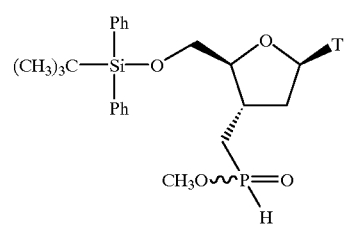

(Ph = phenyl, T = 1-thyminyl)

Dicyclohexylcarbodiimide (109 mg, 530 μmol) is added to a solution of Compound E (230 mg, 424 μmol) and 2,6-dimethyl-4-amino pyridine (0.6 mg, 5 μmol) in methanol (21.5 ||1, 530 μmol) and tetrahydrofuran (4.2 ml) at 0° C. After stirring for 4 hours at room temperature, the reaction mixture is filtered and then evaporated. Flash column chromatography of the evaporation residue on silica, eluting with 95% ethyl acetate, 5% methanol gives Compound F, a 1:1 mixture of diastereomers epimeric at phosphorus, as a viscous clear colorless oil.
$^{31}$P (162 MHz, CDCl$_3$) $\delta$ 37.32, 37.08 ppm.
Found C, 58.32; H, 6.57; N, 4.83%; $C_{28}H_{37}N_2O_6$PSi.H$_2$O requires C, 58.52; H, 6.84; N, 4.87%.

Compound G

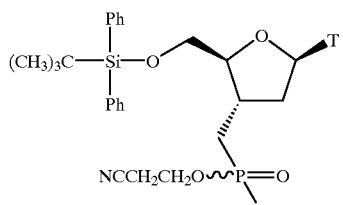

(Ph = phenyl, T = 1-thyminyl)

Dicyclohexylcarbodiimide (104 mg, 506 μmol) is added to a solution of Compound E (220 mg, 405 μmol) and 2-cyanoethanol (35 μl, 506 μmol) in tetrahydrofuran (4.1 ml) at 0° C. After stirring for 4 hours at room temperature, the reaction mixture is filtered and evaporated to give Compound G, a 1:1 mixture of diastereomers, as a viscous clear colorless oil.

$^{31}$P (162 MHz, CDCl$_3$) δ 37.79, 37.54 ppm.

Compound H

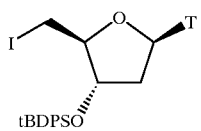

(T = 1-thyminyl)

This is prepared as described in WO 94/00467.

Compound I

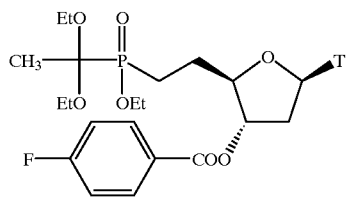

T = 1-thyminyl
Et-ethyl

To a solution of compound of formula

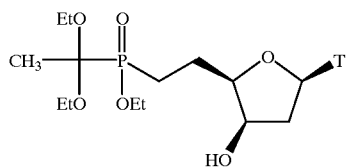

where T is 1-thyminyl and Et is ethyl, prepared as described in Example 1 of EP 0 614 907 (14.2 g, 32 mmol), triphenylphosphine (12.6 g, 48 mmol) and 4-fluorobenzoic acid (6.72 g, 48 mmol) in dry THF (200 ml) is added dropwise diethylazodicarboxylate (DEAD) (7.6 ml, 48 mmol) at 0° C. After 48 hours at room temperature the solvent is removed under vacuum and the residue purified by flash column chromatography on silica, eluting with ethyl acetate then 5% methanol, 95% ethyl acetate to give Compound I as a 1:1 mixture of diastereomers epimeric at phosphorus.

$^{31}$P (CDCl$_3$, 162 MHz,) δ 49.1, 48.9 ppm.

Compound J

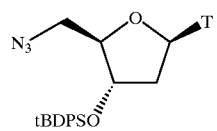

A solution of Compound H (6.05 g, 10.0 mmol) and sodium azide (3.25 g, 50.0 mmol) in DMF (50 ml) is heated at 85° C. for 5 hours. The crude reaction mixture is evaporated, taken-up in ethyl acetate (300 ml) and washed with water (3×100 ml). Evaporation of the dried organic phase gives Compound J.

Compound K

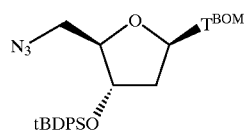

T$^{BOM}$ = N-benzyloxymethyl-1-thyminyl

To a solution of 5'-azido-3'-tert-butyidiphenyisilyloxythymidine (0.46 g, 0.91 mmol) DBU (272 μl, 1.82 mmol) in acetonitrile is added benzyloxymethyl chloride (214 mg, 1.37 mmol) at 0° C. After 18 hours at room temperature saturated aqueous sodium hydrogen carbonate solution (25 ml) is added. The aqueous layer is extracted with ethyl acetate and the organic extracts are dried over magnesium sulphate and evaporated. Purification of the crude product by silica gel chromatography, eluting with 19:1 dichloromethane:ethyl acetate, gives Compound K.

Compound L

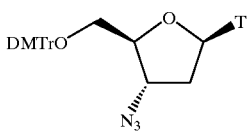

T = 1-thyminyl
DMTr = dimethoxytrityl

This is prepared as described by M. Mag, R. Schmidt and J. W. Engles, Tetrahedron Lett. 1992, 33, 7319–7322.

Compound M

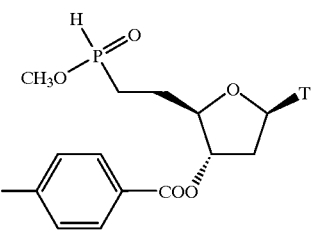

T = 1-thyminyl

The procedure used for the preparation of Compound D is repeated, replacing Compound C by Compound I (11.5 g, 20 mmol) and using 25.4 ml (200 mmol) of trimethylsilyl chloride, 90 ml of chloroform and 10 ml of ethanol instead of the amounts used in that preparation. The product is a compound of formula

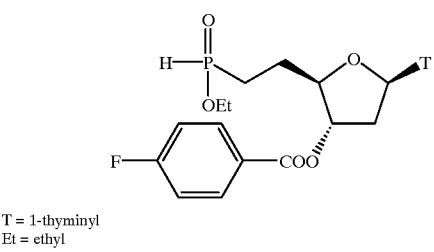

T = 1-thyminyl
Et = ethyl where T is 1-thyminyl and Et is ethyl obtained as 1:1 mixture of diastereomers, ($^{31}$P (CDCl$_3$, 162 MHz,) δ 37.4 ppm). This compound (7.34 g, 16.2 mmol) is used in place of Compound D in the procedure used for the preparation of Compound E, 32 ml of ethanol, 32 ml of triethylamine and 7.3 ml of water being used instead of the amounts used in that preparation. The product is a compound of formula

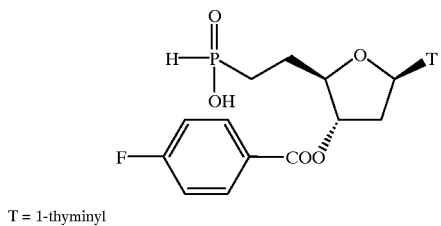

T = 1-thyminyl where T=1-thyminyl ($^{31}$P (d$_6$—DMSO, 162 MHz,) δ 31.1 ppm). This compound (6.16 g, 14.4 mmol) is used in place of Compound E in the procedure used for the preparation of Compound F, 640 μl (15.8 mmol) of methanol, 3.26 g (15.8 mmol) of dicyclohexylcarbodiimide, 5 mg of dimethylaminopyridine and 100 ml of tetrahydrofuran being used instead of the amounts used in that preparation. The product is a 1:1 mixture of diastereomers epimeric at phosphorus, Compound M.

$^{31}$P (CDCl$_3$, 162 MHz,) δ 40.3, 39.2 ppm

Compound N

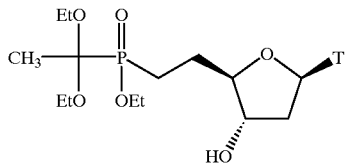

T = 1-thyminyl
Et = ethyl

To a solution of Compound I (6.0 g, 10.5 mmol) in ethanol (100 ml) is added a solution of sodium ethoxide in ethanol (6.8 mls, 21 wt % solution, 21.0 mmol) at room temperature. After 4 hours the reaction mixture is evaporated and purified by flash column chromatography on silica gel, eluting with 9:1 ethyl acetate/ethanol, giving Compound N as a 1:1 mixture of diastereomers.

$^{31}$P (CDCl$_3$, 162 MHz,) δ 50.02, 49.89 ppm

Compound O

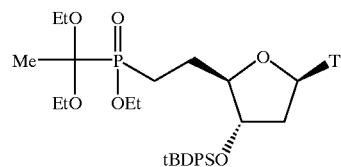

T = 1-thyminyl
Et = ethyl

To a solution of Compound N (1.46 g, 3.25 mmol) and imidazole (0.27 g, 3.90 mmol) in DMF (10 ml) is added tert-butyldiphenylsilylchloride (0.85 ml, 3.25 mmol) at 0° C. The reaction mixture is stirred for 18 hours at room temperature, drawn-out into saturated aqueous NaHCO$_3$, extracted with ethyl acetate and the organic layers are dried with sodium sulphate. Purification by flash column chromatography on silica gel, eluting with ethyl acetate, gives Compound O as a 1:1 mixture of diastereomers.

$^{31}$P (CDCl$_3$, 162 MHz,) δ 48.79, 48.64 ppm

Compound P

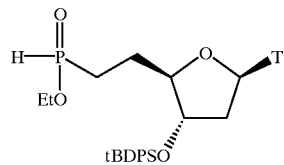

T = 1-thyminyl
Et = ethyl

The procedure used for the preparation of Compound D is repeated using Compound O (19.7 g, 28.7 mmol) in place of Compound C and using 36.4 ml (287 mmol) of trimethylsilylchloride, 20 ml of ethanol and 180 ml of chloroform instead of the amounts used in that Example, to give Compound P as a 1:1 mixture of diastereomers.

$^{31}$P (CDCl$_3$, 162 MHz,) δ 37.95, 37.64 ppm

Compound O

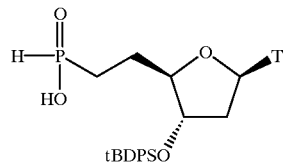

T = 1-thyminyl

A mixture of triethylamine (20 ml), ethanol (20 ml) and water (10 ml) is added to Compound P (6.0 g, 10.5 mmol) at room temperature giving a homogenous solution. After 18 hours at room temperature the reaction mixture is evaporated, then taken up into chloroform and washed with aqueous 1% HCl (2×25 ml) then water (25 ml). The organic layer is dried over sodium sulphate and evaporated to give Compound Q.

$^{31}$P (CDCl$_3$, 162 MHz,) δ 38.05 ppm

Compound R

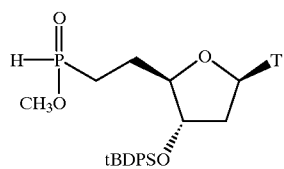

T = 1-thyminyl

To a solution of Compound Q (4.0 g, 7.37 mmol) and dimethylaminopyridine (10 mg) in methanol (896 μl, 22.1 mmol) and THF (50 ml) is added dicyclohexylcarbodiimide (DCC) (2.28 g, 11.1 mmol) at room temperature. After 18 hours at room temperature the reaction mixture is filtered, evaporated and purified by flash column chromatography on silica gel, eluting with ethyl acetate, to give Compound R as a 1:1 mixture of diastereomers.

$^{31}$P (CDCl$_3$, 162 MHz,) δ 40.77, 40.32 ppm

Compound S

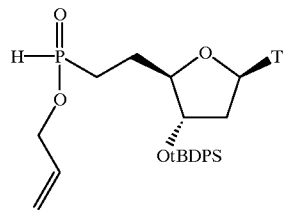

T = 1-thyminyl

The procedure used for the preparation of Compound R is repeated using allyl alcohol (2.4 ml, 35.2 mmol) in place of methanol and using 3.82 g (7.04 mmol) of Compound Q, 2.9 g (14.1 mmol) of DCC and 50 ml of DMF instead of the amounts used in that Example, to give Compound S as a 1:1 mixture of diastereomers.

$^{31}$P (CDCl$_3$, 162 MHz,) δ 38.35, 37.98 ppm

Found C, 60.71; H, 6.82; N, 4.82%; C$_{30}$H$_{39}$N$_2$O$_6$PSi.½H$_2$O requires C, 60.90; H, 6.81; N, 4.73%.

MS (ESP+) m/z 605 (M+Na).

Compound V

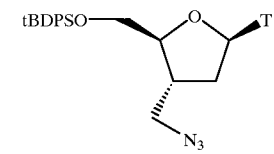

T = 1-thyminyl

To a solution of Compound B (11.5 g, 19 mmol) in dry DMF (100 ml) under argon is added sodium azide (6.18 g, 95 mmol). The resulting solution is stirred at 85° C. for 3 hours. Ethyl acetate is added (1000 ml) and the whole mixture washed with water. The organic phase is dried over magnesium sulphate and concentrated. Purification by vacuum flash silica chromatography (eluant: ethyl acetate-:pentane 1:1) gives Compound V.

Found C, 62.30; H, 6.50; N, 12.90%; C$_{27}$H$_{33}$N$_5$O$_4$Si requires C, 62.40; H, 6.40; N, 13.50%.

$^1$H NMR (CDCl$_3$, 400 MHz) δ 8.39 (1H, sbr, NH), 7.65 (4H, m, ArH), 7.44 (3H, m, ArH+H6), 7.38 (4H, m, ArH), 6.12 (1H, dd, J6 and 6 Hz H1'), 4.04 (1H, dd, J11.5 and 2.6 Hz, H5'), 3.85 (1H, m, H4'), 3.77 (1H, dd, J11.5 and 3.0 Hz. H5'), 3.35 (2H, d, J6.5 Hz, C H$_2$N$_3$), 2.65 (1H, m, H3'), 2.26 (1H, ddd, J13.8, 6 and 6 Hz, H2'), 2.18 (1H, ddd, J13.9, 9 and 5.5 Hz, H2'), 1.6 (3H, s, CH$_3$), 1.09 (9H, s, $^t$Bu) ppm.

MS (C.I NH$_3$) m/z 537.2 (MNH$_3^+$), 520.2 (M$^+$)

Compound W

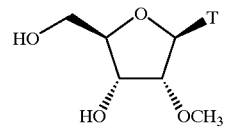

T = 1-thyminyl

The above compound is prepared as described by P. Martin Helv. Chin. Acta (1995), 78(2), 486–504 or B. S. Ross, R. H. Springer, G. Vasquez, R. S. Andrews, P. D. Cook, O. L. Acevedo. J. Heterocyclic Chem. (1994), 31(4), 765.

Compound X

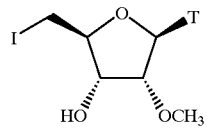

T = 1-thyminyl

To a solution of triphenylphosphine (8.26 g, 31.5 mmol) in dry pyridine (122 ml) at 0° C. under argon is added iodine (8.00 g, 31.5 mmol). The resulting solution is stirred until all the iodine has dissolved. To the resulting mixture is added Compound W (8.17 g, 30.0 mmol) and the mixture allowed to warm to room temperature. After 20 hours, the solution is concentrated, dissolved in ethyl acetate (200 ml) and washed with water and brine. The aqueous phase is back extracted with ethyl acetate. The combined organic phase is dried over Na$_2$SO$_4$ and concentrated to give crude Compound X which is used directly in the preparation of Compound Y.

$^1$H NMR (CDCl$_3$, 400 MHz) δ 5.90 (1H, d, H1') 4.00 (1H, dd, H3'), 3.80 (1H, m, H4'), 3.63 (1H, m, H2') 3.60 (1H, dd, H5'), 3.55 (3H, s, OMe) 3.45 (1H, dd, H5') 1.93 (1H, s, CH$_3$)ppm.

Compound Y

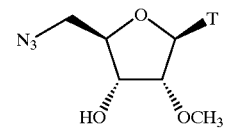

T = 1-thyminyl

To a solution of the crude Compound X prepared as described above in dry DMF (155 ml) under argon is added soldium azide (9.75 g, 0.15 mol) and the reaction mixture heated with stirring at 70° C. for 2.5 hours. The resulting mixture is cooled to room temperature and filtered. The resulting solution is concentrated under high vacuum, redissolved in chloroform and refiltered. Concentration and purification by flash silica column chromatography (eluant, chloroform:ethanol 20:1) gives Compound Y.

Found C, 44.05; H, 5.25; N, 22.90%; C$_{11}$H$_{15}$N$_5$O$_5$.¼H$_2$O requires C, 43.80; H, 5.20; N, 23.20%.

$^1$H NMR (CDCl$_3$, 400 MHz) δ 8.80 (1H, sbr, NH) 7.41 (1H,s, H6), 5.90 (1H, d, H1'), 4.17 (1H, m, H3') 3.98 (1H, ddd, H4'), 3.83 (1H, dd, H5') 3.79 (1H, dd, H2') 3.65 (1H, dd, H5') 3.58 (3H, s, OMe), 2.74 (1H, d, OH) 1.92 (3H, s, CH₃) ppm.

Compound Z

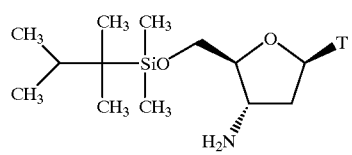

T = 1-thyminyl

This is prepared as described by M. Maillard, A. Faraj, F. Frappier, J. C. Florent, D. S. Grierson and C. Monnerat, Tetrahedron Lett. (1989), 30, 1955.

Compound ZA

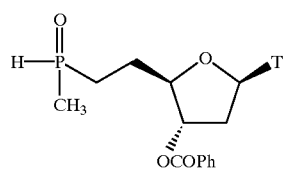

T = 1-thyminyl

This is prepared as described in Example 24 of EP 0 629 633.

Compound ZB

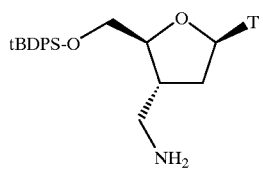

T = 1-thyminyl

This is prepared as described by J. Lebreton, A. Waldner, V. Fritsch, R. Wolff, A. DeMesmaeker, Tetrahedron Lett (1994), 35, 5225.

Compound ZD

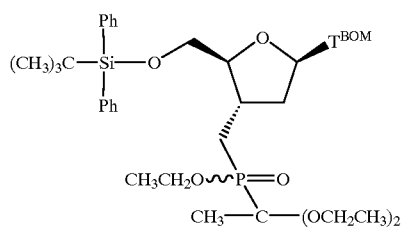

Ph = phenyl
T$^{BOM}$ = N-benzyloxlmethyl-1-thyminyl

Benzyl chloromethyl ether (173 µl, 1.1 mmol) is added dropwise to a solution of Compound C (380 mg, 553 µmol) and 1,8-diazabicyclo[5.4.0]undec-7-ene (DBU) (145 µl, 968 µmol) in acetonitrile (11 ml) at 0° C. After stirring for 2 hours at room temperature, saturated aqueous sodium hydrogen carbonate (20 ml) is added and the aqueous layer extracted with (3×20 ml) ethyl acetate. Drying of the organic extacts over magnesium sulphate and evaporation yields the crude product. Purification via flash column chromatography on silica, eluting with 98% dichoromethane, 2% methanol, gives Compound ZD, a 1:1 mixture of diastereomers, as a viscous clear colorless oil.

Compound ZE

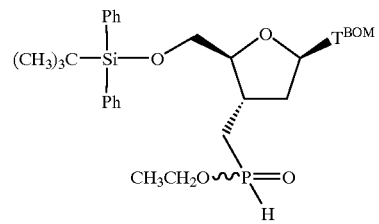

Ph = phenyl
T$^{BOM}$ = N-benzyloxlmethyl-1-thyminyl

Trimethylchlorosilane (613 µl, 4.83 mmol) is added dropwise at 0° C. to a solution of Compound ZD (390 mg, 483 µmol) in chloroform (3.4 ml) containing ethanol (10%) under argon. After stirring for 18 hours at room temperature, saturated aqueous sodium hydrogen carbonate (20 ml) is added, the aqueous layer is extracted with dichloromethane (1×20, 2×10 ml) and the organic extracts dried over magnesium sulphate. Evaporation gives the crude product which is purified by flash column chromatography on silica, eluting with 95% dichloromethane, 5% methanol, to give Compound ZE, a 1:1 mixture of diastereomers, as a viscous clear colorless oil.

Compound ZF

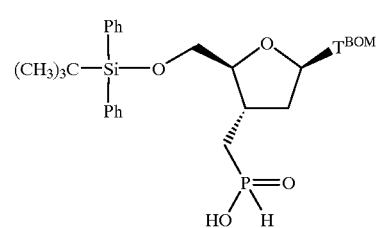

Ph = phenyl
T$^{BOM}$ = N-benzyloxymethyl-1-thyminyl

A solution of Compound ZE (0.29 g, 420 µmol) in ethanol (1.7 ml), water (0.8 ml) and triethylamine (1.7 ml) is stirred at room temperature for 4 hours. After dilution with ethyl acetate (30 ml), the reaction mixture is washed with cold 0.05 M aqueous HCl (2×20 ml), then water (2×20 ml) and dried over magnesium sulphate. Evaporation yields Compound ZF as a viscous clear colorless oil.

$^{31}$P (162 MHz, CDCl₃) δ 35.62 ppm.

Compound ZG

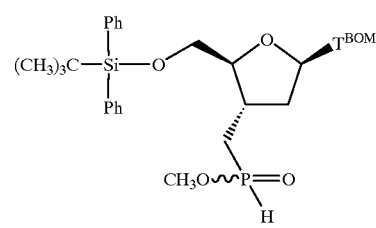

Ph = phenyl
T$^{BOM}$ = N-benzyloxymethy1-1-thyminyl

Dicyclohexylcarbodiimide (105 mg, 509 µmol) is added to a solution of Compound ZF (270 mg, 407 µmol), 2,6-dimethyl-4-aminopyridine (0.6 mg, 5 µmol) and methanol (21 µl, 509 µmol) in tetrahydrofuran (4.1 ml) at 0° C. After stirring for 3 hours at room temperature, the reaction mixture is evaporated. Flash column chromatography of the evaporation residue on silica, eluting with 95% ethyl acetate, 5% methanol yields Compound ZG, a 1:1 mixture of diastereomers, as a viscous clear colorless oil.

$^{31}$P (162 MHz, CDCl$_3$) δ 37.37, 37.08 ppm.

Compound ZH

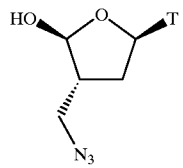

To a solution of compound V (1.25 g, 2.41 mmol) in THF (30 ml) under argon is added a 1 molar solution of tetra n-butylammoniumfluoride (2.65 ml) in THF. The mixture is stood at rt for 1 h and then at 5° C. for 60 h. A further portion of tetra n-butylammoniumfluoride (0.65 ml) solution is then added. After stirring for an additional 1 hour at rt the mixture is concentrated in vacuum and purified by flash silica column chromatography (eluant ethyl acetate: methanol 97.5:2.5) to give compound ZH as a white foam.

$^1$H NMR (CDCl$_3$, 400 MHz) δ 9.00 (1H, sbr, NH), 7.50 (1H, s, H6), 6.05 (I H, t, H1'), 4.00 (1H, dd, H5'), 3.90 (1H, m, H4'), 3.80 (1H, dd, H5'), 3.50 (1H, dd, H6'), 3.45 (1H, dd, H6'), 2.65 (1H, m, H3'), 2.25 (2H, m, 2× H2'), 1.90 (3H, s, CH$_3$) ppm.

Compound ZJ

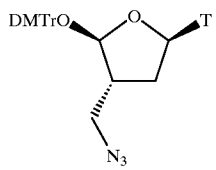

Compound ZH (1.62 g, 5.76 mmol) is dried by coevaporation from dry pyridine. To a solution of compound ZH in pyridine (20 ml) is added dimethoxytrityl chloride (2.93 g, 8.64 mmol). The resulting mixture is stood at room temperature for 60 h and is then concentrated under vacuum. The oily solid is dissolved in CH$_2$Cl$_2$ (50 ml) and washed with 10% NaHCO$_3$ (30 ml) and brine (30 ml), dried over Na$_2$SO$_4$ and concentrated. Purification by flash silica column chromatography (eluant chloroform:methanol:triethylamine 98.5:1:0.5) gives compound ZJ.

$^1$H NMR (CDCl$_3$, 400 MHz) δ 8.10 (1H, sbr, NH), 7.65 (1H, s, H6), 7.40 (2H, d, ArH), 7.30 (7H, m, ArH), 6.80 (4H, d, ArH), 6.10 (1H, t, H1'), 3.90 (1H, m, H4'), 3.55 (1H, dd, H5'), 3.35 (2H, m, H6'), 3.25 (1H, dd, H5'), 2.65 (1H, m, H3'), 2.25 (2H, m, H2'), 1.50 (3H, s, CH$_3$) ppm.

Compound ZKA

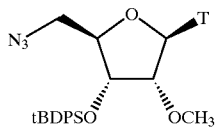

Compound ZKA is prepared by the general procedure used for Compound O using Compound Y (6.75 g, 22.7 mol) in place of Compound N and using modified quantities of reagents; imidazole (2.32 g, 34 mmol), DMF (13 ml) and tert-butyidiphenylsilylchloride (7.55 ml, 29.5 mmol). Purification by flash silica column chromatography on silica gel, eluting with chloroform-ethanol mixtures gives Compound ZKA.

$^1$H NMR (CDCl$_3$, 500 MHz) δ 8.05 (1H, brs, NH), 7.65 (2H, d, ArH), 7.60 (2H, d, ArH), 7.40 (2H, m, ArH), 7.35 (4H, m, ArH), 7.10 (1H, s, H6), 5.80 (1H, d, H1'), 4.1 (1H, m, H4'), 3.95 (1H, dd, H3'), 3.60 (1H, dd, H5'), 3.25 (1H, dd, H5'), 3.20 (3H, s, OCH$_3$), 3.15 (1H, dd H2'), 1.80 (3H, s, CH$_3$), 1.05 (9H, s, tBu) ppm.

Compound ZK

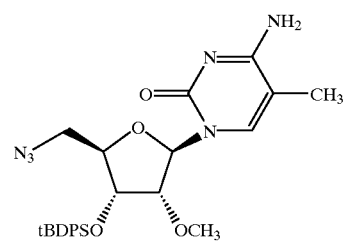

To a solution of 1,2,4triazole (8.23 g, 0.12 mol) in dry pyridine (80 ml) under argon at 0° C. is added triethylamine (16.73 ml, 0.12 mol) followed by the dropwise addition of phosphorusoxy chloride (2.75 ml, 0.03 mol). After stirring at 0° C. for 10 min a solution of Compound ZKA (6.43 g, 0.12 mmol) in pyridine (30 ml) is added dropwise and the mixture is washed with further pyridine (30 ml). The resulting solution is stirred for 30 mins at 0° C. and 18 h at rt. Concentration then gives a thick oil which is dissolved in dichloromethane and washed with saturated sodium bicarbonate and brine dried over magnesium sulphate and concentrated. The crude material is dissolved in dry THF (100 ml) and conc ammonia slowly added (35 ml). After stirring at rt for 24 h concentration and purification by flash silica column chromatography (gradient elution ethyl acetate-ethanol 20:1–7:1) gives Compound ZK.

Found C, 59.70; H, 6.45; N, 16.05%; C$_{27}$H$_{34}$N$_6$O$_4$Si½H$_2$O requires C, 59.65; H, 6.50; N, 15.45%.

MS (E.I) M/Z 535.1 (MH$^+$).

Compound ZL

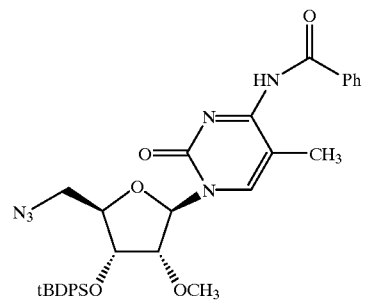

To a solution of carefully dried Compound ZK (6.04 g, 11.3 mmol) under argon in diethylether (113 ml) is added triethylamine (4.73 ml, 33.9 mmol) at 0–5° C. The resulting solution is allowed to warm to rt and is stirred for 16 h before pouring onto water. The layers are separated and the organic layer is further washed with water and brine, dried over magnesium sulphate and concentrated. Purification by flash silica column chromatography (gradient elution chloroform—chloroform:methanol 10:1) gives Compound ZL.

Found C, 61.60; H, 5.85; N, 12.50%; $C_{34}H_{38}N_6O_5Si\cdot\frac{3}{2}H_2O$ requires C, 61.35; H, 6.20; N, 12.60%.

$^1$H NMR (CDCl$_3$, 400 MHz) δ 13.2 (1H, sbr, NH), 8.35 (2H, d, Ar), 7.70 (2H, d, Ar), 7.65 (2H, d, Ar), 7.50 (1H, m, Ar), 7.40 (9H, m, Ar+H6), 5.90 (1H, d, H1'), 4.20 (1H, m, H4'), 4.00 (1H, m, H3'), 3.75 (1H, dd, H5'), 3.40 (1H, dd, H5'), 3.35 (3H, s, OCH 3), 3.20 (1H, m, H2'), 2.05 (3H, s, CH$_3$), 1.10 (9H, s, tBu) ppm.

Compound ZM

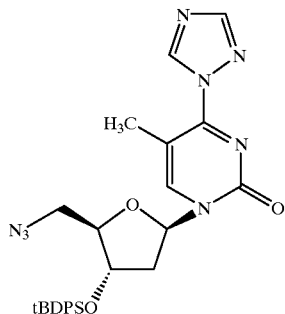

To a solution of Compound J (4.92 g, 9.73 mmol) and triazole (6.72 g, 9.73 mmol) in triethylamine (16.3 ml) and pyridine (100 ml) is added phosphorus oxychloride (2.23 ml, 24.3 mmol) at 0° C. The reaction is stirred at room temperature for 18 hours, partitioned between aqueous sodium hydrogen carbonate and dichloromethane, and the organic layers dried over magnesium. The product is purified by flash column chromatography on silica gel, eluting with ethyl acetate to give Compound ZM.

Found C, 59.87; H, 5.85; N, 19.53%; $C_{28}H_{32}N_8O_3Si$ requires C, 60.41; H, 5.79; N, 20.13%.

MS (ES) M/Z 557 (MH$^+$), 579 (MNa$^+$).

Compound ZN

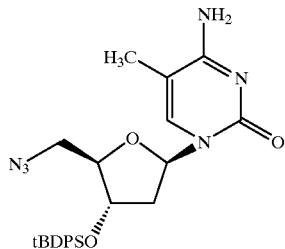

To Compound ZM (4.4 g, 7.90 mmol) is added 1,4-dioxane (50 ml) and 880 ammonia solution (50 ml) at room temperature. After 24 hours at room temperature the reaction mixture is evaporated and the crude product purified by flash column chromatography on silica gel eluting with a gradient from ethyl acetate to 90% ethyl acetate 10% methanol to give Compound ZN.

MS (ES) M/Z 505 (MH$^+$), 527 (MNa$^+$).

Compound ZO

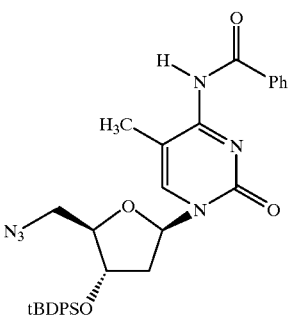

To a solution of Compound ZN (737 mg, 1.46 mmol) and triethylamine (1.02 ml, 7.30 mmol) in diethylether (15 ml) is added benzoyl chloride (0.51 ml, 4.38 mmol) at 0° C. The white suspension is stirred at room temperature for 4 hours, partitioned between aqueous sodium hydrogen carbonate and ethyl acetate, and the ethyl acetate layers dried over magnesium sulphate and evaporated. The crude product is purified by flash column chromatography on silica gel eluting with a gradient from chloroform to 95% chloroform 5% ethyl acetate to give Compound ZO as a colorless viscous oil.

Found C, 65.05; H, 5.97; N, 13.48%; $C_{33}H_{36}N_6O_4Si$ requires C, 65.11; H, 5.96; N, 13.80%.

MS (ES) M/Z 609 (MH$^+$), 631 (MNa$^+$).

Compound ZP

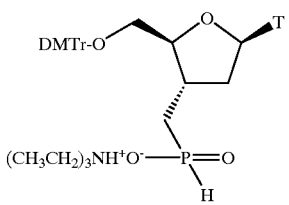

This is prepared as described in Example 85 of WO 96/08503.

Compound ZQ

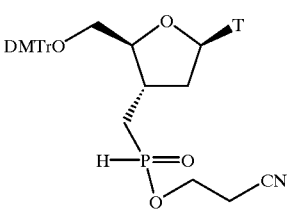

To a solution ZP (500 mg, 0.71 mmol) and dicyclohexylcarbodiimide (189 mg, 0.92 mmol) in dry THF (5.4 ml) under argon at room temperature is added 3-hydroxy propionitrile (58 μl, 0.85 mmol). The resulting solution is heated at 55° C. for 2 hours. After cooling, the mixture is filtered and diluted with ethyl acetate (20 ml) and washed with water and brine, dried over Na$_2$SO$_4$, filtered and concentrated. The resulting product is taken up in dichloromethane (5 ml) and filtered and concentrated, this process being repeated as required to remove dicyclohexyl urea, to give Compound ZQ, isolated as a mixture of diastereoisomers at phosphorus.

Compound ZR

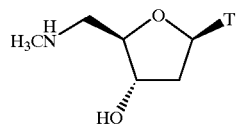

A solution of 5'-deoxy-5'-iodo-thymidine prepared following the procedure of McElroy and Widlanski, J. Org. Chem. 1994, 59, 3520–3521, (2.75 g, 7.81 mmol) in a 2.0M solution of methylamine in tetrahydrofuran (30 ml) is stirred at room temperature. After six hours the reaction mixture is evaporated and purified by ion exchange chromatography to give Compound ZR.

Compound ZS

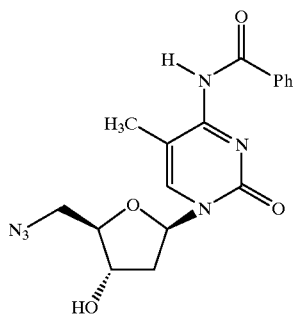

To a solution of Compound ZO (2.0 g, 3.29 mmol) in THF (3.8 ml) is added 3.94 mls of a 1.0M TBAF in THF solution (3.94 mmol) at 0° C. After 2 hours the reaction mixture is evaporated and the crude product purified by flash column chromatography on silica gel eluting with 98% chloroform 2% ethanol to give Compound ZS.

Compound ZT

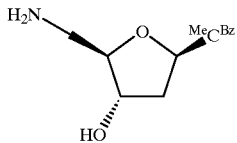

A suspension of 10% palladium on carbon (177 mg) in a solution of Compound ZS (3.54 g, 9.56 mmol) in methanol (200 ml) is stirred for 2 hours under an atmosphere of hydrogen at room temperature. Filtration and evaporation gives Compound ZT.

Found C, 57.26; H, 5.86; N, 15.96%; $C_{17}H_{20}N_4O_4 \cdot 0.5H_2O$ requires C, 57.78; H, 5.98; N, 15.85%.

EXAMPLE 1

Compound 1

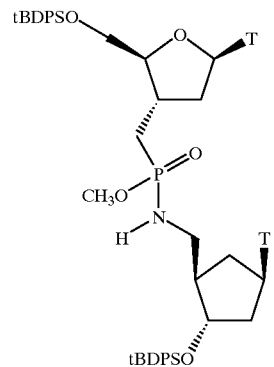

T = 1-thyminyl

To a solution of Compound J (1.17 g, 2.32 mmol) and Compound F (1.29 g, 2.32 mmol) in pyridine (23 ml) is added bistrimethylsilyl trifluoroacetamide (BSTFA) (2.28 ml, 10.4 mmol) at 0° C. After 18 hours methanol (30 ml) is added, the reaction mixture is then evaporated, taken-up into a mixture of chloroform (40 ml) and methanol (10 ml) and heated to reflux. After 8 hours reflux the reaction mixture is evaporated then purified by silica gel column chromatography eluting with 19:1 chloroform/methanol to give Compound 1 as a mixture of diastereoisomers.

$^{31}$P NMR (CDCl$_3$, 162 MHz) δ33.6, 32.9 ppm.

MS (ES, HCOOH) m/z 1035 (MH$^+$), 908 (loss T)

EXAMPLE 2

Compound 2

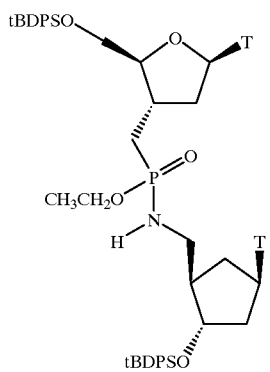

T = 1-thyminyl

Example 1 is repeated using Compound D (2.6 g, 4.50 mmol) in place of Compound F and using 2.53 g (4.95 mmol) of Compound J, 6 ml (22.5 mmol) of BSTFA, and 23 ml of pyridine instead of the amounts used in Example 1.

Compound 2 is obtained as a mixture of diastereoisomers.

$^{31}$P NMR (CDCl$_3$, 162 MHz) δ32.3, 31.6 ppm.

EXAMPLE 3

Compound 3

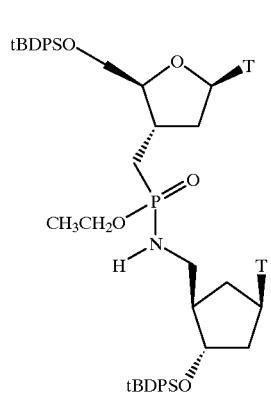

T = 1-thyminyl

Example 1 is repeated using Compound $D_1$(361 mg, 632 µmol) in place of Compound F and using 336 mg (664 µmol) of Compound J, 754 µl (2.84 mmol) of BSTFA, and 6.3 ml of pyridine instead of the amounts used in Example 1. Compound 3 is obtained as a single diastereoisomer.

$^{31}$P NMR (CDCl$_3$, 162 MHz) δ 32.2 ppm.

EXAMPLE 4

Compound 4

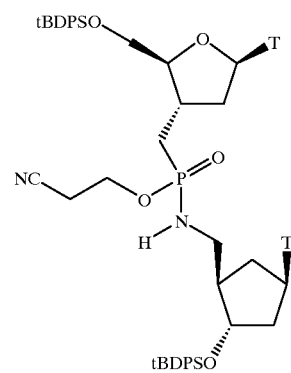

T = 1-thyminyl

Example 1 is repeated using Compound G (241 mg, 405 µmol) in place of Compound F and using 225 mg (446 µmol) of Compound J, 537 µl (2.03 mmol) of BSTFA and 4.1 ml of pyridine instead of the amounts used in Example 1. Compound 4 is isolated as a mixture of diastereoisomers.

$^{31}$P NMR (CDCl$_3$, 162 MHz) δ 34.2, 33.2 ppm.

MS (ES, HCOOH) m/z 1074 (MH$^+$), 948 (loss T)

Found C, 61.18; H, 6.55; N, 7.56; $C_{56}H_{69}N_6O_{10}PSi_2.H_2O$ requires C, 61.63; H, 6.56; N, 7.70.

EXAMPLE 5

Compound 5

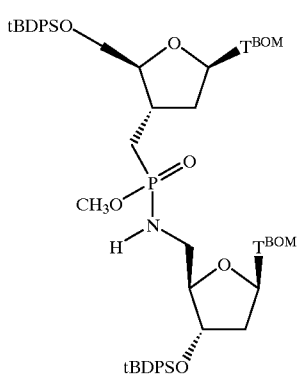

$T^{BOM}$ = N-benzyloxymethyl-1-thyminyl

To a solution of Compound 1 (2.09 g, 2.02 mmol) and 1,8-diazabicyclo[5.4.0]undec-7-ene (DBU) (2.4 ml, 16.2 mmol) in acetonitrile (61 ml) is added benzyloxymethyl chloride (0.95 g, 6.06 mmol), at 0° C. After 3 hours at 0° C. saturated aqueous NaHCO$_3$(120 ml) is added, the aqueous phase is extracted with ethylacetate and the organic layers are dried and evaporated. The residue is purified by silica gel column chromatography, eluting with ethyl acetate to give Compound 5.

$^{31}$P NMR (CDCl$_3$, 162 MHz) δ 33.3, 32.9 ppm.

MS (ES, HCOOH) m/z 1275 (MH$^+$), 783 (loss T$^{bom}$).

Found C, 63.74; H, 6.49; N, 5.57; $C_{70}H_{64}N_5O_{12}PSi_2.H_2O$ requires C, 64.15; H, 6.77; N, 5.34.

EXAMPLE 6

Compound 6

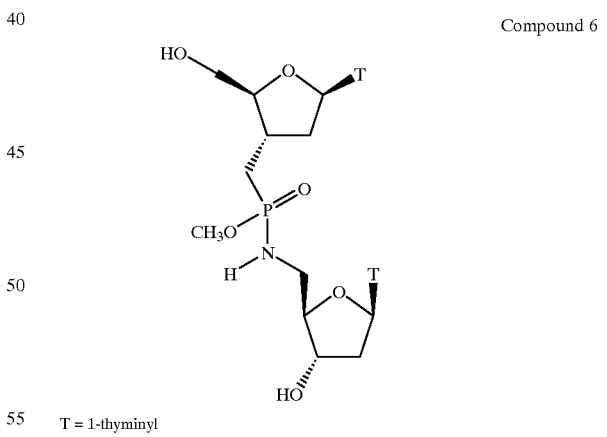

T = 1-thyminyl

To a solution of Compound 1 (360 mg, 348 µmol) in THF (7 ml) is added a solution of tetra-n-butyl-ammonium fluoride (TBAF) in THF (1.0M solution, 766 µl) at 0° C. After 2 hours at 0° C. the reaction mixture is applied to a silica gel column and eluted with chloroform, then 3:1 chloroform/methanol, to give Compound 6.

$^{31}$P NMR (d$_4$-methanol, 162 MHz) δ 41.20, 41.18 ppm.

MS (ES, HCOOH) m/z 558 (MH$^+$), 432 (loss T).

EXAMPLE 7

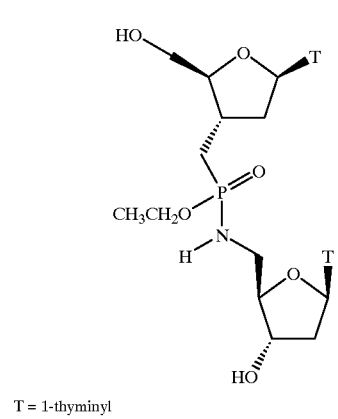

Compound 7

T = 1-thyminyl

Example 6 is repeated using Compound 2 (256 mg, 240 μmol) in place of Compound 1 and using 3 ml of THF and 730 μl of the 1.0 M TBAF solution instead of the amounts used in Example 6. The product is Compound 7 as a 1:1 mixture of diastereomers.

$^{31}$P NMR (CD$_3$OD, 162 MHz) δ 34.9 ppm.

EXAMPLE 8

Compound 8

T = 1-thyminyl

Example 6 is repeated using Compound 3 (345 mg, 329 μmol) in place of Compound 1 and using 6 ml of THF and 987 μl (987 μmol) of the 1.0M TBAF solution instead of the amounts used in Example 6. The product is Compound 8, isolated as a single diastereoisomer.

$^{31}$P NMR (CD$_3$OD, 162 MHz) δ 36.4 ppm.

EXAMPLE 9

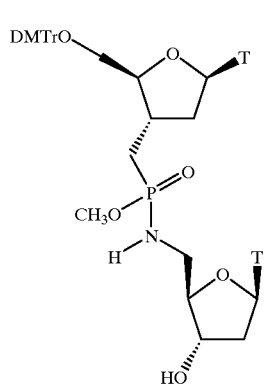

Compound 9

T = 1-thyminyl
DMTr = dimethoxytrityl

To a solution of Compound 6 (128 mg, 230 μmol) in pyridine (2.3 ml) is added dimethoxytrityl chloride (117 mg, 344 μmol) at 0° C. After 3 hours at room temperature, methanol (1 ml) is added and the reaction mixture evaporated. The residue is purified by silica gel column chromatography, eluting with 9:1 chloroform/methanol containing 0.25% triethylamine, to give Compound 9.

$^{31}$P NMR (CDCl$_3$, 162 MHz) δ 34.52, 34.44 ppm.

EXAMPLE 10

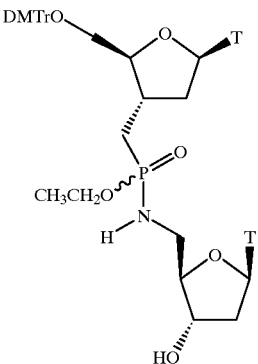

Compound 10

T = 1-thyminyl
DMTr = dimethoxytrityl

Example 9 is repeated using Compound 7 (150 mg, 260 μmol) in place of Compound 6 and using 133 mg (390 μmol) of dimethoxytrityl chloride and 5 ml of pyridine instead of the amounts used in Example 9. The product is a 1:1 mixture of diastereomers that is separated by flash column chromatography on silica gel, eluting with 10:1 chloroform/ethanol containing 0.25% triethylamine to give the higher Rf isomer A followed by the lower Rf isomer B.

Isomer A: $^{31}$P NMR (CDCl$_3$, 162 MHz) δ 33.3 ppm.

Isomer B: $^{31}$P NMR (CDCl$_3$, 162 MHz) δ 33.2 ppm.

Example 9 is repeated using Compound 8 (146 mg, 255 μmol) in place of Compound 6 and using 129 mg (383 μmol) of dimethoxytrityl chloride and 2.6 ml of pyridine instead of the amounts used in Example 9. The product is lower Rf diastereomer B.

EXAMPLE 11

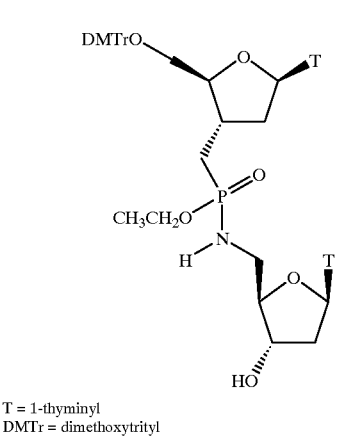

Compound 11

T = 1-thyminyl
DMTr = dimethoxytrityl

Example 9 is repeated using Compound 8 (146 mg, 255 μmol) in place of Compound 6 and using 129 mg (383 μmol) of dimethoxytrityl chloride and 2.6 ml of pyridine instead of the amounts used in Example 9. The product is Compound 11, isolated as a single diastereoisomer.

$^{31}$P NMR (CDCl$_3$, 162 MHz) δ 33.1 ppm.

EXAMPLE 12

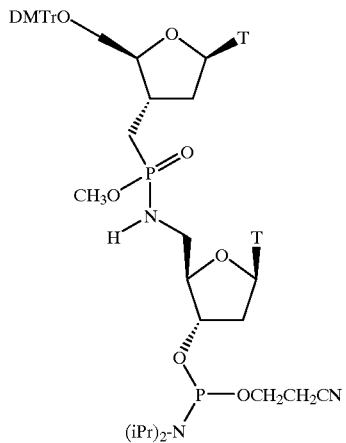

Compound 12

T = 1-thyminyl
DMTr = dimethoxytrityl
iPr = isopropyl

To a solution of Compound 9 (198 mg, 230 μmol) and diisopropylammonium tetrazolide (197 mg, 1.15 mmol) in dichloromethane (6.9 ml) is added 2-cyanoethyl bis-(N,N-diisopropyl)-phosphordiamidite (208 mg, 690 μmol) at 0° C. After 18 hours at room temperature saturated aqueous sodium bicarbonate solution (10 ml) is added and the mixture extracted with dichloromethane. The dichloromethane extracts are dried over magnesium sulphate and evaporated. The crude product is purified by silica gel column chromatography eluting with 15:1 chloroform/methanol containing 0.25% triethylamine to give Compound 12.

$^{31}$P NMR (CDCl$_3$, 162 MHz) δ 150.08, 149.92, 149.32, 149.25, 34.02, 33.95, 33.46, 33.42 ppm.

Found C, 56.93; H, 6.29; N, 8.92; C$_{52}$H$_{67}$N$_7$O$_{13}$P$_2$.2H$_2$O requires C, 56.98; H, 6.53; N, 8.94.

EXAMPLE 13

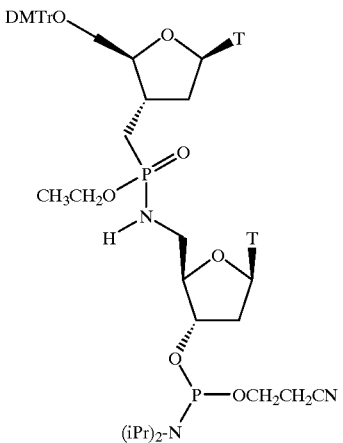

Compound 13

T = 1-thyminyl
DMTr = dimethoxytrityl
iPr = isopropyl

Example 12 is repeated using diastereoisomer A of Compound 10 (100 mg, 110 μmol) in place of Compound 9 and using 98 mg (550 μmol) of diisopropylammonium tetrazolide and 103 mg (330 μmol) of 2-cyanoethyl bis-(N,N-diisopropyl)-phosphordiamidite in place of the amounts used in Example 12. The product is Compound 13 as a 1:1 mixture of diastereomers.

$^{31}$P NMR (CDCl$_3$, 162 MHz) δ 149.9, 142.2, 31.6, 31.5, ppm.

EXAMPLE 14

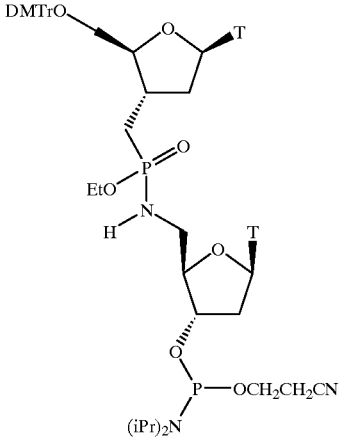

Compound 14

T = 1-thyminyl
DMTr = dimethoxytrityl
iPr = isopropyl

Example 12 is repeated using Compound 11 (0.55 g, 630 μmol) in place of Compound 9 and using 0.54 g (3.1 mmol) of diisopropylammonium tetrazolide and 0.57 g (1.8 mmol) of 2-cyanoethyl bis-(diisopropylamino)-phosphordiamidite in place of the amounts used in Example 12. The product is Compound 14 as a 1:1 mixture of diastereomers.

$^{31}$P NMR (CDCl$_3$, 162 MHz) 3150.1, 149.3, 32.3, 32.2 ppm.

EXAMPLE 15

Compounds 15A and 15B

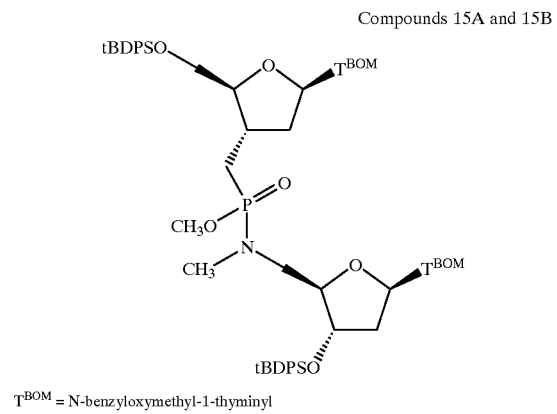

T^BOM = N-benzyloxymethyl-1-thyminyl

To a solution of Compound 5 (1.88 g, 1.47 mmol) in toluene (15 ml) is added sodium hydride (0.18 g, 7.37 mmol) at room temperature. After 15 minutes iodomethane (9.2 ml, 147 mmol) is added and the reaction mixture heated to 40° C. in a sealed bomb. After 3 days at 40° C. the reaction mixture is quenched with water (200 ml) then extracted with ethyl acetate. The ethyl acetate extracts are dried over magnesium sulphate, then evaporated. The crude product is purified by silica gel column chromatography, eluting with ethyl acetate to give first Compound 15A and then Compound 15B as separate diastereomers.

Compound 15A=$^{31}$P NMR (CDCl$_3$, 162 MHz) δ 34.2 ppm

Compound 15B=$^{31}$P NMR (CDCl$_3$, 162 MHz) δ 35.5 ppm

Compound 15A MS (ES, HCOOH) m/z 1289 (MH$^+$), 1043 (loss T$^{BOM}$).

Compound 15B MS (ES, HCOOH) m/z 1289 (MH$^+$), 1043 (loss T$^{BOM}$).

1:1 mixture of compounds 15A and 15B Found C, 65.63; H, 6.83; N, 5.23; C$_{71}$H$_{86}$N$_5$O$_{12}$PSi$_2$.H$_2$O requires C, 65.26; H, 6.79; N, 5.36.

EXAMPLE 16

Compound 16A

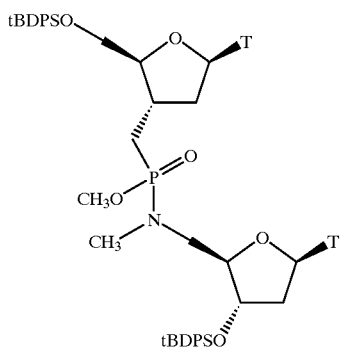

To a solution of Compound 15A (1.74 g, 1.35 mmol) in ethanol (34 ml) is added 10% palladium on carbon (120 mg) at room temperature. An atmosphere of hydrogen is introduced and the reaction mixture is stirred for 18 hours, then filtered and evaporated. The crude product is purified by flash column chromatography eluting with ethyl acetate to give Compound 16A as a single diastereomer.

$^{31}$P NMR (CDCl$_3$, 162 MHz) δ 34.3 ppm

MS (ES, HCOOH) m/z 1049 (MH$^+$), 923 (loss T).

EXAMPLE 17

Compound 17

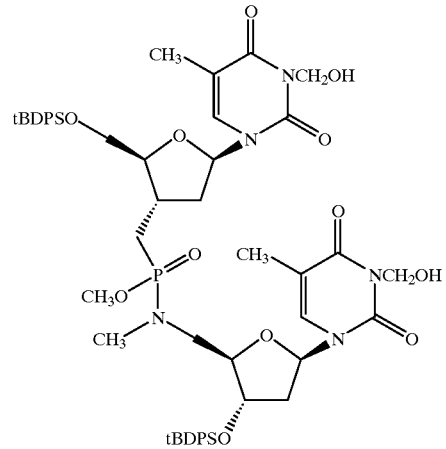

To a solution of Compound 15A (1.14 g, 885 μmol) in methanol (30 ml) and ethanol (10 ml) is added palladium hydroxide on carbon (100 mg) at room temperature. An atmosphere of hydrogen is introduced and the reaction mixture is stirred for 18 hours at room temperature, then filtered, giving a solution of Compound 17.

Sodium methoxide (20 mg) is added to the solution of Compound 17 at room temperature. After 3 hours acetic acid (500 μm) is added and the reaction mixture evaporated, then purified by flash column chromatography, eluting with ethyl acetate, to give Compound 16A.

EXAMPLE 18

Compound 16B

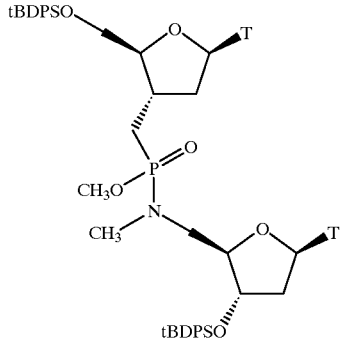

T = 1-thyminyl

Example 17 is repeated using Compound 15B (1.14 g, 885 μmol) in place of Compound 11 and using 100 mg of palladium hydroxide on carbon in 30 ml ethanol instead of the amounts used in Example 17. The product is Compound 16B as a single diastereomer.

$^{31}$P NMR (CDCl$_3$, 162 MHz) δ 35.7 ppm

MS (ES, HCOOH) m/z 1049 (MH$^+$), 923 (loss T).

Found C, 60.86; H, 6.88; N, 6.18; C$_{55}$H$_{70}$N$_5$O$_{10}$PSi$_2$.2H$_2$O requires C, 60.92; H, 6.88; N, 6.46.

EXAMPLE 19

Compounds 18A and 18B

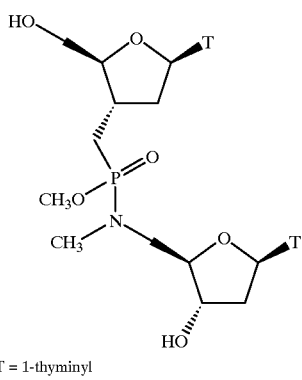

T = 1-thyminyl

The procedure of Example 6 is repeated using Compound 16A (1.42 g, 1.35 mmol) in place of Compound 1 and using 2.97 ml (2.97 mmol) of the TBAF/THF solution and 27 ml of THF instead of the amounts used in that Example, to give Compound 18A as a single diastereomer.

$^{31}$P NMR (CDCl$_3$, 202 MHz) δ38.6 ppm

The procedure of Example 6 is repeated using Compound 16B (928 mg, 885 μmol) in place of Compound 1 and using (1.95 ml, 1.95 mmol) of TBAF/THF solution and 18 ml of THF instead of the amounts used in that Example, to give Compound 18B as a single diastereomer.

$^{31}$P NMR (CD$_3$OD, 202 MHz) δ 38.8 ppm

EXAMPLE 20

Compounds 19A and 19B

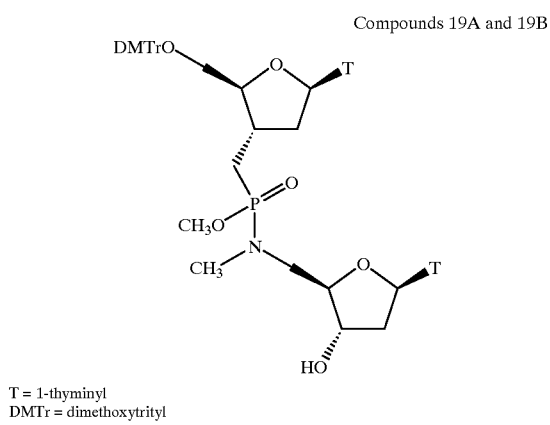

T = 1-thyminyl
DMTr = dimethoxytrityl

The procedure of Example 9 is repeated using Compound 18A (0.77 g, 1.35 mmol) in place of Compound 6 and using 0.69 g (2.03 mmol) of dimethoxytritylchloride and 14 ml of pyridine instead of the amounts used in that Example, to give Compound 19A as a single diastereomer.

$^{31}$P NMR (CD$_3$OD, 162 MHz) δ 41.4 ppm

Found C, 59.29; H, 6.36; N, 7.90; C$_{44}$H$_{52}$N$_5$O$_{12}$P.H$_2$O requires C, 59.25; H, 6.10; N, 7.85.

The procedure of Example 9 is repeated using Compound 18B (0.51 mg, 0.89 mmol) in place of Compound 6 and using 525 mg (1.55 mmol) of dimethoxytrityichlonde and 9 ml of pyridine instead of the amounts used in that Example, to give Compound 19B as s single diastereomer.

$^{31}$P NMR (CD$_3$OD, 162 MHz) δ 38.7 ppm

Found C, 59.16; H, 6.25; N, 7.62; C$_{44}$H$_{52}$N$_5$O$_{12}$P.H$_2$O requires C, 59.25; H, 6.10; N, 7.85.

EXAMPLE 21

Compounds 20A and 20B

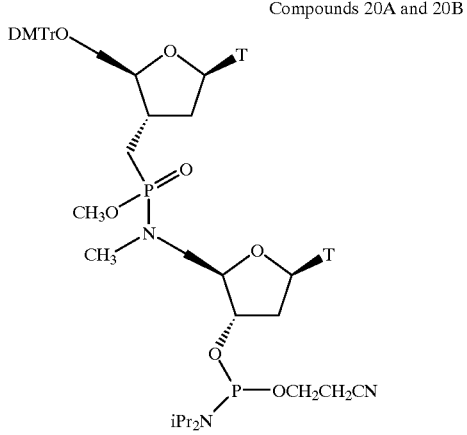

T = 1-thyminyl
DMTr = dimethoxytrityl
iPr = isopropyl

The procedure of Example 12 is repeated using Compound 19A (720 mg, 0.82 mmol) in place of Compound 9 and using 706 mg (4.12 mmol) of diisopropylammonium tetrazolide, 745 mg (2.47 mmol) of 2-cyanoethyl bis(N,N-diisopropyl)phosphordiamidite and 25 ml of dichloromethane instead of the amounts used in that Example, to give Compound 20A.

$^{31}$P NMR (CD$_2$Cl$_2$, 202 MHz) δ 149.9, 149.8, 35.3, 35.2 ppm

Found C, 58.73; H, 6.98; N, 8.60; C$_{53}$H$_{69}$N$_7$O$_{13}$P$_2$.H$_2$O requires C, 58.29; H, 6.55; N, 8.98.

The procedure of Example 12 is repeated using Compound 198 (502 mg, 0.57 mmol) in place of Compound 9 and using 492 mg (2.87 mmol) of diisopropylammonium tetrazolide, 519 mg (1.72 mmol) of 2-cyanoethyl bis (diisopropylamino)phosphordiamidite and 17 ml of dichloromethane instead of the amounts used in that Example, to give Compound 20B.

$^{31}$P NMR (CD$_2$Cl$_2$, 202 MHz) δ 150.1, 149.9, 36.3, 36.2 ppm.

Found C, 58.45; H, 6.51; N, 8.74; C$_{53}$H$_{69}$N$_7$O$_{13}$P$_2$.H$_2$O requires C, 58.29; H, 6.55; N, 8.98.

EXAMPLE 22

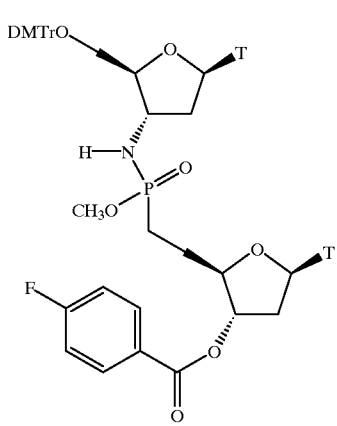

Compound 21

T = 1-thyminyl
DMTr = dimethoxytrityl

To a solution of Compound L (1.43 g, 2.50 mmol) and Compound M (1.44 g, 3.27 mmol) in pyridine (30 ml) is added BSTFA (4.3 mls, 16.25 mmols) at 0° C. After 30 minutes the reaction mixture is heated to 50° C. for 3 hours then methanol (10 ml) is added. The mixture is evaporated and the residue is purified by flash column chromatography on silica gel, eluting with 9:1 ethyl acetate/methanol to give Compound 21 as a mixture of diastereomers.

$^{31}$P NMR (CDCl$_3$, 162 MHz) δ 35.65, 35.41 ppm

MS (ES, HCOOH) 982 (loss DMTr)

Found C, 58.87; H, 5.57; N, 6.66; C$_{50}$H$_{53}$FN$_5$O$_{13}$P.2H$_2$O requires C, 58.99; H, 5.64; N, 6.88.

EXAMPLE 23

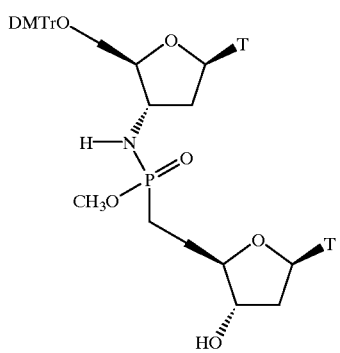

Compound 22

T = 1-thyminyl
DMTr = dimethoxytrityl

To a solution of Compound 21 (0.82 g, 831 μmol) in methanol (10 ml) is added sodium methoxide (89 mg, 1.66 mmol) at room temperature. After 18 hours the reaction mixture is evaporated then chromatographed on silica gel eluting with 4:1 ethyl acetate/methanol to give Compound 22 as a 1:1 mixture of diastereomers.

$^{31}$P NMR (CD$_3$OD, 162 MHz) δ 38.6, 38.5 ppm

MS (ES, HCOOH) 860 (MH$^+$)

Found C, 57.92; H, 6.09; N, 7.62; C$_{43}$H$_{50}$N$_5$O$_{12}$P.2H$_2$O requires C, 57.65; H, 6.08; N, 7.82.

EXAMPLE 24

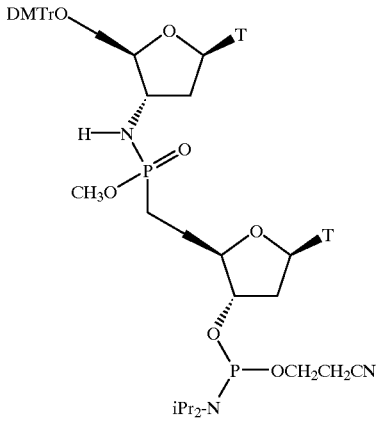

Compound 23

T = 1-thyminyl
DMTr = dimethoxtrityl
iPr = isopropyl

To a solution of Compound 22 (314 mg, 365 μmol) and diisopropylethylamine (472 μl, 2.74 mmol) in dichloromethane (5 ml) and acetonitrile (5 ml) is added dropwise 2-cyanoethyl N,N-diisopropylchlorophosphoramidite (203 μl, 912 μmol) at 0° C. After 5 hours at room temperature the reaction mixture is diluted with dichloromethane (20 ml), washed with saturated aqueous NaHCO$_3$ (10 ml), then with water (10 ml) and the organic extracts are dried over sodium sulphate. Purification by flash column chromatography on silica gel eluting with 9:1 chloroform/methanol, followed by precipitation of a dichloromethane solution (3 ml) from pentane (100 ml) gives Compound 23 as an amorphous white solid.

$^{31}$P NMR (CDCl$_3$, 162 MHz) δ 149.62, 149.47, 149.09, 148.87, 36.10, 35.95, 35.83, 35.48 ppm

EXAMPLE 25

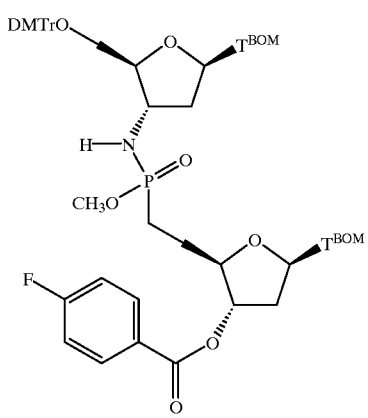

Compound 24

T$^{BOM}$ = N-benzyloxymethyl-1-thyminyl
DMTr = dimethoxytrityl

The procedure of Example 5 is repeated using Compound 21 (2.00 g, 2.04 mmol) in place of Compound 1 and using 0.88 ml (5.30 mmol) of benzyloxymethyl chloride, 2.44 ml (16.32 mmol) of DBU and 30 ml of acetonitrile instead of the amounts used in that Example, to give Compound 24.

$^{31}$P NMR (CDCl$_3$, 162 MHz) δ 34.9, 34.4 ppm

EXAMPLE 26

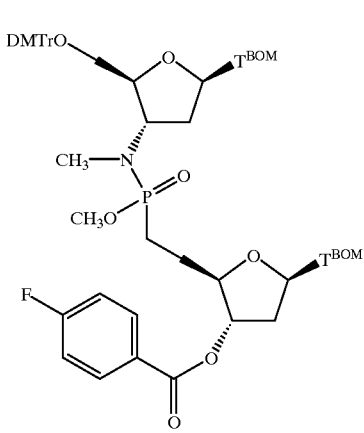

Compound 25

T^BOM = N-benzyloxymethyl-1-thyminyl
DMTr = dimethoxytrityl

The procedure of Example 15 is repeated using Compound 24 (1.58 g, 1.9 mmol) in place of Compound 5 and using 93 mg (3.88 mmol) of sodium hydride, 8 ml (129 mmol) of iodomethane and 10 ml of toluene instead of the amounts used in that Example, to give Compound 25.

$^{31}$P NMR (CDCl$_3$, 162 MHz) δ 36.82, 36.72 ppm

EXAMPLE 27

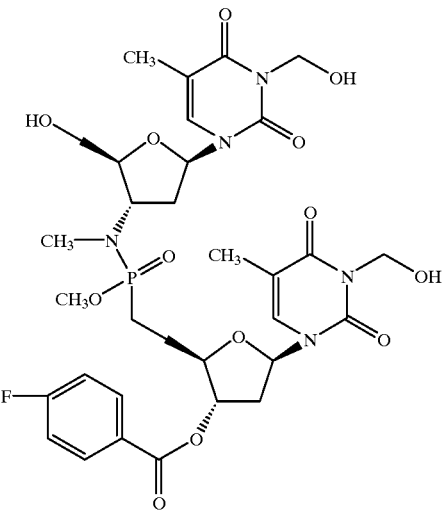

Compound 26

T = 1-thyminyl

The procedure of Example 16 is repeated using Compound 25 (460 mg, 372 μmol) in place of Compound 15A and using 200 mg of 10% palladium on carbon, 10 ml of ethanol and 15 ml of methanol instead of the amounts used in that Example, to give Compound 26.

$^{31}$P NMR (CD$_3$OD, 162 MHz) δ 40.58, 40.44 ppm

EXAMPLE 28

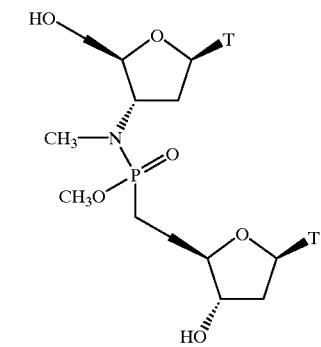

Compound 27

T = 1-thyminyl

The procedure of Example 23 is repeated using Compound 26 (280 mg, 372 μmol) in place of Compound 21 and using 40 mg (744 μmol) of sodium methoxide and 10 ml of methanol instead of the amounts used in that Example, to give Compound 27.

$^{31}$P NMR (CD$_3$OD, 162 MHz) δ 40.80, 40.64 ppm

EXAMPLE 29

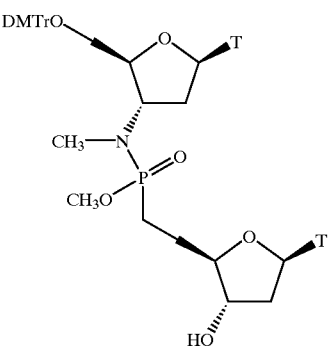

Compound 28

T = 1-thyminyl
DMTr = dimethoxytrityl

The procedure of Example 9 is repeated using Compound 27 (177 mg, 310 μmol) in place of Compound 6 and using 157 mg (464 μmol) of dimethoxytrityl chloride and 10 ml of pyridine instead of the amounts used in that Example, to give Compound 28.

$^{31}$P NMR (CDCl$_3$, 162 MHz) δ 38.26, 37.79 ppm

EXAMPLE 30

Compound 29

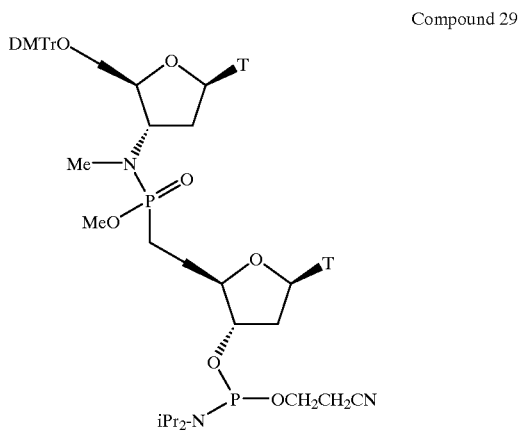

T = 1-thyminyl
DMTr = dimethoxytrityl
iPr = isopropyl

The procedure of Example 24 is repeated using Compound 28 (237 mg, 271 μmol) in place of Compound 22 and 2-cyanoethyl bis-(N,N-diisopropyl)phosphordiamidite (151 μl, 6.77 mmol) instead of the phosphoramidite used in that Example, and using 350 μl (2.03 mmol) of diisopropylethylamine, 3 ml of dichloromethane and 3 ml of acetonitrile instead of the amounts used in that Example, to give Compound 29.

$^{31}$P NMR (CDCl$_3$, 202 MHz) δ 150.04, 150.00, 149.89, 149.89, 38.28, 38.18, 38.09, 37.99 ppm

EXAMPLE 31

Compound 30

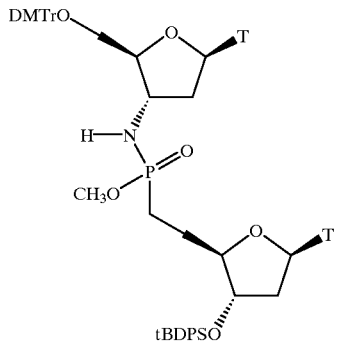

T = 1-thyminyl
DMTr = dimethoxytrityl

The procedure of Example 22 is repeated using Compound R (2.0 g, 3.59 mmol) in place of Compound M and using 1.57 g (2.76 mmol) of Compound L, 4.76 ml (17.94 mmol) of BSTFA and 40 ml of pyridine instead of the amounts used in that Example, to give Compound 30.

$^{31}$P NMR (CDCl$_3$, 162 MHz) δ 35.93, 35.38 ppm

Found C, 63.15; H, 6.43; N, 6.02; C$_{59}$H$_{68}$N$_5$O$_{12}$PSi.H$_2$O requires C, 63.48; H, 6.32; N, 6.27.

EXAMPLE 32

Compound 31A and 31B

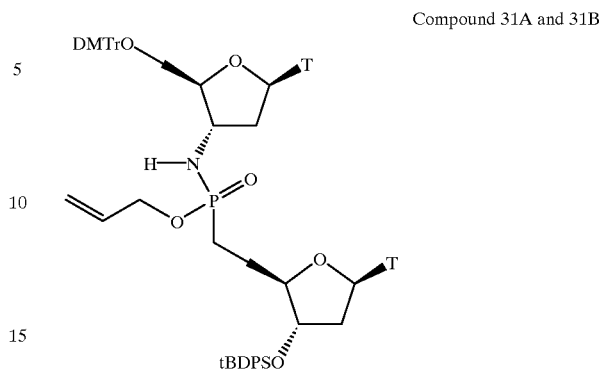

T = 1-thyminyl
DMTr = dimethoxytrityl

The procedure of Example 22 is repeated using Compound S (2.69 g, 4.62 mmol) in place of Compound M and using 2.0 g (3.55 mmol) of Compound L, 6.3 ml (23.7 mmol) of BSTFA and 50 ml of pyridine instead of the amounts used in that Example, the chromatography being carried out using 95% ethyl acetate, 5% methanol as eluant to separate the mixture of diastereomers.

Compound 31A (higher Rf)=$^{31}$P NMR (CDCl$_3$, 202 MHz) δ 35.4 ppm

MS (ESP+)1147 (M+Na).

Compound 31B (lower Rf)=$^{31}$P NMR (CDCl$_3$, 202 MHz) δ 35.9 ppm

MS(ESP+)1147 (M+Na).

EXAMPLE 33

Compound 32A and 32B

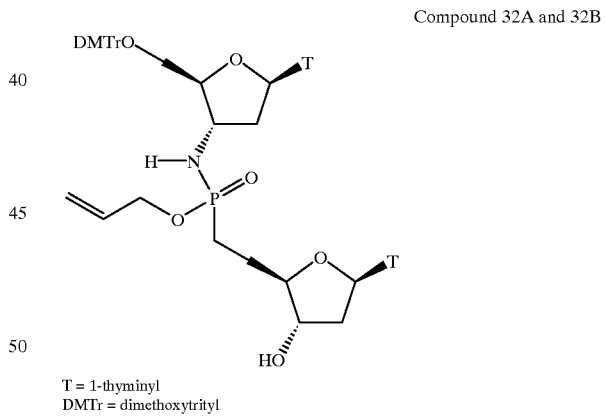

T = 1-thyminyl
DMTr = dimethoxytrityl

The procedure of Example 6 is repeated using Compound 31A (1.65 g, 1.47 mmol) in place of Compound 1 and using 2.9 ml (2.94 mmol) of TBAF/THF solution and 20 ml of THF instead of the amounts used in that Example, to give Compound 32A as a single diastereomer.

$^{31}$P NMR (CDCl$_3$, 202 MHz) δ 36.5 ppm

The procedure of Example 6 is repeated using Compound 31B (1.27 g, 1.13 mmol) in place of Compound 1 and using 2.2 ml (2.26 mmol) of the TBAF/THF solution and 20 ml of THF instead of the amounts used in that Example, to give Compound 328 as a single diastereomer.

$^{31}$P NMR (CDCl$_3$, 202 MHz) δ 36.1 ppm

EXAMPLE 34

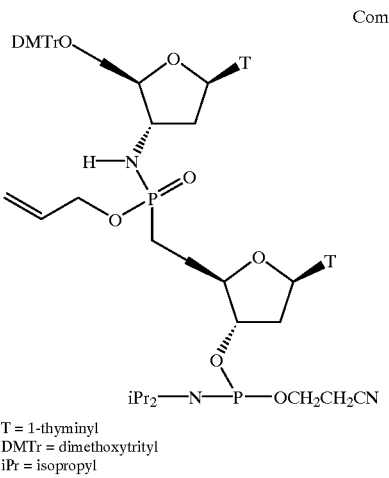

Compound 33A and 33B

T = 1-thyminyl
DMTr = dimethoxytrityl
iPr = isopropyl

The procedure of Example 12 is repeated using Compound 32A (846 mg, 0.95 mmol) in place of Compound 9 and using 818 mg (4.77 mmol) of the tetrazolide, 864 μl (2.86 mmol) of the phosphordiamidite and 25 ml of dichloromethane instead of the amounts used in that Example, to give Compound 33A.

$^{31}$P NMR (CDCl$_3$, 162 MHz) δ 149.6, 148.9,34.9, 34.6 ppm

The procedure of Example 12 is repeated using Compound 32B (834 mg, 0.94 mmol) in place of Compound 9 and using 806 mg (4.71 mmol) of the tetrazolide, 851 μl (2.82 mmol) of the phosphordiamidite and 25 ml of the dichloromethane, to give Compound 33B.

$^{31}$P NMR (CDCl$_3$, 202 MHz) δ 150.0, 149.7, 36.1, 35.9 ppm

EXAMPLE 35

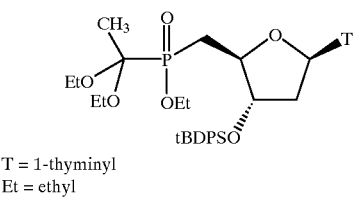

Compound 34

T = 1-thyminyl
Et = ethyl

To a solution of 1-(1,1-diethoxyethyl) ethyl phosphinate (53.6 g, 0.255 mol) in dry THF (1 liter) at −78° C. under argon is added dropwise a solution of potassium bis(trimethylsilyl)amide (315.7 ml, 0.75 mol solution in hexanes) over 1 hour. To the resulting solution is added a solution of Compound H (50 g, 0.085 mol) in THF (200 ml) over 15 minutes. The resulting solution is allowed to warm slowly to room temperature over 18 hours. Saturated aqueous ammonium chloride solution (500 ml) is added, followed by ethyl acetate (600 ml). The resulting organic phase is separated, washed with brine (2×250 ml) dried (MgSO$_4$) and concentrated. Purification by silica column chromatography (chloroform/ethylacetate mixtures) gives Compound 34, isolated as a 2:1 mixture of diastereomers.

$^{31}$P NMR $^1$H decoupled (CDCl$_3$, 162 MHz) δ 45.2 ppm

Found C, 59.05; H, 7.30; N, 3.85%, C$_{34}$H$_{49}$N$_2$O$_8$PSi.H$_2$O requires C, 59.10; H, 7.45; N, 4.05%.

EXAMPLE 36

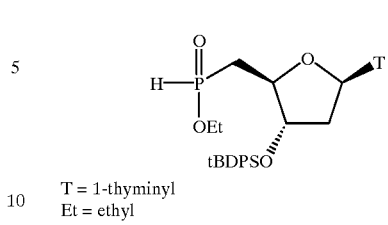

Compound 35

T = 1-thyminyl
Et = ethyl

To a solution of Compound 34 (57.2 g, 0.085 mol) in chloroform (800 ml) and ethanol (12 ml) is added trimethylsilylchloride (100 ml) under argon at room temperature. After standing at ambient temperature for 18 hours, the solution is concentrated. Purification by flash silica column chromatography (eluant chloroform/ethyl acetate mixtures) gives Compound 35, isolated as a 2:1 mixture of diastereomers.

$^{31}$P NMR $^1$H decoupled (CDCl$_3$, 162 MHz) δ 33.4, 33.1 ppm

Found C, 57.7; H, 6.75; N, 4.45%; C$_{28}$H$_{37}$N$_2$O$_6$PSi·½H$_2$P requries C, 57.6; H, 6.90; N, 4.80%.

EXAMPLE 37

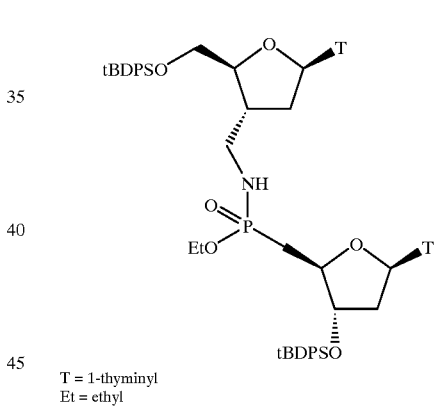

Compound 36

T = 1-thyminyl
Et = ethyl

To a solution of Compound 35 (0.975 g, 1.75 mmol) and Compound V (0.60 g, 1.15 mmol) in dry pyridine (7.5 ml) at 0° C. under argon is added bis(trimethylsilyl)trifluoroacetamide (2.32 ml, 8.73 mmol) dropwise over 5 minutes. The resulting solution is stood at 0°–5° C. for 70 hours before concentration at 50° C., under reduced pressure to remove most of the pyridine, ethanol-water (1:1, 10 ml) is then added and the resulting mixture heated at 80° C. for 4 hours. Concentration and flash silica column chromatography (gradient elution ethyl acetate—ethyl acetate/ethanol 15:1) gives Compound 36 as a mixture of diastereomers.

$^{31}$P NMR $^1$H decoupled (CDCl$_3$, 162 MHz) δ 30.5, 30.9 ppm

Found C, 61.30; H, 6.85; N, 6.45%; C$_{55}$H$_{70}$N$_5$O$_{10}$PSi$_2$.½H$_2$O requires C, 61.45; H, 6.85; N, 6.50%.

EXAMPLE 38

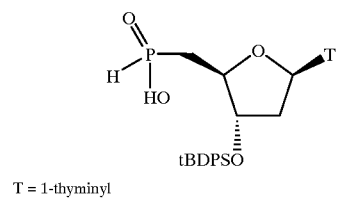

Compound 37

T = 1-thyminyl

A solution of Compound 35 (6.9 g, 12.4 mmol) in a mixture of ethanol, triethylamine and water (30 ml, 30 ml, 15 ml) is stirred at room temperature for 2 hours. The mixture is concentrated and then taken up into ethyl acetate. This solution is washed with 0.1 N HCl until the washings remain mildly acidic. The organic phase is separated, washed with water and dried ($Na_2SO_4$). Concentration gives Compound 37 as a white solid.

$^{31}$P NMR $^1$H decoupled (CDCl$_3$, 162 MHz) δ 34.2 ppm

EXAMPLE 39

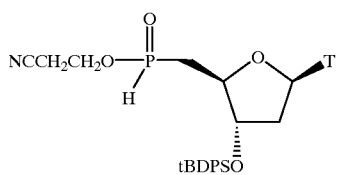

Compound 38

T = 1-thyminyl

A solution of Compound 37 (0.53 g, 1 mmol), 3-hydroxypropionitrile (71 μl, 1.0 mmol) and dimethylaminopyridine (10 mg) in dry THF under argon is heated to 80° C. Dicyclohexylcarbodiimide (DCC) (0.207 g, 1 mmol) is added and heating continued for 2 hours. The solution is cooled to room temperature and diluted with THF. The precipitated dicyclohexylurea is removed by filtration to give after concentration Compound 38, isolated as a 1:1 mixture of diastereomers.

$^{31}$P NMR $^1$H decoupled (CDCl$_3$, 162 MHz) δ 36.5, 36.2 ppm

EXAMPLE 40

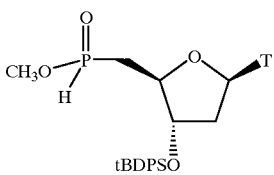

Compound 39

T = 1-thyminyl

To a solution of Compound 37 (6.3 g, 11.9 mmol) in dry THF (50 ml) under argon is added methanol (0.43 g, 13.4 mmol) and catalytic dimethylaminopyridine (10 mg). The resulting solution is stirred at room temperature for 5 minutes before the addition of dicyclohexylcarbodiimide (2.70 g, 13.1 mmol). After stirring at room temperature for 2 hours, the solution is filtered and the precipitated solid washed with THF. The resulting filtrate is concentrated and purified by flash silica column chromatography (eluant ethyl acetate) to give Compound 39, which is isolated as a 1:1 mixture of diastereomers.

$^{31}$P NMR $^1$H decoupled (CDCl$_3$, 162 MHz) δ 36.3, 36.2 ppm

EXAMPLE 41

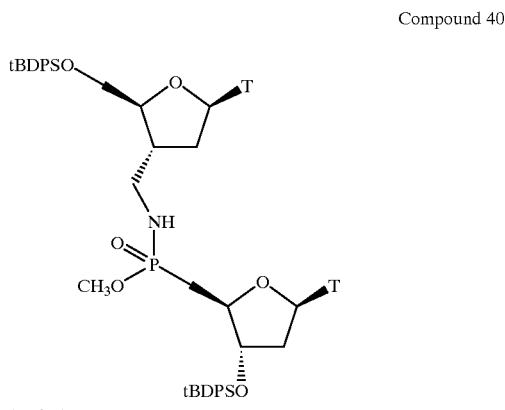

Compound 40

T = 1-thyminyl

Compound 40 is synthesized by the method of Example 37 but replacing Compound 35 by Compound 39. In the final hydrolysis the ethanol used in Example 37 is replaced by methanol. Purification by flash silica column chromatography (eluant ethyl acetate—methanol mixtures) gives Compound 40.

$^{31}$P NMR $^1$H decoupled (CDCl$_3$, 162 MHz) δ 32.6, 32.1 ppm

Found C, 61.15; H, 6.60; N, 6.50%; $C_{54}H_{68}N_5O_{10}PSi_2 \cdot \frac{3}{2}H_2O$ requires C, 61.10; H, 6.75; N, 6.60%.

MS m/z 1034.4 (MH$^+$) electrospray positive mode

EXAMPLE 42

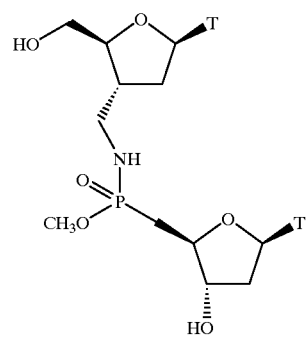

Compound 41

T = 1-thyminyl

Compound 41 is prepared by the method of Example 6, substituting Compound 40 for Compound 1, and purifying by flash silica column chromatography (eluant methanol-ethyl acetate mixtures) to give the pure product isolated as a 1:1 mixture of diastereomers.

$^{31}$P NMR $^1$H decoupled (CDCl$_3$, 162 MHz) δ 36.1, 35.7 ppm

MS m/z 558.3 (MH$^+$), 580.3 (MNa$^+$) electrospray positive mode

EXAMPLE 43

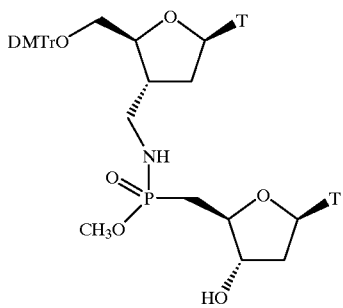

Compound 42

T = 1-thyminyl
DMTr = dimethoxytrityl

To a solution of Compound 41 (478 mg, 0.857 mmol) in dry pyridine (10 ml) is added dimethoxytrityl chloride (436 mg, 1.29 mmol) under argon at room temperature. After 18 hours at room temperature, the mixture is concentrated, dissolved in chloroform and washed with saturated aqueous NaHCO$_3$ solution and then brine. Drying (MgSO$_4$), concentration followed by flash silica column chromatography (eluant:chloroform-methanol mixtures containing 1% trethylamine) and further dissolution in chloroform followed by washing with dilute aqueous NaHCO$_3$ solution and drying over MgSO$_4$ gives Compound 42 isolated as a 1:1 mixture of diastereoisomers.

$^{31}$P NMR $^1$H decoupled (CDCl$_3$, 162 MHz) δ 34.2 ppm
MS m/z 860.4 (MH$^+$) electrospray positive mode

EXAMPLE 44

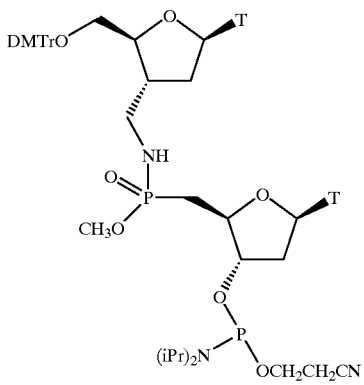

Compound 43

T = 1-thyminyl
DMTr = dimethoxytrityl
iPr = isopropyl

A mixture of Compound 42 (150 mg, 0.175 mmol) and diisopropylamine tetrazolide (155 mg, 0.90 mmol) is dried under high vacuum for 3 hours. Dichloromethane (7.5 ml) is then added and the resulting solution stirred under an argon atmosphere at room temperature while 2-cyanoethyl bis-(N, N-diisopropyl)-phosphordiamidite (230 μl, 0.7 mmol) is added dropwise over 10 minutes. After 18 hours at room temperature the mixture is poured onto saturated aqueous NaHCO$_3$ and extracted with dichloromethane. The organic phase is dried (Na$_2$SO$_4$) and evaporated. The crude product is then dissolved in CH$_2$Cl$_2$ (1–5 ml) and added dropwise to cold (0–5° C.) pentane (500 ml) with vigorous stirring. The resulting precipitate is collected by filtration. The dissolution in CH$_2$Cl$_2$ followed by precipitation is repeated two or three times to furnish the product Compound 43 as a white solid which is isolated as a mixture of four diastereoisomers.

$^{31}$P NMR $^1$H decoupled (CDCl$_3$, 162 MHz) δ 149.5, 149.4,149.2,32.75,32.70,32.2, 31.9 ppm Found C, 56.70; H, 6.30; N, 8.80%; C$_{52}$H$_{67}$N$_7$O$_{13}$P$_2$.2H$_2$O requires C, 57.0; H, 6.55; N, 8.95%.

MS m/z 1082.4 (MNa$^+$) electrospray positive mode

EXAMPLE 45

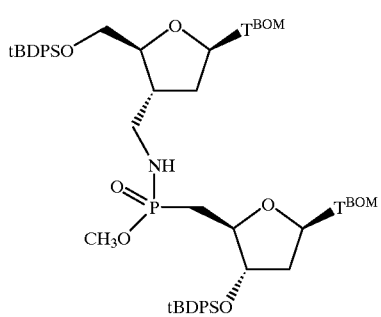

Compound 44

T$^{BOM}$ = N-benzyloxymethyl-1-thyminyl

To a solution of Compound 40 (6.20 g, 6 mmol) in dry acetonitrile (150 ml) under argon at room temperature is added DBU (7.56 ml) followed by 80% pure benzyloxymethylchloride (2.52 ml, 14.5 mmol). After standing at room temperature for 20 hours, the reaction mixture is partially concentrated (bath temperature 0–5° C.) and saturated aqueous NaHCO$_3$ (100 ml) added followed by ethyl acetate (500 ml). The organic layer is separated, washed with water and dried over sodium sulphate. Purification by flash silica column chromatography (gradient elution with ethyl acetate:methanol mixtures) gives Compound 44 as a white solid and isolated as a 1:1 mixture of diastereoisomers.

Found C, 65.05; H, 6.75; N, 5.35%; C$_{70}$H$_{84}$N$_5$O$_{12}$PSi$_2$.H$_2$O requires C, 65.05; H, 6.70; N, 5.40%.

$^{31}$P NMR $^1$H decoupled (CDCl$_3$, 162 MHz) δ 31.9, 31.8 ppm

MS m/z 1297.5 (MNa$^+$), 1274.5 (MH$^+$) electrospray positive mode

EXAMPLE 46

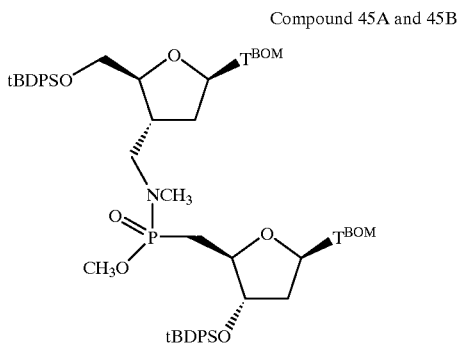

Compound 45A and 45B

-continued

T<sup>BOM</sup> = N-benzyloxymethyl-1-thyminyl

To a solution of Compound 44 (5.5 g, 4.31 mmol) in dry toluene (86.3 ml) under argon is added sodium hydride (60% dispersion in mineral oil) (431 mg, 10.79 mmol). After the effervescence has subsided methyl iodide (16.2 ml, 0.26 mol) is added. The resulting mixture is heated at 40° C. for 24 hours, further methyl iodide (16.2 ml, 0.26 mol) is added and heating at 40° C. is continued. After heating for a further 24 hours additional methyliodide (16.2 ml, 0.26 mol) is added. After a further 24 hours, the reaction mixture is cooled and poured onto water. Extraction with ethyl acetate and drying over sodium sulphate gives the crude product. Repeated flash silica column chromatography (ethyl acetate-hexane mixtures) gives the first eluting diastereoisomer Compound 45A followed by Compound 45B as the slower eluting diastereoisomer.

Compound 45A: $^{31}$P NMR $^{1}$H decoupled (CDCl$_3$, 162 MHz) δ 33.4 ppm

MS m/z 1310–13 (M+Na$^+$) electrospray positive mode

Compound 45B: $^{31}$P NMR $^{1}$H decoupled (CDCl$_3$, 162 MHz) δ 33.1 ppm

MS m/z 1310–13 (M+Na$^+$) electrospray positive mode

EXAMPLE 47

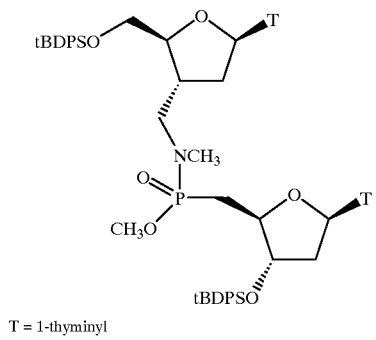

Compound 46A

Compound 45A (2.24 g, 1.73 mmol) is dissolved in a methanol/ethanol mixture (1:1, 150 ml) and the whole purged with argon. Pearlmans catalyst (palladium hydroxide, 0.5 g) is added and the resulting suspension stirred under an atmosphere of hydrogen for 72 hours. The mixture is filtered and concentrated. The resulting solid is dissolved in ethyl acetate, washed with water, dried over magnesium sulphate and concentrated. The resulting solid is dissolved in methanol (100 ml) and catalytic sodium methoxide added with stirring. After 24 hours the mixture is neutralized with acetic acid and concentrated. The resulting solid is dissolved in ethyl acetate (100 ml), washed with water (2×25 ml), dried over magnesium sulphate and concentrated to give Compound 46A.

Found C, 61.65; H, 7.05; N, 6.20%; C$_{55}$H$_{70}$N$_5$O$_{10}$PSi$_2$.H$_2$O requires C, 61.95; H, 6.80; N, 6.55%.

$^{31}$P NMR $^{1}$H decoupled (CDCl$_3$, 162 MHz) δ 33.6 ppm

MS m/z 1047–1049 (MH$^-$) electrospray negative mode

EXAMPLE 48

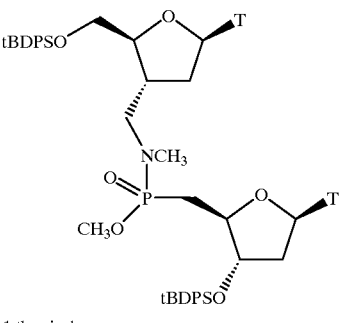

Compound 46B

T = 1-thyminyl

Compound 46B is synthesized by the method of Example 47, but starting from Compound 45B instead of 45A.

$^{31}$P NMR $^{1}$H decoupled (CDCl$_3$, 162 MHz) δ 33.3 ppm

EXAMPLE 49

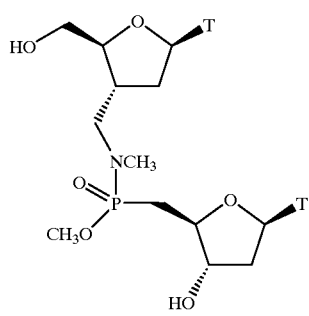

Compound 47A

T = 1-thyminyl

To a solution of Compound 46A (1.5 g, 1.43 mmol) in THF (35 ml) at room temperature is added a solution of tetrabutylammonium fluoride in THF (4.29 ml, 1 molar). After standing at room temperature for 20 hours, the mixture is concentrated and purified by flash silica column chromatography (gradient elution: ethyl acetate-methanol 40:1–4:1) to give Compound 47A.

Found C, 44.95; H, 6.30; N, 10.95%; C$_{23}$H$_{34}$N$_5$O$_{10}$P.½H$_2$O requires C, 44.80; H, 6.40; N, 11.35%.

$^{31}$P NMR $^{1}$H decoupled (CD$_3$OD, 162 MHz) δ 37.4 ppm

EXAMPLE 50

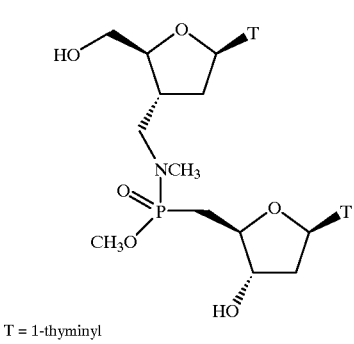

Compound 47B

T = 1-thyminyl

Compound 47B is synthesized by the method of Example 49 but starting from Compound 46B instead of Compound 46A.

$^{31}$P NMR $^1$H decoupled (CD$_3$OD, 162 MHz) δ 36.6 ppm

EXAMPLE 51

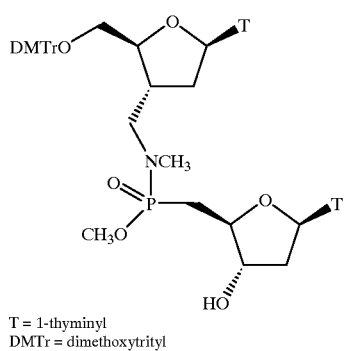

Compound 48A and 48B

T = 1-thyminyl
DMTr = dimethoxytrityl

Compound 47A (455 mg, 0.80 mmol) is carefully dried by coevaporation with anhydrous pyridine (2×5 ml). Anhydrous pyridine (5 ml) is added followed by dimethoxytrityl chloride (405 mg, 1.19 mmol) and the resulting mixture is stirred under argon for 4 hours. The mixture is then concentrated, dissolved in dichloromethane (50 ml) and washed with saturated aqueous sodium bicarbonate solution followed by brine. Drying over sodium sulphate, concentration and purification by flash silica column chromatography (gradient elution: chloroform/methanol/triethylamine 95:5:1–89:10:1) gives Compound 48A.

$^{31}$P NMR $^1$H decoupled (CDCl$_3$, 162 MHz) δ 35.1 ppm

MS m/z 896–898 (MNa$^+$) electrospray positive mode

Compound 48B is made by the method used for Compound 48A but using Compound 47B as starting material in place of Compound 47A.

$^{31}$P NMR $^1$H decoupled (CDCl$_3$, 162 MHz) δ 35.7 ppm

MS m/z 896–898 (MNa$^+$) electrospray positive mode

EXAMPLE 52

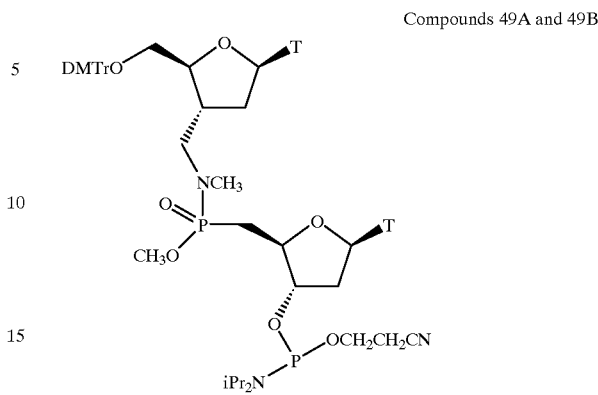

Compounds 49A and 49B

T = 1-thyminyl
DMTrO = dimethoxytrityl
iPr = isopropyl

Compound 49A is prepared by a procedure analogous to that of Example 44, but replacing Compound 42 with Compound 48A. After initial precipitation from dichloromethane-pentane (1:100), the product is further purified by flash silica column chromatography (eluant: chloroform/methanol/triethylamine 98.5:1:0.5) and finally precipitation from dichloromethane-pentane (1:100) to give Compound 49A isolated as a 1:1 mixture of diastereoisomers at the phosphorus III center.

$^{31}$P NMR $^1$H decoupled (CDCl$_3$, 202 MHz) δ 150.19, 150.02, 34.63, 34.25 ppm MS m/z 1097–1099 (MNa$^+$) electrospray positive mode Compound 49B is prepared by the method described for Compound 49A but replacing Compound 48A in this method with Compound 48B isolated as a 1:1 mixture of diastereoisomers at the phosphorus II center.

$^{31}$P NMR $^1$H decoupled (CDCl$_3$, 202 MHz) δ 150.17, 150.08, 34.16, 33.63 ppm MS m/z 1097–1100 (MNa$^+$)$^+$ electrospray positive mode

EXAMPLE 53

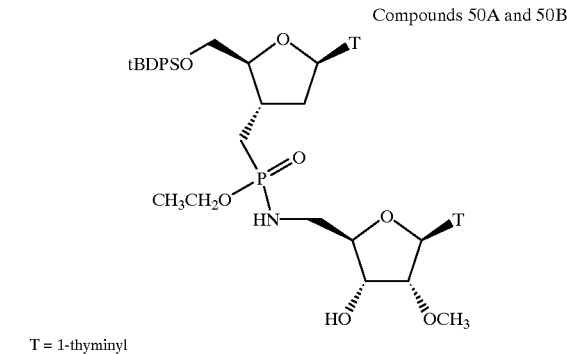

Compounds 50A and 50B

T = 1-thyminyl

Bis(trimethylsilyl)trifluoroacetamide (4.95 ml, 18.66 mmol) is added dropwise to a solution of Compound D (1.95 g, 3.42 mmol) and Compound Y (0.932 g, 3.11 mmol) in dry pyridine (40 ml)) at 0° C. under an argon atmosphere. The resulting solution is allowed to slowly warm to room temperature over 30 minutes and is then stirred at room temperature for 20 hours.

Methanol (50 ml) is added and the mixture is then concentrated. The resulting product is dissolved in a chloroform (100 ml)—methanol (50 ml) mixture and refluxed for 4 hours. Concentration and purification by flash silica column chromatography (gradient elution; chloroform:ethanol 20:1–4:1) gives firstly Compound 50A followed by Compound 50B as the slower eluting diastereoisomer at phosphorus.

Compound 50A:

Found C, 54.95; H, 6.60; N, 7.75%; $C_{40}H_{54}N_5O_{10}PSi.2H_2O$ requires C, 54.85; H, 6.65; N, 8.00%.

$^{31}P$ NMR $^1H$ decoupled (CDCl$_3$, 162 MHz) δ 32.6 ppm

Compound 50B:

Found C, 52.95; H, 6.25; N, 7.50%; $C_{40}H_{54}N_5O_{11}PSi.½H_2O.½CHCl_3$ requires C, 53.00; H, 6.20; N, 7.65%.

$^{31}P$ NMR $^1H$ decoupled (CDCl$_3$, 162 MHz) δ 32.8 ppm

EXAMPLE 54

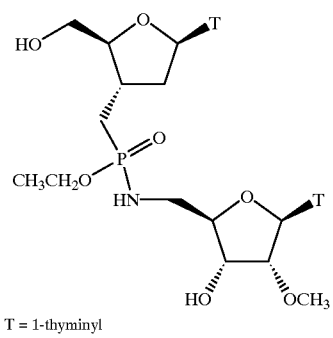

Compounds 51A and 51B

T = 1-thyminyl

To a solution of Compound 50A (1.05 g, 1.25 mmol) in THF (30 ml) at room temperature is added a solution of tetra-butylammonium fluoride (0.36 ml, 1.0 molar) in THF. After standing at room temperature for 70 hours, concentration and purification by flash silica column chromatography (gradient elution; chloroform:ethanol 9:1–4:1) gives Compound 51A.

Found C, 47.0; H, 6.50; N, 10.95%; $C_{24}H_{36}N_5O_{11}P.H_2O$ requires C, 46.55; H, 6.20; N, 11.30%.

Compound 51B is made by the method used for Compound 51A but using Compound 50B as starting material in place of Compound 50A.

$^{31}P$ NMR $^1H$ decoupled (CD$_3$OD, 162 MHz) δ 36.4 ppm

EXAMPLE 55

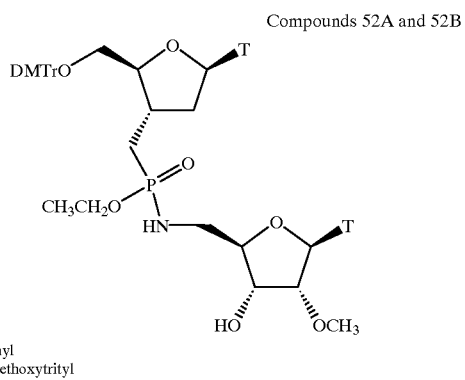

Compounds 52A and 52B

T = 1-thyminyl
DMTr = dimethoxytrityl

Compound 51B (0.54 g, 0.9 mmol) is carefully dried by coevaporation with anhydrous pyridine. Anhydrous pyridine (11 ml) is added, followed by dimethoxytrityl chloride (0.37 g, 1.1 mmol) with stirring under an argon atmosphere at room temperature. After 24 hours, additional dimethoxytrityl chloride is added (0.12 g, 0.35 mmol) and stirring continued for a further 5 hours. Methanol (15 ml) is added and the reaction mixture concentrated. The resulting thick oil is dissolved in chloroform (40 ml) and saturated aqueous sodium hydrogen carbonate solution (30 ml) is added. The organic phase is separated and the aqueous layer further extracted with chloroform (2×40 ml). The combined organic phase is then dried (Na$_2$SO$_4$) and concentrated. Purification by flash silica column chromatography (eluant chloroform-ethanol 9:1) gives Compound 52B.

$^{31}P$ NMR $^1H$ decoupled (CDCl$_3$, 162 MHz) δ 32.7 ppm

Compound 52A is made by the method used for Compound 52B but using Compound 51A as starting material in place of Compound 51B.

$^{31}P$ NMR $^1H$ decoupled (CDCl$_3$, 162 MHz) δ 32.6 ppm

Found C, 56.40; H, 5.80; N, 6.90%; $C_{45}H_{54}N_5O_{13}P.½CH_2Cl_2.H_2O$ requries C, 56.65; H, 5.95; N, 7.25%.

EXAMPLE 56

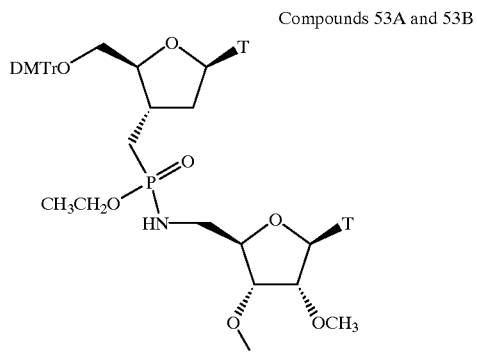

Compounds 53A and 53B

T = 1-thyminyl
DMTr = dimethoxytrityl
iPr = isopropyl

Compound 53B is made by a procedure analogous to that of Example 44, but using Compound 52B as starting material in place of Compound 42. After initial precipitation from dichloromethane-pentane (1:15) the product is further purified by flash silica column chromatography (eluant chloroform:ethanol:triethylamine 94:5:1). After concentration the product is redissolved in chloroform and washed with saturated aqueous sodium hydrogen carbonate solution, dried and concentrated. The precipitation procedure described above is then repeated a further two times to furnish Compound 53B as a white solid isolated as a 1:1 mixture of diastereoisomers at the Phosphorus III center.

Found C, 58.55; H, 6.80; N, 8.10%; $C_{54}H_{71}N_7O_{14}P_2.\tfrac{1}{2}C_5H_{12}.H_2O$ requires C, 58.60 H, 6.90; N, 8.45%.

$^{31}P$ NMR $^1H$ decoupled (CDCl$_3$, 202 MHz) δ 152.4, 151.1, 33.0, 32.8 ppm

Compound 53A is made by the method used for Compound 53B but using Compound 52A as starting material in place of Compound 52B and is again isolated as a 1:1 mixture of diastereoisomers at the phosphorus III center.

Found C, 58.6; H, 6.65; N, 8.25%; $C_{54}H_{71}N_7O_{14}P_2.\tfrac{1}{2}C_5H_{12}.H_2O$ requires C, 58.60; H, 6.90; N, 8.45%.

$^{31}P$ NMR $^1H$ decoupled (CDCl$_3$, 202 MHz) δ 152.5, 151.2, 32.3, 32.1 ppm

EXAMPLE 57

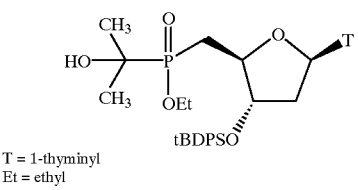

Compound 54

T = 1-thyminyl
Et = ethyl

To a solution of Compound 35 (3.5 g, 6.3 mmol) in dry THF (50 ml) under an argon atmosphere at 0–5° C. is added acetone (2 ml) followed by titanium isopropoxide (2.05 ml, 6.9 mmol) dropwise over 3 minutes. The resulting solution is allowed to warm to room temperature and is then stirred for a further 2 hours. The reaction mixture is then concentrated, dissolved in ethyl acetate (75 ml) and passed through a short bed of silica with ethyl acetate (225 ml) followed by chloroform-methanol (20:1) (225 ml). Concentration and purification by silica gel column chromatography (eluant chloroform-methanol 20:1) gives Compound 54 isolated as a mixture of 2 diastereoisomers at phosphorus.

$^{31}P$ NMR $^1H$ decoupled (CDCl$_3$, 162 MHz) δ 53.1, 53.0 ppm

EXAMPLE 58

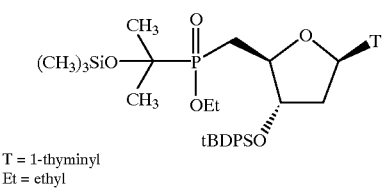

Compound 55

T = 1-thyminyl
Et = ethyl

To a solution of Compound 35 (0.68 g, 1.22 mmol) in dry dichloromethane (10 ml) under an argon atmosphere is added bis(trimethylsilyl)trifluoroacetamide (1.30 ml, 4.89 mmol). After stirring at room temperature for 10 minutes, acetone (2.5 ml) is added. After standing at room temperature for 6 hours, bis(trimethylsilyl)trifluoroacetamide (0.33 ml) is added. After standing for an additional 18 hours at room temperature the mixture is concentrated and coevaporated with methanol (2×10 ml). Purification by flash silica column chromatography (eluant ethyl acetate-hexane 2:1) gives Compound 55 as a mixture of 2 diastereoisomers at phosphorus.

Found C, 58.95; H, 7.50; N, 4.00%; $C_{34}H_{51}N_2O_7PSi_2.\tfrac{1}{4}H_2O$ requires C, 59.05; H, 7.50; N, 4.10%.

$^{31}P$ NMR $^1H$ decoupled (CDCl$_3$, 162 MHz) δ 52.8, 52.4 ppm

EXAMPLE 59

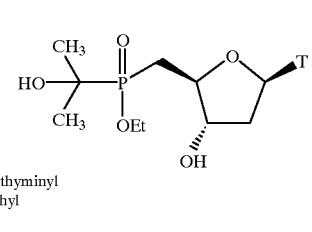

Compound 59

T = 1-thyminyl
Et = ethyl

To a solution of Compound 55 (508 mg, 0.74 mmol) in THF (40 ml) containing acetic acid (85 Ξl, 1.48 mmol) is added a 1 molar solution of tetra n-butylammoniumfluoride in THF (1.48 ml, 1.48 mmol). After stirring at room temperature for 2 hours, concentration and purification by flash silica column chromatography (eluant ethyl acetate-methanol 20:1) gives Compound 56 isolated as a mixture of two diastereoisomers at phosphorus.

Compound 56 can also be prepared from Compound 54 using the method of this Example but replacing Compound 55 with compound 54 and using only one equivalent of nBu$_4$NF.

Found C, 47.0; H, 6.90; N, 7.20%; $C_{15}H_{25}N_2O_7P.\tfrac{1}{3}H_2O$ requires C, 47.1; H, 6.75; N, 7.35%.

$^{31}P$ NMR $^1H$ decoupled (CDCl$_3$, 162 MHz) δ 56.6, 54.8 ppm

EXAMPLE 60

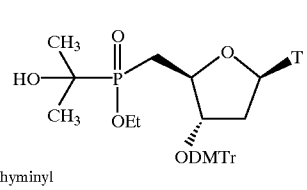

Compound 57

T = 1-thyminyl
Et = ethyl
DMTr = dimethoxytrityl

To a solution of Compound 56 (1.6 g, 4.25 mmol) in dry pyridine (10 ml) is added dimethoxytrityl chloride (1.8 g, 5.31 mmol). After standing at room temperature for 20 hours, the mixture is concentrated and purified by silica gel column chromatography (eluant:ethyl acetate:ethanol 20:1) to give Compound 57 as a mixture of two diastereoisomers at phosphorus.

Found C, 59.70; H, 6.20; N, 3.80%; $C_{36}H_{43}N_2O_9P.\tfrac{1}{2}H_2O$ requires C, 59.75; H, 6.70; N, 3.90%.

$^{31}P$ NMR $^1H$ decoupled (CDCl$_3$, 162 MHz) δ 53.5, 53.2 ppm

EXAMPLE 61

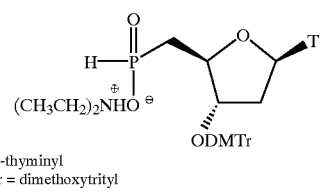

Compound 58

T = 1-thyminyl
DMTr = dimethoxytrityl

To a solution of Compound 57 (1.00 g, 1.47 mmol) in dry methanol (20 ml) is added DBU (1.14 g, 7.5 mmol) and the mixture stirred at 60° C. under an argon atmosphere for 3 hours. The mixture is concentrated and dissolved in water containing 0.5% triethylamine. This mixture is purified by passage through a DOWEX 50W-X2 ion exchange column (triethylamine form). The product is eluted with 0.5% triethylamine in water to give, after concentration, Compound 58.

$^{31}$P NMR $^{1}$H decoupled (CD$_3$OD, 162 MHz) δ 21.8 ppm

EXAMPLE 62

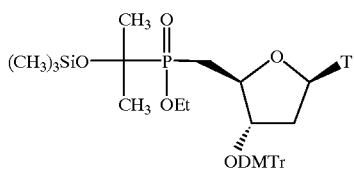

Compound 59

T = 1-thyminyl
DMTr = dimethoxytrityl
Et = ethyl

To a solution of Compound 57 (500 mg, 0.74 mmol) in dry THF (20 ml) at room temperature is added bis(trimethylsilyl)trifluoroacetamide (0.98 ml, 3.7 mmol). The resulting mixture is allowed to stand at room temperature for 20 hours. Concentration followed by coevaporation with methanol gives the crude product, which is purified by silica gel column chromatography (eluant ethyl acetate) to give Compound 59, isolated as a mixture of diastereoisomers.

$^{31}$P NMR $^{1}$H decoupled (CDCl$_3$, 162 MHz) δ 53.3, 52.7 ppm

EXAMPLE 63

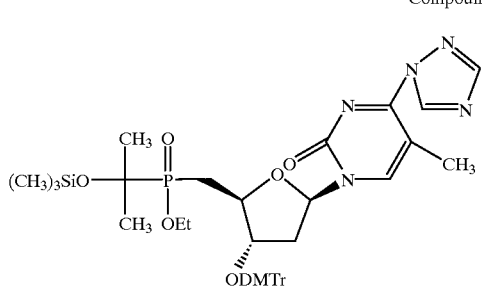

Compound 60

DMTr = dimethoxytrityl
Et = ethyl

To a solution of carefully dried triazole (138 mg, 2.0 mmol) in dry pyridine (1.5 ml) under argon at 0–5° C. is added triethylamine (300 μl) followed by phosphorus oxychloride (POCl$_3$) (46 μl, 0.5 mmol). The resultant solution is stirred at 0° C. tor 10 minutes before the dropwise addition of a solution of Compound 59 (150 mg, 0.2 mmol) in pyridine (0.5 ml). Stirring is continued at 0° C. for 15 minutes and then the solution is allowed to warm to room temperature. After 3 hours the mixture is concentrated, dissolved in dichloromethane, and washed with aqueous NaHCO$_3$ (saturated) and brine. Drying over magnesium sulphate and concentration then gives Compound 60 as a mixture of 2 diastereoisomers at phosphorus.

$^{31}$P NMR $^{1}$H decoupled (CDCl$_3$, 162 MHz) δ 53.1, 52.1 ppm

EXAMPLE 64

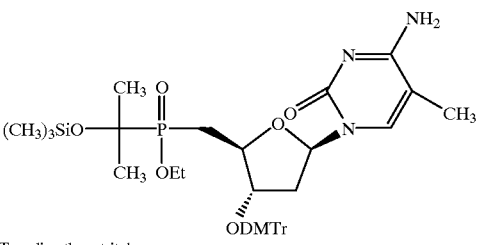

Compound 61

DMTr = dimethoxytrityl
Et = ethyl

Compound 60 (150 mg, 0.187 mmol) is dissolved in dioxan (2 ml) and concentrated (880) ammonia (0.5 ml) added. The resultant solution is stirred at room temperature for 16 hours and then concentrated followed by coevaporation from dioxan (2×10 ml). Purification by silica gel column chromatography (eluant:ethyl acetate-ethanol 7:1) gives Compound 61 as a mixture of 2 diastereoisomers at phosphorus.

$^{31}$P NMR $^{1}$H decoupled (CD$_3$OD, 162 MHz) δ 55.2, 54.6 ppm

EXAMPLE 65

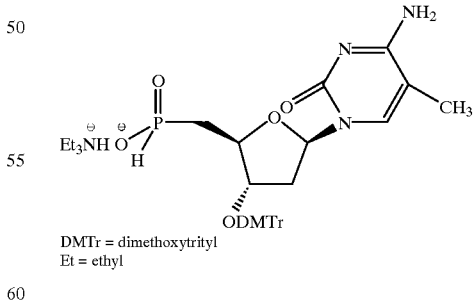

Compound 62

DMTr = dimethoxytrityl
Et = ethyl

Compound 62 is prepared by a method analogous to that used for the preparation of Compound 58 in Example 61, but using Compound 61 as starting material in place of Compound 57.

$^{31}$P NMR $^{1}$H decoupled (CD$_3$OD, 162 MHz) δ 22.0 ppm

EXAMPLE 66

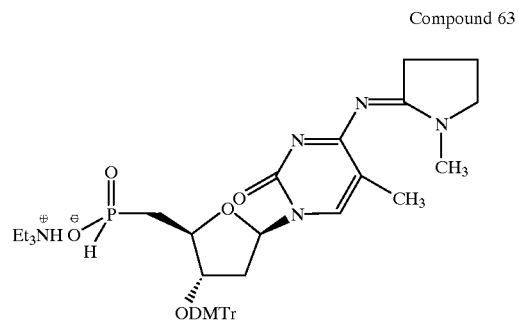

Compound 63

DMTr = dimethoxytrityl
Et = ethyl

To a solution of Compound 62 (0.55 g, 0.8 mmol) in dry methanol (10 ml) is added N-methylpyrrolidone dimethylacetal (0.57 g, 4.0 mmol) followed by triethylamine (0.3 ml). The resulting mixture is stirred at room temperature for 24 hours. Concentration and purification by silica (acid washed) column chromatography (gradient elution, chloroform:methanol:triethylamine 200:20:1–200:40:1) gives Compound 63.

$^{31}$P NMR $^1$H decoupled (CD$_3$OD, 162 MHz) δ 21.8 ppm

EXAMPLE 67

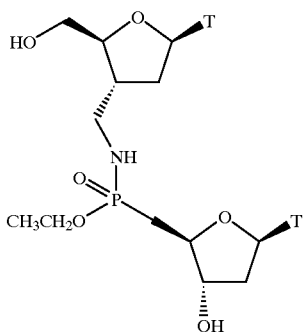

Compound 64

T = 1-thyminyl

Compound 64 is prepared by a method analogous to that used for Compound 47A in Example 49 but replacing Compound 46A by Compound 36. The crude product is purified by flash silica column chromatography (chloroform-methanol mixtures) to give Compound 64 as a 2:1 mixture of diastereoisomers.

Found C, 45.40; H, 6.20; N, 11.55%; C$_{23}$H$_{34}$N$_5$O$_{10}$P.2H$_2$O requires C, 45.45; H, 6.30; N, 11.55%.

$^{31}$P NMR $^1$H decoupled (CD$_3$OD, 162 MHz) δ 32.9, 32.7 ppm

EXAMPLE 68

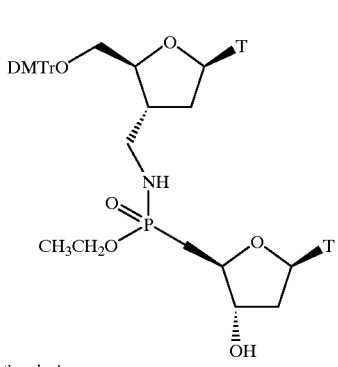

Compound 65

T = 1-thyminyl
DMTr = dimethoxytrityl

Compound 65 is prepared by a method analogous to that for Compound 42 in Example 43 but replacing Compound 41 used in that Example by Compound 64. The crude product is purified by flash silica column chromatography (eluant ether followed by chloroform ethanol mixtures containing 0.5% triethylamine) to give Compound 65 as a 2:1 mixture of diastereoisomers.

$^{31}$P NMR $^1$H decoupled (CDCl$_3$, 162 MHz) δ 32.9, 32.7 ppm

EXAMPLE 69

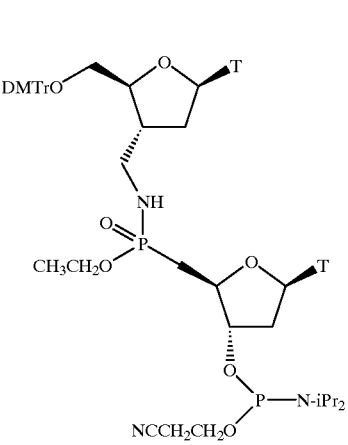

Compound 66

T = 1-thyminyl
DMTr = dimethoxytrityl
iPr = isopropyl

Compound 66 is prepared by a method analogous to that used for Compound 43 in Example 44, but replacing Compound 42 used in that Example by Compound 65. This gives Compound 66 as a 2:2:1:1 mixture of diastereoisomers.

$^{31}$P NMR $^1$H decoupled (CDCl$_3$, 101 MHz) δ 149.6, 149.4, 149.3, 31.3, 30.9, 30.6 ppm

EXAMPLE 70

Compound 67

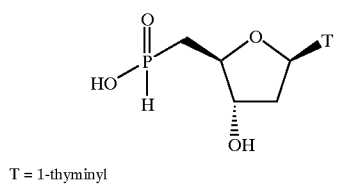

T = 1-thyminyl

To a solution of Compound 35 (7.5 g, 13.5 mmol) in dry THF (125 ml) is added a solution of tetra-n-butylammoniumfluoride (29.6 ml, 1.0 molar). After stirring for 3.5 hours at room temperature, additional tetra-n-butylammoniumfluoride (7 ml) is added. After a further 3 hours at room temperature and 72 hours at 0–5° C., the mixture is concentrated. The resulting solid is partitioned between water (50 ml) and ethyl acetate (100 ml). The aqueous layer is separated and purified by ion exchange chromatography (DOWEX 50W, acid form), eluting with water to give, after lipophilization, Compound 67.

Found C, 40.40; H, 5.10; N, 9.20%; $C_{10}H_{15}N_2O_6P.\frac{1}{2}H_2O$ requires C, 40.15; H, 5.40; N, 9.35%.

$^{31}P$ NMR $^1H$ decoupled ($D_2O$, 162 MHz) δ 30.0 ppm

EXAMPLE 71

Compound 68

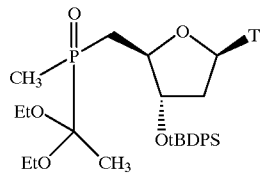

T = 1-thyminyl
Et = ethyl

To a solution of 1,1-diethoxyethyl methyl phosphine oxide (0.81 g, 4.5 mmol) in dry THF (20 ml) under argon at −78° C. is added potassium hexamethyl disilazide in toluene (15%, 6.0 ml, 4.5 mmol). The resulting solution is stirred at −78° C. for 45 minutes before the dropwise addition of a solution of Compound H (0.89 g, 1.5 mmol) in THF (5 ml). The resulting solution is stirred for 1 hour at −78° C. before slow warming to room temperature. Saturated aqueous ammonium chloride solution (5 ml) is then added, and the mixture extracted with ethyl acetate. The organic extracts are washed with brine, dried over sodium sulphate and concentrated. Purification by silica gel flash chromatography (eluant:ethyl acetate, ethanol mixtures) followed by further flash chromatography (eluant: dichloromethane:ethanol mixtures) gives Compound 68 as a 3:2 mixture of diastereoisomers.

Found C, 60.80; H, 7.50; N, 4.25%; $C_{33}H_{47}N_2O_7PSi.\frac{1}{2}H_2O$ requires C, 60.80; H, 7.40; N, 4.30%.

$^{31}P$ NMR $^1H$ decoupled ($CD_3OD$ 162 MHz) δ 46.2, 45.3 ppm

M/S (electrospray+ve mode) m/z 643.3 (100), δ 44.4 (50), 645.4 (18), 646.4 (4) MH+

EXAMPLE 72

Compound 69

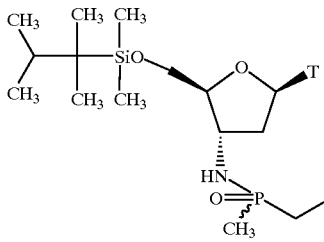

T = 1-thyminyl
Ph = phenyl

A solution of Compound Z (0.26 g, 0.66 mmol) and Compound ZA (0.20 g, 0.49 mmol) in pyridine is evaporated dry and the residue is dissolved in dichloromethane (1.0 ml) and pyridine (0.5 ml). Powdered 3A molecular sieves (0.24 g) are added and the mixture stirred for 10 minutes. Carbon tetrachloride (1.0 ml) and triethylamine (0.4 ml) are added. After 20 hours, the reaction mixture is evaporated and the residue purified by dry flash chromatography on 15–40 μm silica gel. The product is eluted using a gradient chloroform/ethanol (100:0–88:12) to give Compound 69 as a mixture of diastereoisomers.

$^{31}P$ NMR $^1H$ decoupled ($CDCl_3$, 161 MHz) δ 42.9, 42.4 ppm

Early and late fractions from the column contain pure diastereoisomers.

Early fraction:

$^{31}P$ NMR ($CDCl_3$, 161 MHz) δ 41.9 ppm $^1H$ NMR ($CDCl_3$, 400 MHz) δ 1.41 (d, J 13.4 Hz) ppm Late fraction:

$^{31}P$ NMR ($CDCl_3$, 161 MHz) δ 42.8 ppm $^1H$ NMR ($CDCl_3$, 400 MHz) δ 1.38 (d, J 13.4 Hz) ppm

EXAMPLE 73

A solution of Compound ZB (0.109 g, 0.222 mmol) and Compound 35 (0.103 g, 0.185 mmol) in pyridine (10 .ml) is cooled to −20° C. and then triethylamine (0.21 ml, 1.5 mmol) followed by carbon tetrachloride (0.3 ml) are added. After 15 minutes, the reaction is warmed to 0° C. over 1 hour and after a further hour allowed to warm to 20° C. After 21 hours the reaction mixture is evaporated and the residue purified by dry flash chromatography on 15–40 μm silica gel. The product, a mixture of diastereoisomers, is eluted by a gradient of chloroform/ethanol (100:0–92:8) to give Compound 36.

$^{31}P$ NMR $^1H$ decoupled ($CDCl_3$, 161 MHz) δ 30.8, 31.2 ppm

EXAMPLE 74

Example 1 is repeated using Compound ZG (220 mg, 325 μmol) place of Compound F, using Compound K (224 mg, 358 μmol) in place of Compound J, and using 431 μl (1.63 mmol) of BSTFA and 3.3 ml of pyridine instead of the amounts used in Example 1. The product is Compound 5.

EXAMPLE 75

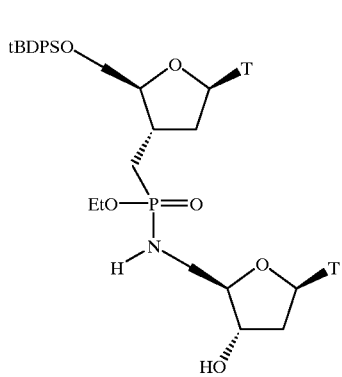

Compound 70

Example 1 is repeated using Compound D₁ (430 mg, 753 µmol) in place of Compound F and using 211 mg (791 µmol) of 5'-deoxy-5'-azidothymidine prepared according to procedure of E. B. McElroy and T. S. Widlanski J. Org. Chem. 1994 59 3520–3521 in place of Compound J, 1.20 ml (4.52 mmol) of BSTFA and 7.5 ml of pyridine instead of the amounts used in Example 1. Compound 70 is isolated as predominantly a single diastereomer.

$^{31}$P NMR (CDC$_3$, 162 MHz) δ 33.9 ppm.

EXAMPLE 76

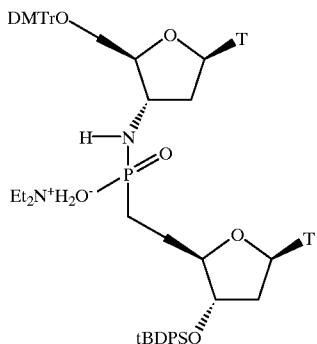

Compound 71

To a solution of Compound 31 as a 1:1 mixture of diastereomers (3.75 g, 331 mol) and butylamine (8.24 µl, 83 µmol) in 1 ml of THF is added palladium tetrakistriphenylphosphine (0.25 mg). After 15 minutes the reaction mixture is flash chromatographed on silica gel eluting with 3:1 ethyl acetate:methanol containing 1% diethylamine to give Compound 71 as a white amorphous solid.

$^{31}$P NMR (CDCl$_3$, 202 MHz) δ 25.1 ppm.

Found C, 63.17; H, 6.99; N, 7.00; C$_{62}$H$_{77}$N$_6$O$_{12}$PSi.H$_2$O requires C, 63.35; H, 6.77; N, 7.15.

EXAMPLE 77

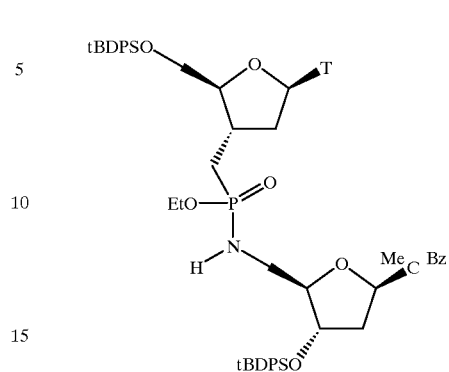

Compound 72

To a solution of Compound D₁ (399 mg, 699 µmol) and Compound ZO (447 mg, 734 µmol) in pyridine (7 ml) is added BSTFA (1.11 ml, 4.20 mmol) at 0° C. After 24 hours at room temperature methanol (10 ml) is added and the reaction mixture evaporated, taken-up into chloroform (12 ml) and methanol (4 ml) and refluxed for six hours. The reaction mixture is again evaporated and the crude product purified by flash column chromatography on silica gel eluting with 98% chloroform 2% methanol to give Compound 72 as predominantly a single diastereomer. Up to 20% of P-epimer is detectable.

$^{31}$P NMR (CDCl$_3$, 162 MHz) δ 32.2 ppm. Minor P-epimer component δ 31.6 ppm.

MS (ES) M/Z 1151 (MH⁺), 1173 (MNa⁺).

EXAMPLE 78

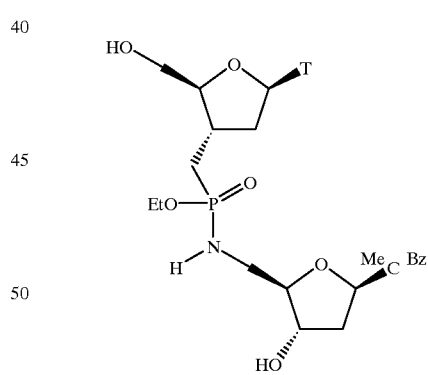

Compound 73

To a solution of Compound 72 (280 mg, 243 µmol) in THF (5 ml) is added 535 µl (535 µmol) of a 1.0M TBAF solution in THF at 0° C. After 4 hours at room temperature the reaction mixture is applied to a flash silica gel column and eluted with a gradient from chloroform to 80% chloroform 20% methanol to give Compound 73 as predominantly a single diastereomer.

$^{31}$P NMR (CDCl$_6$, 162 MHz) δ 36.40 ppm. Minor P-epimeric component δ 36.35 ppm.

MS (ES) M/Z 375 (MH⁺), 697 (MNa⁺).

EXAMPLE 79

Compounds 74 and 75

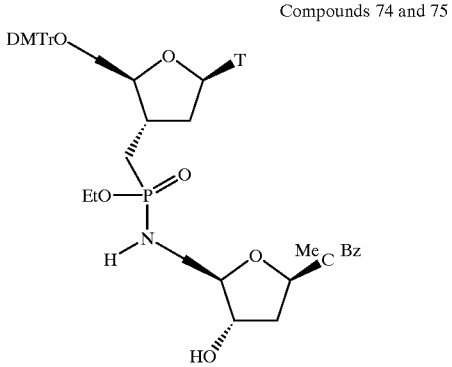

To a solution of Compound 73 (110 mg, 163 μmol) in pyridine (1.6 ml) is added dimethoxytrityl chloride (95 mg, 245 μmol) at 0° C. After 3 hours at room temperature methanol (2 ml) is added and the reaction mixture is evaporated. Purification by flash column chromatography using silica gel eluting with a gradient from CHCl$_3$ to 95% chloroform 5% methanol, all eluent contains 0.1% Et$_3$N gives a minor higher Rf component Compound 74 the P-epimer of the major lower Rf component Compound 75.

Compound 75

$^{31}$P NMR (CDCl$_3$, 202 MHz) δ 34.0 ppm. $^{31}$P NMR (CD$_2$Cl$_2$, 202 MHz) δ 34.0 ppm.

Found C, 61.28; H, 6.00; N, 8.33; C$_{51}$H$_{57}$N$_6$O$_{12}$P.H$_2$O requires C, 61.56; H, 5.98; N, 8.45.

Compound 74

$^{31}$P NMR (CDCl$_3$, 202 MHz) δ 33.9 ppm. $^{31}$P NMR (CD$_2$Cl$_2$, 202 MHz) δ 34.5 ppm.

Found C, 60.97; H, 5.91; N, 8.12; C$_{51}$H$_{57}$N$_6$O$_{12}$P.H$_2$O requires C, 61.56; H, 5.98; N, 8.45.

EXAMPLE 80

Compound 76

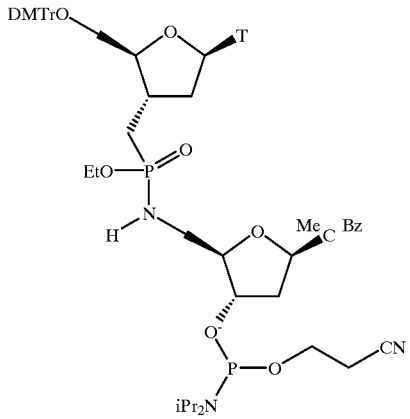

To a solution of Compound 75 (2.13 g, 2.13 mmol) and diisopropylammonium tetrazolide (1.87 g, 10.9 mmol) in dichloromethane (65 ml) is added 2-cyanoethyl bis-(diisopropylamino)-phosphordiamidite (1.97 g, 6.54 mmol) at 0° C. After 18 hours at room temperature the reaction mixture is partitioned between aqueous sodium hydrogen carbonate solution and dichloromethane and the organic layers dried over magnesium sulphate. The crude product is purified by flash column chromatography on silica gel eluting with 98% ethyl acetate 2% methanol with 0.1% triethylamine. Precipitation of a dichloromethane (20 ml) solution from pentane (500 ml) gives Compound 76 as a 1:1 mixture of diastereomers.

$^{31}$P NMR (CD$_2$Cl$_2$, 202 MHz) δ 150.9, 149.8, 32.8, 32.7 ppm.

Found C, 60.50; H, 6.39; N, 9.42; C$_{60}$H$_{74}$N$_8$O$_{13}$P$_2$.H$_2$O requires C, 60.29; H, 6.41; N, 9.37.

EXAMPLE 81

Compound 77

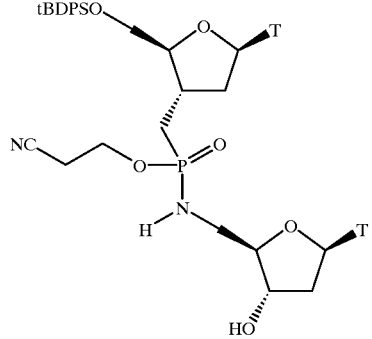

To a solution of Compound G (253 g, 424 μmol) and 5'-deoxy-5'-azido-thymidine (119 mg, 445 μmol) in pyridine (4 ml) is added BSTFA (674 mg, 2.54 mmol) at 0° C. After 18 hours at room temperature MeOH (5 ml) is added and the reaction mixture evaporated, taken-up in chloroform (3 ml) and methanol (2 ml) and refluxed for 4 hours. Purification by flash column chromatography eluting with 90% dichloromethane 10% methanol gives Compound 77 as a 1:1 mixture is of diastereomers.

$^{31}$P NMR (d$_4$-MeOH, 162 MHz) δ 37.0, 36.9 ppm.

Found C, 55.17; H, 6.32; N, 9.63; C$_{40}$H$_{51}$N$_6$O$_{10}$PSi.2H$_2$O requires C, 55.16; H, 6.37; N, 9.65.

EXAMPLE 82

Compound 78

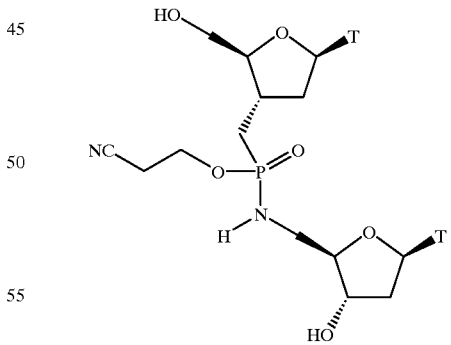

To a solution of Compound 77 (167 mg, 200 μmol) in THF (1 ml) is added trethylamine trihydrofluoride (645 mg, 4.0 mmol) at 0° C. Reaction mixture stirred 18 hours at room temperature and applied to flash column of silica gel, eluting with 60% chloroform 40% methanol to give Compound 78 as a 1:1 mixture of diastereomers.

$^{31}$P NMR (d$_4$-MeOH, 202 MHz) δ 37.5, 37.4 ppm.

MS (ES) M/Z 597 (MH$^+$), 619 (MNa$^+$).

EXAMPLE 83

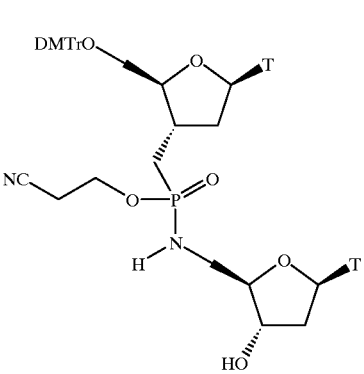

Compound 79

To a solution of Compound 78 (50 mg, 84 μmol) in pyridine (1 ml) is added dimethoxytritylchloride (41 mg, 105 μmol) at 0° C. After 6 hours at room temperature methanol (2 ml) is added and the reaction mixture evaporated. Purification by flash column chromatography eluting with 90% CHCl$_3$ 10% methanol containing 0.1% triethylamine gives Compound 79 as a 1:1 mixture of diastereomers.

$^{31}$P NMR (CDCl$_3$, 162 MHz) δ 35.1, 34.8 ppm.

MS (ES) M/Z 916 (MH$^+$), 921 (MNa$^+$).

EXAMPLE 84

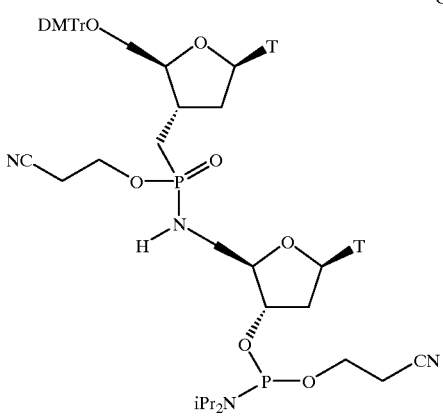

Compound 80

To a solution of Compound 79 (2.40 g, 2.67 mmol) and diisopropylammonium tetrazolide (2.29 g, 13.3 mmol) in dichloromethane (80 ml) is added 2-cyanoethyl bis-(diisopropylamino)-phosphordiamidite (2.41 g, 8.01 mmol) at 0° C. After 18 hours at room temperature the reaction mixture is partitioned between aqueous sodium hydrogen carbonate solution and dichloromethane and the organic layers dried over magnesium sulphate. Purification by flash column chromatography on silica gel eluting with 90% ethyl acetate 10% methanol containing 0.1% triethylamine gives Compound 80 as a 1:1:1:1 mixture of diastereomers.

$^{31}$P NMR (CDCl$_3$, 202 MHz) δ 150.66, 150.55, 149.91, 149.77, 35.13, 35.08, 34.22, 34.11 ppm.

Found C, 57.67; H, 6.35; N, 10.12; C$_{54}$H$_{68}$N$_8$O$_{13}$P$_2$.H$_2$O requires C, 58.05; H, 6.33; N, 10.03.

MS (ES) M/Z 1099 (MH$^+$), 1116 (MNH$_4^+$), 1121 (MNa$^+$).

Compound 85

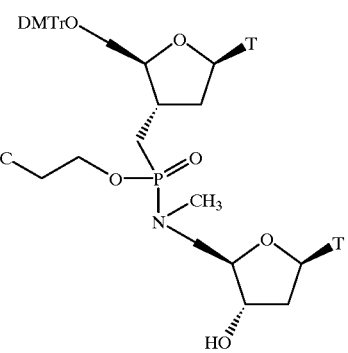

Compound 81

To a suspension of 3A molecular sieves (204 mg) in a solution of Compound ZQ (270 mg, 409 μmol) and Compound ZR (261 mg, 1.02 mmol) in pyridine (818 μl) and dichloromethane (1.64 ml) is added carbon tetrachloride (805 μl) followed by triethylamine (309 μl) at room temperature. After 4 hours, the reaction mixture is filtered, washed with aqueous sodium hydrogen carbonate solution and dried over magnesium sulphate. Purification by flash column chromatography on silica gel eluting with 90% dichloromethane 10% methanol containing 0.1% triethylamine gives Compound 81 as a 1:1 mixture of diastereomers.

$^{31}$P NMR (d$_6$-acetone, 162 MHz) δ 37.1, 36.7 ppm.

MS (ES) M/Z 913 (MH$^+$), 930 (MNH$_4^+$), 935 (MNa$^+$).

EXAMPLE 86

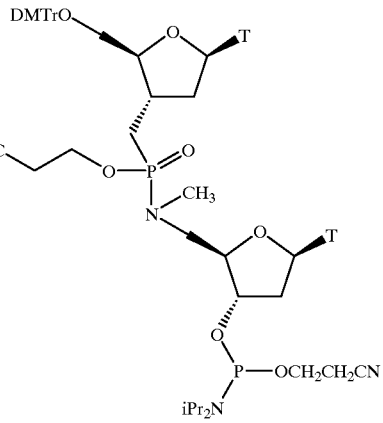

Compound 82

To a solution of Compound 81 (325 mg, 356 μmol) and diisopropylammonium tetrazolide (305 mg, 1.78 mmol) in dichloromethane (10.7 ml) is added 2-cyanoethyl bis-(diisopropyl-amino)-phosphordiamidite (322 mg, 1.07 mmol) at 0° C. After 18 hours at room temperature the reaction mixture is partitioned between aqueous sodium hydrogen carbonate solution and dichloromethane and the organic layers dried over magnesium sulphate. Purification by flash column chromatography on silica gel eluting with 90% ethyl acetate 10% methanol containing 0.1% triethylamine gives Compound 82 as a 1:1:1:1 mixture diastereomers.

$^{31}$P NMR (d$_6$-acetone, 162 MHz) δ 150.31, 150.22, 149.75, 149.64, 36.76, 36.58, 36.36, 36.30 ppm.

Found C, 58.28; H, 6.38; N, 9.76; $C_{55}H_{70}N_8O_{13}P_2 \cdot H_2O$ requires C, 58.39; H, 6.43; N, 9.91.

MS (ES) M/Z 1113 (MH$^+$), 1130 (MNH$_4^+$), 1135 (MNa$^+$).

EXAMPLE 87

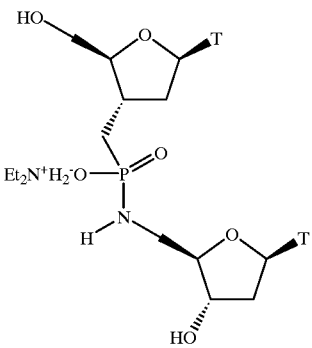

Compound 83

To a solution of Compound 78 (74 mg, 124 μmol) in water (800 μl) is added 880 ammonia solution (800 μl) at room temperature. After 5 hours diethylamine (250 μl) is added and the reaction mixture evaporated to give Compound 83.

$^{31}$P NMR (D$_2$O, 202 MHz) δ 26.6 ppm.

EXAMPLE 88

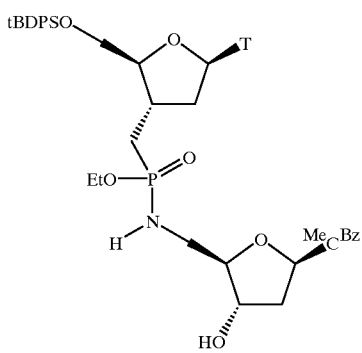

Compound 84

To a solution of Compound D$_1$ (399 mg, 699 μmol) and Compound ZS (259 mg, 699 μmol) in pyridine (7 ml) is added BSTFA (1.11 ml, 4.19 mmol) at 0° C. After 18 hours at room temperature methanol (10 ml) is added and the reaction mixture evaporated, taken-up into chloroform (12 ml) and methanol (4 ml) and refluxed for six hours. The reaction mixture is again evaporated and the crude product purified by flash column chromatography on silica gel eluting with 95% ethyl acetate 5% ethanol to give Compound 84 as predominantly a single diastereomer.

$^{31}$P NMR (d$_4$-MeOH, 162 MHz) δ 36.4 ppm. Minor P-epimeric component δ 36.3 ppm.

EXAMPLE 89

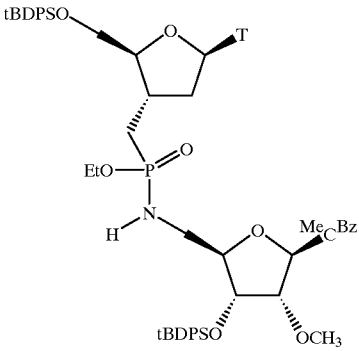

Compound 85

To a solution of Compound D$_1$ (2.0 g, 3.50 mmol) and Compound ZL (2.35 g, 3.68 mmol) in pyridine (40 ml) is added BSTFA (5.61 ml, 21.0 mmol) at 0° C. After 24 hours at room temperature methanol (20 ml) is added and the reaction mixture evaporated, taken-up in chloroform (9 ml) and methanol (6 ml) and refluxed for 5 hours. Purification by flash column chromatography on silica gel eluting with 95% ethyl acetate 5% methanol gives Compound 85 as predominantly a single diastereomer.

$^{31}$P NMR (CDCl$_3$, 202 MHz) δ 32.7 ppm. Minor P-epimeric component δ 31.7 ppm.

EXAMPLE 90

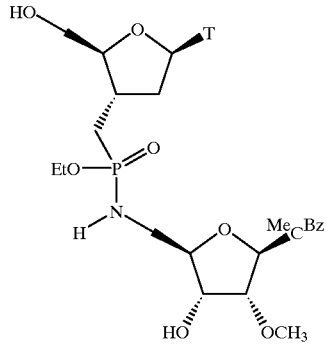

Compound 86

Example 6 is repeated using Compound 85 (529 mg, 448 μmol) in place of Compound 1 and using 10 ml THF and 985 μl of the 1.0M TBAF solution instead of the amounts used in Example 6. The product is Compound 86 as predominantly a single diastereomer.

$^{31}$P NMR (d$_4$-MeOH, 202 MHz) δ 36.5 ppm. Minor P-epimeric component δ 36.4 ppm.

EXAMPLE 91

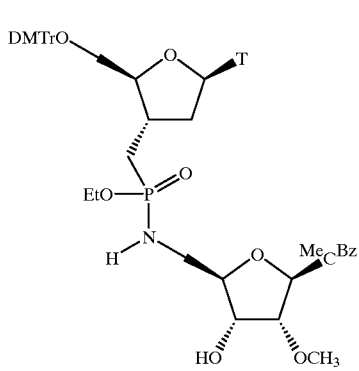

Compound 87

Example 9 is repeated using Compound 86 (2.3 g, 3.26 mmol) in place of Compound 6 and using 1.32 g (3.91 mmol) of dimethoxytrityl chloride and 30 ml of pyridine instead of the amounts used in Example 9. Purification by flash column chromatography on silica gel gives Compound 87 as a single diastereomer.

$^{31}$P NMR (d$_6$-acetone, 202 MHz) δ 33.9 ppm.

Found C, 61.01; H, 6.12; N, 7.95; $C_{52}H_{59}N_6O_{13}P.H_2O$ requires C, 60.90; H, 5.99; N, 8.19.

EXAMPLE 92

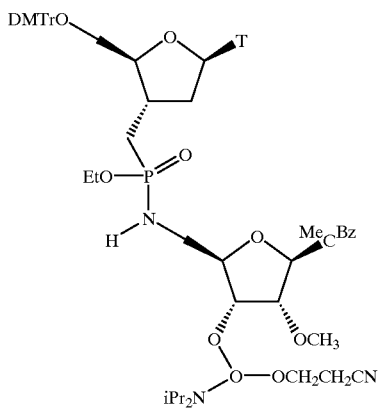

Compound 88

Example 12 is repeated using Compound 87 (1.82 g, 1.81 mmol) in place of Compound 9 and using 1.55 g (9.05 mmol) of diisopropylammonium tetrazolide and 1.73 ml (5.43 mmol) of 2-cyanoethyl bis-(diisopropylamino)-phosphordiamidite and 40 ml dichloromethane in place of the amounts used in Example 12. The product is Compound 88 as a 1:1 mixture of diastereomers.

$^{31}$P NMR (d$_6$-acetone, 202 MHz) δ 151.6, 150.9, 37.7, 37.7 ppm.

EXAMPLE 93

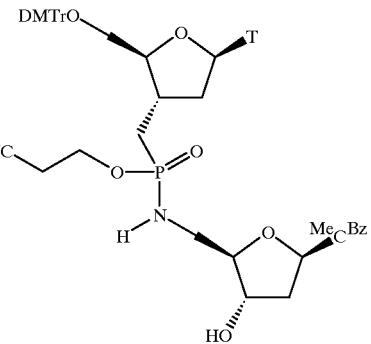

Compound 89

To a suspension of 3A molecular sieves (1.2 g) in a solution of Compound ZQ (1.58 g, 2.40 mmol) and Compound ZT (1.24 g, 3.59 mmol) in pyridine (4.8 ml) and dichloromethane (9.6 ml) is added carbon tetrachloride (4.7 ml) followed by triethylamine (1.8 ml) at room temperature. After 2 hours the reaction mixture is filtered, diluted with dichloromethane and washed with aqueous sodium hydrogen carbonate solution. The crude product is purified by flash column chromatography on silica gel eluting with 90% chloroform 10% methanol containing 0.1% triethylamine to give Compound 89 as a 1:1 mixture of diastereomers.

$^{31}$P NMR (CDCl$_3$, 162 MHz) δ 34.9, 34.7 ppm.

EXAMPLE 94

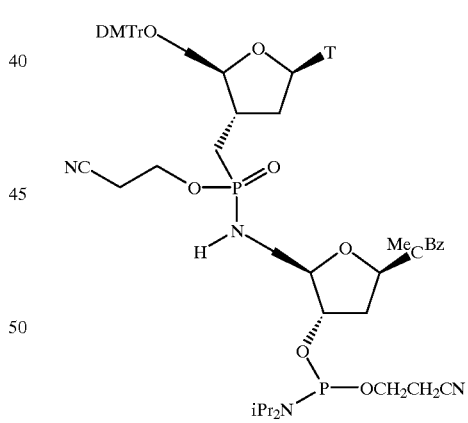

Compound 90

Example 12 is repeated using Compound 89 (2.0 g, 1.99 mmol) in place of Compound 9 and using 1.71 g (9.98 mmol) of diisopropylammonium tetrazolide and 1.80 g (5.99 mmol) of 2-cyanoethyl bis-(diisopropylamino)-phosphordiamidite and 60 ml DCM in place of the amounts used in Example 12. The product is Compound 90 as a 1:1:1:1 mixture of diastereomers.

$^{31}$P NMR (CDC$_3$, 162 MHz) δ 150.53, 150.28, 149.25, 149.05, 34.32, 34.26, 33.44, 35.35 ppm.

EXAMPLE 95

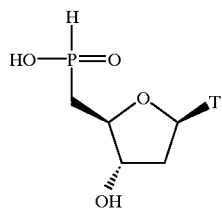

Compound 91

To a solution of Compound 35 (7.5 g, 13.5 mmol) in THF (125 ml) is added tetra n butylammonium fluoride (29.6 ml, 29.6 mmol, 1 molar solution). After 3.5 hours at room temperature additional tetra n butylammonium fluoride is added (7 ml). The mixture is stood at 5° C. for 60 hours and then concentrated and purified by passage through a Dowex 50W acid form resin eluting with water. The product is then isolated by freeze drying to give a white solid.

Found C, 40.40; H, 5.10; N, 9.25; $C_{10}H_{15}N_2O_6P\cdot\frac{1}{2}H_2O$ requires C, 40.15; H, 5.40; N, 9.35.

$^{31}P$ NMR $^1H$ decoupled ($D_2O$, 202 MHz) δ 35.4 ppm.

EXAMPLE 96

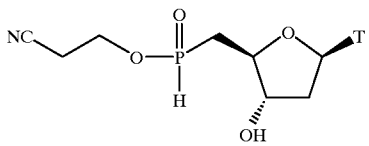

Compound 92

To a solution of compound 91 (0.71 g, 2.45 mmol) in dry THF (7.5 ml) is added DCC (0.76 g, 3.68 mmol) and dimethylaminopyridine (5 mg) followed by 3-hydroxyproponitrile (1.66 ml, 24.3 mmol). The resulting mixture is heated at 80° C. for 3 hours under an argon atmosphere. The mixture is then cooled, diluted with THF and filtered. Concentration then gives the crude product containing excess 3-hydroxyproponitrile. Compound 92 is unstable to column chromatography and is thus not purified any further.

$^{31}P$ NMR $^1H$ decoupled ($CDCl_3$, 202 MHz) δ 39.0 and 38.9 ppm.

EXAMPLE 97

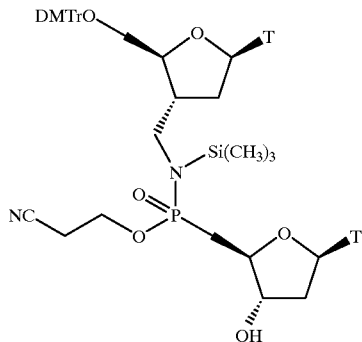

Compound 93

To a solution of compound ZJ (1 g, 1.71 mmol) in pyridine (4 ml) is added fluorobistrimethylsilyl-trifluoroacetamide (13 ml) with stirring and cooling at 0° C. under argon atmosphere over 10–15 mins. The resulting mixture is allowed to warm to rt during the addition of a solution of crude product from the previous example in pyridine (5 ml). The resulting mixture is stirred at rt for 23 h and concentrated. Purification by flash silica column chromatography (eluant 1:1 ethyl acetate:hexane then ethyl acetate then 10:1 ethyl acetate:methanol) gives compound 93 albeit impure. This product was used directly in the next example.

EXAMPLE 98

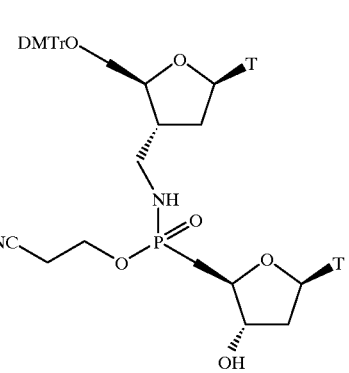

Compound 94

To a solution of compound 93 (0.425 g, 0.44 mmol) in THF (30 ml) is added triethylamine trihydro fluoride (450 μl, 2.8 mmol) at 10° C. under argon. The solution is allowed to warm to rt and is concentrated after 2 h and purified by flash silica column chromatography (gradient elution ethyl acetate:methanol 100:1–8:1) to give compound 94 as a mixture of 2 diastereomers at phosphorus.

$^{31}P$ NMR $^1H$ decoupled ($CDCl_3$, 162 MHz) δ 35.35, 35.3 ppm.

EXAMPLE 99

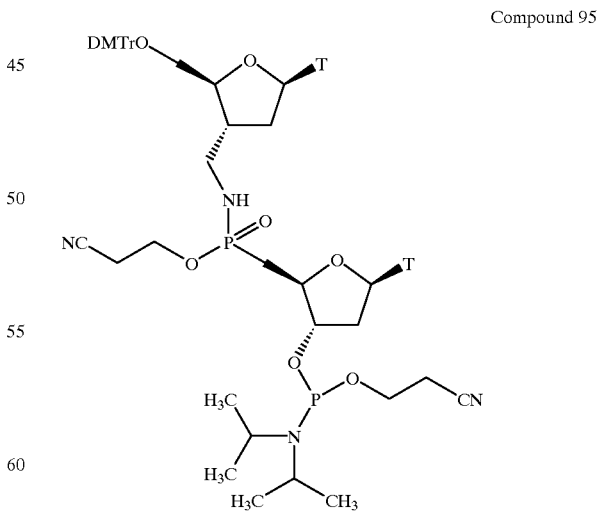

Compound 95

Compound 95 is prepared by the general method of Example 44 but using Compound 94 in place of Compound 42. After drying the crude product is purified by flash silica column chromatography (gradient elution ethyl acetate—ethyl acetate:methanol 10:1, plus 0.1% triethylamine) to give Compound 95 as a mixture of 4 diastereomers at phosphorus.

$^{31}P$ NMR $^1H$ decoupled (CDCl$_3$, 202 MHz) δ 150.1, 150.5, 149.9, 149.8, 33.9, 33.6, 33.4, 33.1 ppm.

EXAMPLES 100–139

Oligonucleotides are prepared from dinucleotides prepared in previous Examples and similarly DMTr-protected and phosphoramidite-activated natural nucleosides -2'-deoxyadenosine (dA), -2'-deoxyadcytidine (dC), -2'-deoxyguanosine (dG) and thymidine (dT) - on an ABI 390 automatic DNA synthesizer (available from Applied Biosystems Inc) using standard phosphoramidite chemistry according to Oligonucleotide Synthesis: A Practical Approach, M. J. Gait, IRL Press, Oxford 1984, but with prolonged coupling times (10 minutes). DMTr oligonucleotides are purified by reverse phase HPLC (eluant A=50 mM triethylammonium acetate (TEAA), pH 7.0; eluant B:50 mM TEAA, pH7.0 in 70% acetonitrile; elution with gradient from 15% to 45% B in 45 minutes). After purification by HPLC, the DMTr protective group is removed by treatment with 80% aqueous acetic acid and the oligonucleotides are precipitated with ethanol and isolated by centrifiguration. The purity of the oligodeoxynucleotides is checked by capillary gel electrophoresis (polyacrylamide; buffer; 100 mM H$_3$PO$_4$, 100 mM Tries, 2 mM ethylenediaminetetracetic acid, 7M urea, pH 8.8).

In most cases the structure of the oligodeoxynucleotides is checked by matrix assisted laser-desorption time-of-flight (MALDI-TOF) mass spectroscopy; the oligonucleotides being desorbed using 2,4,6-trihydroxyacetophenone as a matrix with diammonium hydrogen citrate as additive (25 mM final concentration) (U. Pieies et al, Nucl. Acids Res. 1993, 21, 3191).

The prepared oligonucleotide sequences are as follows:

5' TTT T*TC TCT CTC TCT 3'

T*T indicating the unit derived from the modifying dinucleotide.

| Example | Modifying dinucleotide Compound | TOF MS Calculated | Found |
|---|---|---|---|
| 100 | 12 | | |
| 101 | 13 | 4451 | 4451.2 |
| 102 | 14 | 4451 | 4455 |
| 103 | 43 | | |
| 104 | 66 | | |
| 105 | 53A | 4481 | 4475.2 |
| 106 | 53B | | |
| 107 | 49A | 4451 | 4450.4 |
| 108 | 49B | 4451 | 4449.3 |
| 109 | 33A | 4463 | 4463.4 |
| 110 | 33B | 4463 | 4466.6 |
| 111 | 20A | 4451 | 4447 |
| 112 | 20B | 4451 | 4453.3 |
| 113 | 95 | | |
| 114 | 80 | | |
| 115 | 82 | | |

5' GCG T*TT T*TT TT*T GCG 3'

T*T indicating the unit derived from the modifying dinucleotide

| Example | Modifying dinucleotide Compound | TOF MS Calculated | Found |
|---|---|---|---|
| 116 | 12 | | |
| 117 | 13 | 5000.5 | 5008.2 |
| 118 | 14 | | |
| 119 | 53A | | |
| 120 | 53B | 5150.7 | 5144.4 |
| 121 | 49A | 5000.5 | 4993.9 |
| 122 | 49B | | |
| 123 | 33A | 5060.7 | 5053.2 |
| 124 | 33B | 5060.7 | 5058.7 |
| 125 | 20A | 5000.5 | 5000.2 |
| 126 | 20B | 5000.5 | 5008.3 |
| 127 | 95 | | |
| 128 | 80 | | |
| 129 | 82 | | |

5' T*TT* TT*C T*CT* CT*C T*CT 3' where T*T and T*C indicate units derived from the modifying dinucleotides.

| Example | Modifying dinucleotide Compound | TOF MS Calculated | Found |
|---|---|---|---|
| 130 | 53B and 88 | | |

In the following sequences, T*T and T*C indicate units derived from the modifying dinucleotides and s indicates a phosphorothioate internucleoside linkage.

5'- T*TsCs T*CsGs CsCsCs GsCsTs CsCsT* CsCsT* CsC 3'

| Example | Modifying dinucleotide Compound | TOF MS Calculated | Found |
|---|---|---|---|
| 131 | 14 and 76 | 6275.3 | 6271.3 |
| 132 | 538 and 88 | 6393.3 | 6395.5 |
| 133 | 80 and 90 | | |

5'- T*TC T*CsGs CsCsCs GsCsTs CsCsT* CCT* CC 3'

| Example | Modifying dinucleotide Compound | TOF MS Calculated | Found |
|---|---|---|---|
| 134 | 53B and 88 | 6313 | 6311.8 |

5' TsT*Cs T*CsGs CsTsGs GsTsGs AsGsT* TsT*Cs A 3'

| Example | Modifying dinucleotide Compound | TOF MS Calculated | Found |
|---|---|---|---|
| 135 | 14 and 76 | 6168.2 | 6157.1 |
| 136 | 53B and 88 | 6286 | 6284.3 |
| 137 | 80 and 90 | | |

5' TT*C T*CsGs CsTsGs GsTsGs AsGsT* TT*C A 3'

| Example | Modifying dinucleotide Compound | TOF MS Calculated | Found |
|---|---|---|---|
| 138 | 53B and 88 | 6238 | 6239.2 |
| 139 | 14 and 76 | 6120 | 6109.5 |

We claim:

1. A method of preparing a compound of formula I

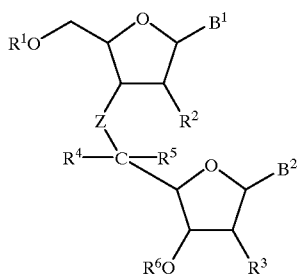

where $B^1$ and $B^2$ are each independently a monovalent nucleoside base radical, $R^1$ is hydrogen or $Y^1$, $R^2$ and $R^3$ are each independently hydrogen, halogen, halogen, hydroxy or $-OY^2$, $R^4$ is hydrogen, halogen, hydroxy, $-OY^3$ or $R^7$, $R^5$ is hydrogen, halogen or $R^8$, $R^6$ is hydrogen, $Y^4$ or a phosphoramidyl group, Z is a group of formula II

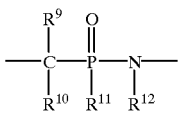

where $R^9$ is hydrogen, halogen, hydroxy, $-OY^5$ or $R^{13}$, $R^{10}$ is hydrogen, halogen or $R^{14}$, $R^{11}$ is hydroxy, $R^{15}$ or $-OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}{}_a$ or $-COR^{12}{}_a$ where $R^{12}{}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each independently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, which comprises reacting a compound of formula VIII

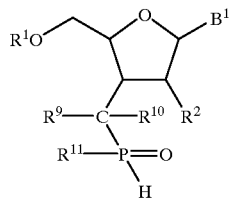

with a compound of formula IX

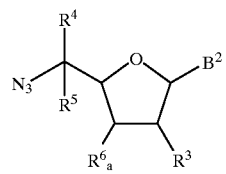

where $B^1$, $B^2$, $R^1$, $R^2$, $R^3$, $R^4$, $R^5$, $R^9$, $R^{10}$ and $R^{11}$ are as defined above and $R^6{}_a$ is hydrogen or $Y^4$ as defined above to give a compound of formula I where $R^{12}$ is hydrogen and, optionally, reacting the product to replace $R^{12}$ as hydrogen by $R^{12}$ as $R^{12}{}_a$, where $R^{12}{}_a$ is as defined above and/or reacting the product where $R^{12}$ is hydrogen or $R^{12}{}_a$ to replace one or more protecting groups by a hydrogen atom.

2. A method of preparing a compound of formula I

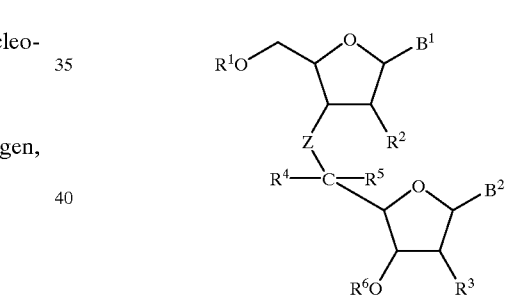

where $B^1$ and $B^2$ are each independently a monovalent nucleoside base radical, $R^1$ is hydrogen or $Y^1$, $R^2$ and $R^3$ are each independently hydrogen, halogen, hydroxy or $-OY^2$, $R^4$ is hydrogen, halogen, hydroxy, $-OY^3$ or $R^7$, $R^5$ is hydrogen, halogen or $R^8$, $R^6$ is hydrogen, $Y^4$ or a phosphoramidyl group, Z is a group of formula II

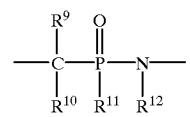

where $R^9$ is hydrogen, halogen, hydroxy, $-OY^5$ or $R^{13}$, $R^{10}$ is hydrogen, halogen or $R^{14}$, $R^{11}$ is hydroxy, $R^{15}$ or $-OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}{}_a$ or —$COR^{12}{}_a$ where $R^{12}{}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each independently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, which comprises reacting a compound of formula VIII

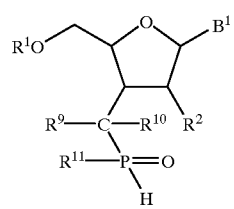

VIII with a compound of formula XXI

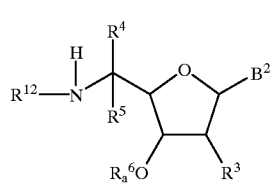

XXI and carbon tetrachloride or trichlorobromomethane in the presence of a tertiary amine, where $B^1$, $B^2$, $R^1$, $R^2$, $R^3$, $R^4$, $R^5$, $R^9$, $R^{10}$, $R^{11}$ and $R^{12}$ are as defined above and $R^6{}_a$ is hydrogen or $Y^4$ as defined above and, optionally, where $R^{12}$ is hydrogen, reacting the product to replace $R^{12}$ as hydrogen by $R^{12}$ as $R^{12}{}_a$, where $R^{12}{}_a$ is as defined above and/or reacting the product where $R^{12}$ is hydrogen or $R^{12}{}_a$ to replace one or more protecting groups by a hydrogen atom.

3. A method of preparing a compound of formula I

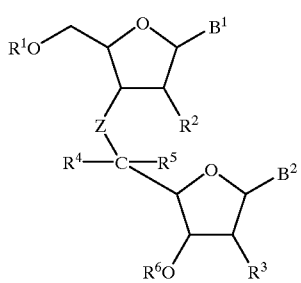

I where

B$^1$ and B$^2$ are each independently a monovalent nucleoside base radical, $R^1$ is hydrogen or $Y^1$, $R^2$ and $R^3$ are each independently hydrogen, halogen, hydroxy or —$OY^2$, $R^4$ is hydrogen, halogen, hydroxy, —$OY^3$ or $R^7$, $R^5$ is hydrogen, halogen or $R^8$, $R^6$ is hydrogen, $Y^4$ or a phosphoramidyl group, Z is a group of formula III

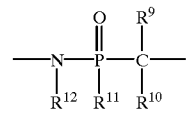

III where $R^9$ is hydrogen, halogen, hydroxy, —$OY^5$ or $R^{13}$, $R^{10}$ is hydrogen, halogen or $R^{14}$, $R^{11}$ is hydroxy, $R^{15}$ or —$OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}{}_a$ or —$COR^{12}{}_a$ where $R^{12}{}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each independently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, which comprises reacting a compound of formula XXII

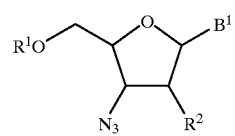

XXII with a compound of formula XXIII

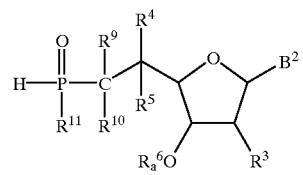

XXIII where $B^1$, $B^2$, $R^1$, $R^2$, $R^3$, $R^4$, $R^5$, $R^9$, $R^{10}$ and $R^{11}$ are as defined above and $R^6{}_a$ is hydrogen or $Y^4$ as defined above to give a compound of formula I in which $R^{12}$ is hydrogen and, optionally, reacting the compound where $R^{12}$ is hydrogen to give a compound where $R^{12}$ is $R^{12}{}_a$ as defined above and/or reacting the compound where $R^{12}$ is hydrogen or the compound where $R^{12}$ is $R^{12}{}_a$ to replace one or more protecting groups by hydrogen.

4. A method of preparing a compound of formula I

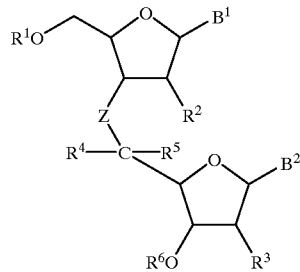

I where

B$^1$ and B$^2$ are each independently a monovalent nucleoside base radical, $R^1$ is hydrogen or $Y^1$, $R^2$ and $R^3$ are each independently hydrogen, halogen, hydroxy or $-OY^2$, $R^4$ is hydrogen, halogen, hydroxy, $-OY^3$ or $R^7$, $R^5$ is hydrogen, halogen or $R^8$, $R^6$ is hydrogen, $Y^4$ or a phosphoramidyl group, Z is a group of formula III

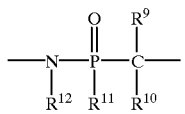

III where $R^9$ is hydrogen, halogen, hydroxy, $-OY^5$ or $R^{13}$, $R^{10}$ is hydrogen, halogen or $R^{14}$, $R^{11}$ is hydroxy, $R^{15}$ or $-OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}_a$ or $-COR^{12}_a$ where $R^{12}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each independently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, which comprises reacting a compound of formula XXV

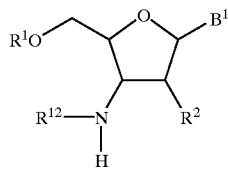

XXV where $B^1$, $R^1$, $R^2$ and $R^{12}$ are as defined above, with carbon tetrachloride or trichlorobromomethane and a compound of formula XXIII

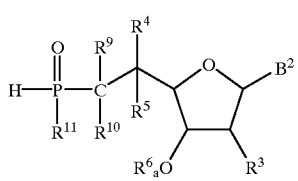

XXIII where $B^2$, $R^3$, $R^4$, $R^5$, $R^9$, $R^{10}$ and $R^{11}$ are as defined above and $R^6_a$ is hydrogen or $Y^4$ as defined above and, optionally, where $R^{12}$ is hydrogen, reacting the product to replace $R^{12}$ as hydrogen by $R^{12}$ as $R^{12}_a$, where $R^{12}_a$ is as defined above, and/or reacting the product where $R^{12}$ is hydrogen or the product where $R^{12}$ is $R^{12}_a$ to replace one or more protecting groups by hydrogen.

5. A method of preparing a compound of formula I

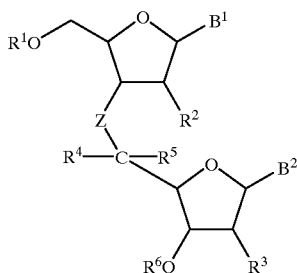

I where $B^1$ and $B^2$ are each independently a monovalent nucleoside base radical, $R^1$ is hydrogen or $Y^1$, $R^2$ and $R^3$ are each independently hydrogen, halogen, hydroxy or $-OY^2$, $R^4$ is hydrogen, halogen, hydroxy, $-OY^3$ or $R^7$, $R^5$ is hydrogen, halogen or $R^8$, $R^6$ is hydrogen, $Y^4$ or a phosphoramidyl group, Z is a group of formula IV

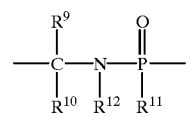

IV where $R^9$ is hydrogen, halogen, hydroxy, $-OY^5$ or $R^{13}$, $R^{10}$ is hydrogen, halogen or $R^{14}$, $R^{11}$ is hydroxy, $R^{15}$ or $-OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}_a$ or $-COR^{12}_a$ where $R^{12}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each independently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, which comprises reacting a compound of formula XXVI

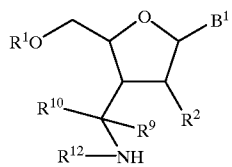

XXVI with carbon tetrachloride or bromotrichloromethane and a compound of formula XXVII

XXVII

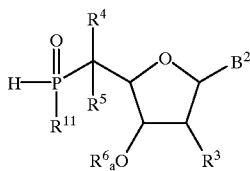

where $B^1$, $B^2$, $R^1$, $R^2$, $R^3$, $R^4$, $R^5$, $R^9$, $R^{10}$, $R^{11}$ and $R^{12}$ are as defined above and $R^6_a$ is hydrogen or $Y^4$ as defined above and, optionally, where $R^{12}$ is hydrogen, reacting the product to replace $R^{12}$ as hydrogen by $R^{12}$ as $R^{12}_a$, where $R^{12}_a$ is as defined above, and/or reacting the product where $R^{12}$ is hydrogen or $R^{12}_a$ to replace one or more protecting groups by hydrogen.

6. A method of preparing a compound of formula I

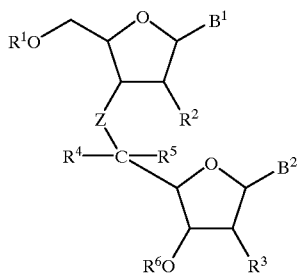

where $B^1$ and $B^2$ are each independently a monovalent nucleoside base radical, $R^1$ is hydrogen or $Y^1$, $R^2$ and $R^3$ are each independently hydrogen, halogen, hydroxy or —$OY^2$, $R^4$ is hydrogen, halogen, hydroxy, —$OY^3$ or $R^7$, $R^5$ is hydrogen, halogen or $R^8$, $R^6$ is hydrogen, $Y^4$ or a phosphoramidyl group, Z is a group of formula IV

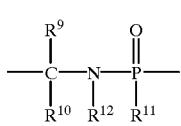

where $R^9$ is hydrogen, halogen, hydroxy, —$OY^5$ or $R^{13}$, $R^{10}$ is hydrogen, halogen or $R^{14}$, $R^{11}$ is hydroxy, $R^{15}$ or —$OR^{15}$ where $R^{15}$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, and $R^{12}$ is hydrogen, $R^{12}_a$ or —$COR^{12}_a$ where $R^{12}_a$ is a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, $Y^1$, $Y^2$, $Y^3$, $Y^4$ and $Y^5$ are each independently a hydroxy-protecting group, and $R^7$, $R^8$, $R^{13}$ and $R^{14}$ are each independently a $C_1$ to $C_{10}$ aliphatic group, a $C_3$ to $C_8$ cycloaliphatic group, a $C_6$ to $C_{10}$ aromatic group or a $C_7$ to $C_{13}$ araliphatic group, which comprises reacting a compound of formula XXVIII

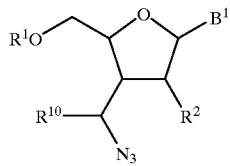

where $B^1$, $R^1$, $R^2$ and $R^{10}$ are as defined above, with a compound of formula XXVII

XXVII

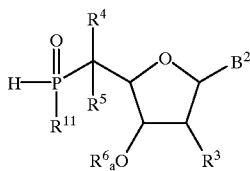

where $B^2$, $R^3$, $R^4$, $R^5$ and $R^{11}$ are as defined above, and $R^6_a$ is hydrogen or $Y^4$ as defined above, to give a compound of formula I where $R^{12}$ is hydrogen and, optionally, reacting this compound to replace $R^{12}$ as hydrogen by $R^{12}$ as $R^{12}_a$ where $R^{12}_a$ is as defined above and/or reacting the compound of formula I where $R^{12}$ is hydrogen or $R^{12}_a$ to replace one or more protecting groups by hydrogen.

7. A method of preparing a compound of claim 2 in which $R^6$ is a phosphoramidyl group which comprises reacting a compound of formula I where $R^6$ is hydrogen with an aliphatic bis(N,N-dialkyl)phosphordiamidite in the presence of an ammonium tetrazolide, or with an aliphatic N,N-dialkylchlorophosphoramidite in the presence of an organic base.

8. A method of preparing a compound of claim 3 in which $R^6$ is a phosphoramidyl group which comprises reacting a compound of formula I where $R^6$ is hydrogen with an aliphatic bis(N,N-dialkyl)phosphordiamidite in the presence of an ammonium tetrazolide, or with an aliphatic N,N-dialkylchlorophosphoramidite in the presence of an organic base.

9. A method of preparing a compound of claim 4 in which $R^6$ is a phosphoramidyl group which comprises reacting a compound of formula I where $R^6$ is hydrogen with an aliphatic bis(N,N-dialkyl)phosphordiamidite in the presence of an ammonium tetrazolide, or with an aliphatic N,N-dialkylchlorophosphoramidite in the presence of an organic base.

10. A method of preparing a compound of claim 5 in which $R^6$ is a phosphoramidyl group which comprises reacting a compound of formula I where $R^6$ is hydrogen with an aliphatic bis(N,N-dialkyl)phosphordiamidite in the presence of an ammonium tetrazolide, or with an aliphatic N,N-dialkylchlorophosphoramidite in the presence of an organic base.

11. A method of preparing a compound of claim 6 in which $R^6$ is a phosphoramidyl group which comprises reacting a compound of formula I where $R^6$ is hydrogen with an aliphatic bis(N,N-dialkyl)phosphordiamidite in the presence of an ammonium tetrazolide, or with an aliphatic N,N-dialkylchlorophosphoramidite in the presence of an organic base.

12. A method according to claim 1, in which the reaction between the compounds of formulae VIII and IX is carried out in a non-protic organic solvent, in the presence of a silylating agent.

13. A method according to claim 2, in which the reaction is carried out in dichloromethane or a mixture thereof with pyridine and at a temperature from −20 to 70° C.

14. A method according to claim 3, in which the reaction is carried out in a non-protic solvent in the presence of a silylating agent.

15. A method according to claim 4, in which the reaction is carried out in dichloromethane or a mixture thereof with pyridine at a temperature from −20 to 70° C.

16. A method according to claim 5 in which the reaction is carried out in dichloromethane or a mixture with pyridine at a temperature from −20 to 70° C.

17. A method according to claim 6, in which the reaction is carried out in a non-protic solvent in the presence of a silylating agent.

18. A method of preparing a compound of claim 1 in which $R^6$ is a phosphoramidyl group which comprises reacting a compound of formula I where $R^6$ is hydrogen with an aliphatic bis(N,N-dialkyl)phosphordiamidite in the presence of an ammonium tetrazolide, or with an aliphatic N,N-dialkylchlorophosphoramidite in the presence of an organic base.

* * * * *